United States Patent
Lemercier Lewandowski et al.

(10) Patent No.: US 12,024,491 B2
(45) Date of Patent: Jul. 2, 2024

(54) PROCESSES FOR MAKING MODULATORS OF CYSTIC FIBROSIS TRANSMEMBRANE CONDUCTANCE REGULATOR

(71) Applicant: Vertex Pharmaceuticals Incorporated, Boston, MA (US)

(72) Inventors: Berenice Lemercier Lewandowski, Braintree, MA (US); Robert Lewis, Waltham, MA (US); Adam Looker, Newtonville, MA (US); Adam Morgan, Ashland, MA (US); Stefanie Roeper, Medford, MA (US); Michael Ryan, Roxbury, MA (US); Juan Gabriel Solsona Rocabert, Barcelona (ES); Nathan Wilde, Poway, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 18/211,772

(22) Filed: Jun. 20, 2023

(65) Prior Publication Data
US 2024/0166607 A1    May 23, 2024

Related U.S. Application Data

(62) Division of application No. 16/768,178, filed as application No. PCT/US2018/063451 on Nov. 30, 2018, now Pat. No. 11,708,331.

(30) Foreign Application Priority Data

Dec. 1, 2017  (EP) ..................... 17382829

(51) Int. Cl.
C07D 215/56  (2006.01)
C07B 59/00   (2006.01)
C07C 39/06   (2006.01)
C07C 69/96   (2006.01)
C07C 205/43  (2006.01)
C07C 219/34  (2006.01)

(52) U.S. Cl.
CPC .......... *C07D 215/56* (2013.01); *C07B 59/002* (2013.01); *C07C 39/06* (2013.01); *C07C 69/96* (2013.01); *C07C 205/43* (2013.01); *C07C 219/34* (2013.01); *C07B 2200/05* (2013.01)

(58) Field of Classification Search
CPC .................................................. C07D 215/56
See application file for complete search history.

(56) References Cited

U.S. PATENT DOCUMENTS

| | | |
|---|---|---|
| 3,110,738 A | 11/1963 | Schmerling |
| 5,846,514 A | 12/1998 | Foster et al. |
| 6,221,335 B1 | 4/2001 | Foster |
| 6,440,710 B1 | 8/2002 | Keinan et al. |
| 6,603,008 B1 | 8/2003 | Ando et al. |
| 7,495,103 B2 | 2/2009 | Ruah et al. |
| 7,517,990 B2 | 4/2009 | Ito et al. |
| 7,553,855 B2 | 6/2009 | Young et al. |
| 8,076,357 B2 | 12/2011 | Young et al. |
| 8,101,767 B2 | 1/2012 | Ruah et al. |
| 8,163,772 B2 | 4/2012 | DeMattei et al. |
| 8,314,239 B2 | 11/2012 | Binch et al. |
| 8,324,242 B2 | 12/2012 | Ruah et al. |
| 8,354,427 B2 | 1/2013 | Van Goor |
| 8,362,253 B2 | 1/2013 | DeMattei et al. |
| 8,410,274 B2 | 4/2013 | Hurter et al. |
| 8,436,014 B2 | 5/2013 | Zhang et al. |
| 8,471,029 B2 | 6/2013 | Arekar et al. |

(Continued)

FOREIGN PATENT DOCUMENTS

| | | |
|---|---|---|
| CN | 1148843 A | 4/1997 |
| CN | 101765582 A | 6/2010 |

(Continued)

OTHER PUBLICATIONS

Notice of Allowance and Fee(s) due for U.S. Appl. No. 16/768,178, dated Jun. 20, 2023.
Baillie, T. A. (1981) "The Use of Stable Isotopes in Pharmacological Research" *Pharmacological Reviews*, 33(2):81-132.
Blake, M.I. et al. (1975) "Studies with Deuterated Drugs" *J Pharm Sci*, 64(3):367-391.
Bombieri, C. et al., "Recommendations for the classification of diseases of CFTR-related disorders," *J Cyst Fibros* 10:2 S86-S102 (2011).

(Continued)

*Primary Examiner* — John S Kenyon
(74) *Attorney, Agent, or Firm* — Finnegan, Henderson, Farabow, Garrett & Dunner, LLP

(57) ABSTRACT

The disclosure provides processes for synthesizing compounds for use as CFTR modulators.

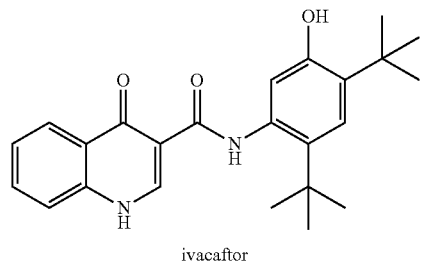

ivacaftor

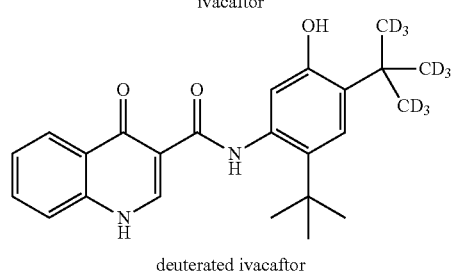
deuterated ivacaftor

21 Claims, No Drawings

(56) References Cited

U.S. PATENT DOCUMENTS

| | | |
|---|---|---|
| 8,476,442 B2 | 7/2013 | DeMattei et al. |
| 8,507,534 B2 | 8/2013 | Keshavarz-Shokri et al. |
| 8,513,282 B2 | 8/2013 | Binch et al. |
| 8,552,034 B2 | 10/2013 | Verwijs et al. |
| 8,598,205 B2 | 12/2013 | Binch et al. |
| 8,604,203 B2 | 12/2013 | Binch et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,629,162 B2 | 1/2014 | Hadida-Ruah et al. |
| 8,653,103 B2 | 2/2014 | Keshavarz-Shokri et al. |
| 8,674,108 B2 | 3/2014 | Luisi et al. |
| 8,741,925 B2 | 6/2014 | Hadida-Ruah et al. |
| 8,754,224 B2 | 6/2014 | Hurter et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,802,700 B2 | 8/2014 | Sheth et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,865,902 B2 | 10/2014 | Morgan |
| 8,883,206 B2 | 11/2014 | Dokou et al. |
| 8,969,382 B2 | 3/2015 | Binch et al. |
| 9,045,425 B2 | 6/2015 | Luisi et al. |
| 9,090,619 B2 | 7/2015 | Hadida-Ruah et al. |
| 9,139,530 B2 | 9/2015 | Hurter et al. |
| 9,150,552 B2 | 10/2015 | Keshavarz-Shokri et al. |
| 9,181,192 B2 | 11/2015 | Morgan |
| 9,241,934 B2 | 1/2016 | Verwijs et al. |
| 9,371,287 B2 | 6/2016 | DeMattei et al. |
| 9,434,717 B2 | 9/2016 | Keshavarz-Shokri et al. |
| 9,512,079 B2 | 12/2016 | Morgan |
| 9,670,163 B2 | 6/2017 | Hurter et al. |
| 9,676,722 B2 | 6/2017 | Desi Reddy et al. |
| 9,701,639 B2 | 7/2017 | Strohmeier et al. |
| 9,751,839 B2 | 9/2017 | Dematttei et al. |
| 9,840,499 B2 | 12/2017 | Keshavarz-Shokri et al. |
| 9,931,334 B2 | 4/2018 | Hurter et al. |
| 10,047,053 B2 | 8/2018 | Morgan |
| 10,272,046 B2 | 4/2019 | Dokou et al. |
| 10,479,766 B2 | 11/2019 | Morgan et al. |
| 10,537,565 B2 | 1/2020 | Hurter et al. |
| 10,646,481 B2 | 5/2020 | William et al. |
| 10,662,192 B2 | 5/2020 | Hadida-Ruah et al. |
| 10,759,721 B2 | 9/2020 | Morgan et al. |
| 10,894,773 B2 | 1/2021 | Morgan et al. |
| 11,291,662 B2 | 4/2022 | Hurter et al. |
| 11,564,916 B2 | 1/2023 | Rowe et al. |
| 11,708,331 B2 * | 7/2023 | Lemercier Lewandowski ............ C07C 37/0555 514/312 |
| 2007/0082929 A1 | 4/2007 | Gant et al. |
| 2007/0197695 A1 | 8/2007 | Potyen et al. |
| 2008/0103122 A1 | 5/2008 | Veltri |
| 2009/0105272 A1 | 4/2009 | Grootenhuis et al. |
| 2009/0246820 A1 | 10/2009 | Singh et al. |
| 2010/0074949 A1 | 3/2010 | Rowe et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0257223 A1 | 10/2011 | Van Goor et al. |
| 2011/0288122 A1 | 11/2011 | Van Goor et al. |
| 2012/0064157 A1 | 3/2012 | Dokou et al. |
| 2012/0122921 A1 | 5/2012 | DeMattei et al. |
| 2012/0122922 A1 | 5/2012 | Young et al. |
| 2012/0220625 A1 | 8/2012 | Rowe et al. |
| 2012/0258983 A1 | 10/2012 | Rowe et al. |
| 2013/0018071 A1 | 1/2013 | Arekar et al. |
| 2013/0090354 A1 | 4/2013 | Van Goor et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0224293 A1 | 8/2013 | Dokou et al. |
| 2013/0231368 A1 | 9/2013 | Zhang et al. |
| 2013/0303484 A1 | 11/2013 | Grootenhuis et al. |
| 2013/0331567 A1 | 12/2013 | Hadida-Ruah et al. |
| 2014/0023706 A1 | 1/2014 | Verwijs et al. |
| 2014/0112988 A1 | 4/2014 | Rowe et al. |
| 2014/0142138 A1 | 5/2014 | Van Goor et al. |
| 2014/0155431 A1 | 6/2014 | Hadida-Ruah et al. |
| 2014/0163011 A1 | 6/2014 | Hadida-Ruah et al. |
| 2014/0163068 A1 | 6/2014 | Verwijs et al. |
| 2014/0221424 A1 | 8/2014 | Zha |
| 2014/0243289 A1 | 8/2014 | Grootenhuis et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0343098 A1 | 11/2014 | Sheth et al. |
| 2014/0350281 A1 | 11/2014 | DeMattei et al. |
| 2015/0010628 A1 | 1/2015 | Dokou et al. |
| 2015/0024047 A1 | 1/2015 | Dokou et al. |
| 2015/0031722 A1 | 1/2015 | Hadida-Ruah et al. |
| 2015/0080431 A1 | 3/2015 | Van Goor et al. |
| 2015/0246031 A1 | 9/2015 | Dokou et al. |
| 2015/0293078 A1 | 10/2015 | Singh et al. |
| 2015/0315186 A2 | 11/2015 | Hadida-Ruah et al. |
| 2015/0336898 A1 | 11/2015 | Grootenhuis et al. |
| 2016/0022664 A2 | 1/2016 | Van Goor et al. |
| 2016/0022665 A2 | 1/2016 | Van Goor et al. |
| 2016/0067239 A9 | 3/2016 | Van Goor et al. |
| 2016/0221952 A1 | 8/2016 | Yang et al. |
| 2016/0303096 A1 | 10/2016 | Verwijs et al. |
| 2016/0318931 A1 | 11/2016 | Hadida-Ruah et al. |
| 2016/0324846 A1 | 11/2016 | Verwijs et al. |
| 2017/0137383 A1 | 5/2017 | Morgan |
| 2018/0125838 A1 | 5/2018 | Uttamsingh |
| 2018/0127398 A1 | 5/2018 | Keshavarz-Shokri et al. |
| 2018/0353500 A1 | 12/2018 | Braman |
| 2019/0274959 A1 | 9/2019 | Dokou et al. |
| 2020/0031776 A1 | 1/2020 | Morgan et al. |
| 2020/0290972 A1 | 9/2020 | Lewandowski et al. |
| 2021/0052570 A1 | 2/2021 | Uttamsingh |

FOREIGN PATENT DOCUMENTS

| | | | |
|---|---|---|---|
| CN | 102234275 A | 11/2011 | |
| CN | 102361855 A | 2/2012 | |
| CN | 103833630 A | 6/2014 | |
| JP | H09-510717 A | 10/1997 | |
| JP | 2005-529969 A | 10/2005 | |
| JP | 2005-532285 A | 10/2005 | |
| JP | 2008-504291 A | 2/2008 | |
| JP | 2010-539166 A | 12/2010 | |
| JP | 2014097964 A * | 5/2014 | |
| JP | 2014-515351 | 6/2014 | |
| WO | WO 1995/26325 A2 | 10/1995 | |
| WO | WO 2003/084954 A1 | 10/2003 | |
| WO | WO 2004/000854 A1 | 12/2003 | |
| WO | WO 2006/002421 A2 | 1/2006 | |
| WO | WO 2007/079139 A2 | 7/2007 | |
| WO | WO 2007/118651 A1 | 10/2007 | |
| WO | WO 2008/134525 A1 | 11/2008 | |
| WO | WO 2009/035652 A1 | 3/2009 | |
| WO | WO 2010/028015 A2 | 3/2010 | |
| WO | WO 2010/108162 A1 | 9/2010 | |
| WO | WO-2010108162 A1 * | 9/2010 | ............ A61K 31/47 |
| WO | WO 2011/072241 A1 | 6/2011 | |
| WO | WO 2011/116397 A1 | 9/2011 | |
| WO | WO 2012/158885 A1 | 11/2012 | |
| WO | WO 2013/006738 A1 | 1/2013 | |
| WO | WO 2014/078842 A1 | 5/2014 | |
| WO | WO 2015/063041 A1 | 5/2015 | |
| WO | WO 2017/053455 A1 | 3/2017 | |
| WO | WO 2017/053711 A2 | 3/2017 | |

(56) References Cited

FOREIGN PATENT DOCUMENTS

| WO | WO 2018/080591 A1 | 5/2018 |
|---|---|---|
| WO | WO 2019/109021 A1 | 6/2019 |

OTHER PUBLICATIONS

Browne, T. R. (1998) "Stable Isotope Techniques in Early Drug Development: An Economic Evaluation" *J Clin Pharmacol*, 38: 213-220.
Brunstrom, Jeffrey M. et al., "Measuring 'Expected Satiety' in a Range of Common Foods Using a Method of Constant Stimuli," Elsevier, Appetite 51, 2008, pp. 605-614, © 2008 Elsevier, www.elsevier.com/locate/appet.
Buck, Marcia L., "Ivacaftor for the Treatment of Patients with Cystic Fibrosis and the G551D-CFTR Mutation", Pediatric Pharmacotherapy, 18(4), four pages, Apr. 2012.
Buteau, K.C. (Jan. 2009) "Deuterated Drugs: Unexpectedly Nonobvious?" *Journal of High Technology Law*, 10(1):22-74.
Chen, Y. et al. (2011) "Drug-Drug Interaction between VX-770 and CYP3A Modulators" Abstracts of the 40th Annual Meeting of the American College of Clinical Pharmacology, Sep. 11-13, 2011, Chicago, Illinois. *J Clin Pharmacol*, 51:1348, Abstract 1122989.
Cherrah, Y. et al. (1987) "Study of Deuterium Isotope Effects on Protein Binding by Gas Chromatography/Mass Spectrometry. Caffeine and Deuterated Isotopomers" *Biomedical and Environmental Mass Spectrometry*, 14: 653-657.
Concert Pharmaceuticals, Inc. (2007) "Precision Deuterium Chemistry Backgrounder" [online]. Retrieved from the Internet: URL:http://www.webcitation.org/5e81SGCnl [retrieved on May 12, 2011] (6 pages).
Condren, Michelle E., et al., "Ivacaftor: A Novel Gene-Based Therapeutic Approach for Cystic Fibrosis", J Pediatr Pharmacol Ther 2013; 18(1):8-13.
Database PUBCHEM, Substance Record for SID 163435970. Create Date: Jun. 10, 2013. [retrieved on Oct. 24, 2016]. Retrieved from the Internet: https://pubchem.ncbi.nlm.nih.gov/substance/1634359070.
Dietrich CG, Götze O, Geier A. Molecular changes in hepatic metabolism and transport in cirrhosis and their functional importance. World J Gastroenterol. 2016;22(1):72-88.
Dyck, L. E. et al. (1986) "Effects of Deuterium Substitution on the Catabolism of β-Phenylethylamine: An in Vivo Study" *J Neurochem*, 46(2): 399-404.
European Medicines Agency. Kalydeco 150 mg film-coated tablets: summary of product characteristics; 2013.
European Patent Application No. 12725197: Response to Communication dated Jan. 7, 2014. European Patent Register, Jul. 15, 2014 (12 pages).
FDA Guidance for Industry, Pharmacokinetics in Patients with Impaired Hepatic Function: Study Design, Data Analysis, and Impact on Dosing and Labeling, 2003.
Fisher, M.B. et al. (2006) "The Complexities Inherent in Attempts to Decrease Drug Clearance by Blocking Sites of CYP-Mediated Metabolism" *Curr Opin Drug Discov Devel*, 9(1):101-109.
Fohner, Alison E., "PharmGKB summary: ivacaftor pathway, pharmacokinetics/pharmacodynamics", Pharmacogenet Genomics, Jan. 2017; 27(1):39-42.
Foster, A.B. (1984) "Deuterium Isotope Effects in Studies of Drug Metabolism" *Trends in Pharmacological Sciences*, 5:524-527.
Foster, A.B. (1985) "Deuterium Isotope Effects in the Metabolism of Drugs and Xenobiotics: Implications for Drug Design" *Advances in Drug Research*, 14:1-40.
Fukuto, J.M. et al. (1991) "Determination of the Mechanism of Demethylenation of (Methylenedioxy)phenyl Compounds by Cytochrome P450 Using Deuterium Isotope Effects" *J Med Chem*, 34:2871-2876.
Gouyette, A. (1988) "Synthesis of Deuterium-labelled Elliptinium and its Use in Metabolic Studies" *Biomedical and Environmental Mass Spectrometry*, 15:243-247.

Hadida, S. et al. (2014) "Discovery of N-(2,4-Di-tert-butyl-5-hydroxyphenyl)-4-oxo-1,4-dihydroquinoline-3-carboxamide (VX-770, Ivacaftor), a Potent and Orally Bioavailable CFTR Potentiator" *J Med Chem*, 57:9776-9795.
Haskins, N. J. (1982) "The Application of Stable Isotopes in Biomedical Research" *Biomedical Mass Spectrometry*, 9(7): 269-277.
Honma, S. et al. (1987) "The metabolism of roxatidine acetate hydrochloride. Liberation of deuterium from the piperidine ring during hydroxylation" *Drug Metabolism and Disposition*, 15(4):551-559.
International Preliminary Report on Patentability issued in International Patent Application PCT/US2016/052922; dated Apr. 5, 2018.
International Preliminary Report on Patentability issued in International Patent Application PCT/US2016/053323; dated Apr. 5, 2018.
International Search Report and Written Opinion issued in International Patent Application PCT/US2012/038297; dated Jul. 13, 2012 (11 pages).
International Search Report and Written Opinion issued in International Patent Application PCT/US2013/070748; dated Jan. 17, 2014 (12 pages).
International Search Report and Written Opinion issued in International Patent Application PCT/US2016/052922; dated Dec. 8, 2016 (8 pages).
International Search Report and Written Opinion issued in International Patent Application PCT/US2016/053323; dated Mar. 9, 2017 (10 pages).
International Search Report and Written Opinion issued in International Patent Application PCT/US2017/029920; dated Jul. 13, 2017 (8 pages).
Ivacaftor FDA Medical Review, Nov. 2011, pp. 1-109.
Kapoor et al. Ivacaftor: a novel mutation modulating drug. J. Clin. Diagn. Res. Nov. 2014;8(11):SE01-5. doi: 10.7860/JCDR/2014/6486.5158. Epub Nov. 20, 2014. PMID: 25584290; PMCID: PMC 4290359.
Kushner, D.J. et al. (1999) "Pharmacological Uses and Perspectives of Heavy Water and Deuterated Compounds" *Can J Physiol Pharmacol*, 77:79-88.
Mullard, A., Nat. Rev. Drug. Discov. 16 (2017), p. 305.
Nguyen et al. (Research article abstracts from the 10th international ISSX meeting, 2013, p. 309, "Deuterated isotopologs of ivacaftor have improved metabolism and pharmacokinetic properties".
O'Driscoll, C. (Mar. 9, 2009) "Heavyweight Drugs. Swapping Selected Hydrogen Atoms for Deuterium Could Be a Fast Route to Making Safer, Longer Lasting Drugs" *Chemistry & Industry*, pp. 24-26.
Olah, A. G. Et Al.: "Aluminum Chloride Catalyzed Nitration of Aromatics with Sodium Nitrate/Chlorotrimethylsilane", Synthesis 1994; 1994(5): 468-469.
Pieniaszek, H.J. et al. (1999) "Moricizine Bioavailability via Simultaneous, Dual, Stable Isotope Administration: Bioequivalence Implications" *J Clin Pharmacol*, 39:817-825.
Product Information Kalydeco™ (Ivacaftor), Vertex Pharmaceuticals Incorporated, 2013, p. 1-17.
Pubchem Compound No. CID 16220172 Database Record No. 873054-44-5; Create Date Jul. 23, 2007 [online]. Retrieved from: https://pubchem.ncbi.nlm.nih.gov/substance/390735681; on May 7, 2021 (46 pages).
Sanderson, K. (2009) "Big interest in heavy drugs. The drug industry is seeking profits by modifying hydrogen in existing medications" *Nature*, 458:269.
Schellekens, R. et al. (2011) "Applications of stable isotopes in clinical pharmacology" *British Journal of Clinical Pharmacology*, 72(6):879-897.
Shao, L. et al. (2010) "The kinetic isotope effect in the search for deuterated drugs" *Drug News Perspect*, 23(6):398-404.
Song et al. (2012) Ivacaftor: A new emerging treatment option in the management of cystic fibrosis. Formulary, 47(4), 132-134, 139-141.
Talal AH, Venuto CS, Younis I. Assessment of Hepatic Impairment and Implications for Pharmacokinetics of Substance Use Treatment. Clin Pharmacol Drug Dev. 2017;6(2):206-212.
Tonn, G.R. et al. (1993) "Simultaneous Analysis of Diphenhydramine and a Stable Isotope Analog ($^{2}H_{10}$)Diphenhydramine Using Capil-

(56) References Cited

OTHER PUBLICATIONS lary Gas Chromatography with Mass Selective Detection in Biological Fluids from Chronically Instrumented Pregnant Ewes" *Biological Mass Spectrometry*, 22:633-642.

Ursino, M. et al. (2017) "Dose-finding methods for Phase I clinical trials using pharmacokinetics in small populations," *Biometrical Journal*, 2017; 59(4): 804-825.

U.S. FDA, Center for Drug Evaluation and Research: Ivacaftor (VX-770), Application No. NDA 203-188Orig1s000, Clinical Pharmacology and Biopharmaceutics Review(s), Reference ID: 3073697; Jan. 18, 2012 (102 pages).

Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.

Van Goor, F. et al. (2009) "Rescue of CF airway epithelial cell function in vitro by a CFTR potentiator, VX-770" *PNAS*, 106(44):18825-18830.

Vertex Pharmaceuticals, Inc. (Jan. 2012) KALYDECO™ (ivacaftor) Tablets. Highlights of Prescribing Information (13 pages).

Wang, Shizhen (Ed.) "Use of Nuclear Technology in Drug Study" Chapter 21 in: *Molecular Nuclear Medicine*. 1st Ed. Beijing, China: Peking Union Medical College Press, Apr. 30, 2004; pp. 416-418 (Chinese).

Wolen, R.L. (1986) "The Application of Stable Isotopes to Studies of Drug Bioavailability and Bioequivalence" *J Clin Pharmacol*, 26:419-424.

Wuts, Peter G M et al., "Protection for phenols and catechols," Greene's Protective Groups in Organic Synthesis, fourth edition, © 2007, pp. 370-430.

\* cited by examiner

PROCESSES FOR MAKING MODULATORS OF CYSTIC FIBROSIS TRANSMEMBRANE CONDUCTANCE REGULATOR

This application is a divisional of U.S. patent application Ser. No. 16/768,178, filed May 29, 2020, now U.S. Pat. No. 11,708,331: which is a national stage application under 35 U.S.C. § 371 of international application number PCT/US2018/063451, filed Nov. 30, 2018, which designated the U.S. and claims priority from European Provisional Application No. 17382829.4, filed Dec. 1, 2017, the entire contents of which are hereby incorporated by reference.

The disclosure relates to processes for preparing compounds useful for treating a cystic fibrosis transmembrane conductance regulator (CFTR) mediated disease such as cystic fibrosis.

Cystic fibrosis (CF) is a recessive genetic disease that affects approximately 30,000 children and adults in the United States and approximately 30,000 children and adults in Europe. Despite progress in the treatment of CF, there is no cure.

CF is caused by mutations in the CFTR gene that encodes an epithelial chloride ion channel responsible for aiding in the regulation of salt and water absorption and secretion in various tissues. Small molecule drugs, known as potentiators, that increase the probability of CFTR channel opening represent one potential therapeutic strategy to treat CF.

Specifically, CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in CF, the most common fatal genetic disease in humans. CF affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with CF are infertile and fertility is decreased among females with CF. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease-causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, greater than 1000 disease-causing mutations in the CF gene have been identified (http://www.genet.sickkids.on.ca/cftr/app). The most prevalent mutation is a deletion of phenylalanine at position 508 of the CFTR amino acid sequence and is commonly referred to as ΔF508-CFTR. This mutation occurs in approximately 70% of the cases of CF.

The deletion of residue 508 in ΔF508-CFTR prevents the nascent protein from folding correctly. This results in the inability of the mutant protein to exit the endoplasmic reticulum and traffic to the plasma membrane. As a result, the number of channels present in the membrane is far fewer than observed in cells expressing wild-type CFTR. In addition to impaired trafficking, the mutation results in defective channel gating. Together, the reduced number of channels in the membrane and the defective gating lead to reduced anion transport across epithelia, leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease-causing mutations in CFTR that result in defective trafficking, synthesis, and/or channel gating could be up- or down-regulated to alter anion secretion and modify disease progression and/or severity.

There is a need for processes for the preparation of compounds that modulate CFTR activity and possess favorable absorption, distribution, metabolism, and/or excretion (ADME) properties. Ivacaftor, known by the chemical name N-(2,4-di-tert-butyl-5-hydroxyphenyl)-4-oxo-1,4-dihydro-quinoline-3-carboxamide and the brand name Kalydeco®, is a CFTR potentiator and is approved by the United States Food and Drug Administration (U.S. FDA) for the treatment of CF. Ivacaftor is also one of the active pharmaceutical ingredients of Symdeko®, which was approved by the U.S. FDA in February 2018 for treating patients with certain CFTR mutations. Ivacaftor is also one of the components of triple combination approaches for CF currently being tested in Phase III clinical trials (ivacaftor/tezacaftor/VX-659 and ivacaftor/tezacaftor/VX-445). Despite the beneficial activities of ivacaftor, there is a continuing need for modulators of CFTR activity and compositions thereof, which can be used to modulate the activity of the CFTR in the cell membrane of a mammal.

A deuterated form of ivacaftor, known by the chemical name N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide, also acts as a CFTR potentiator. This deuterated derivative of ivacaftor metabolizes more slowly than ivacaftor, which results in a slower drug clearance from the body. This slower metabolism allows less frequent or lower dosing of the drug.

There is a need for efficient processes for the synthesis of compounds useful as CFTR modulators that deliver these compounds in for example, higher yield, higher selectivity, or with higher purity relative to known processes. Accordingly, this disclosure provides processes for the synthesis of ivacaftor and pharmaceutically acceptable salts thereof. An alternative process for preparing ivacaftor is disclosed in PCT Publication No. WO 2010/108162. This disclosure also provides processes for the synthesis of a deuterated form of ivacaftor and pharmaceutically acceptable salts thereof.

In one embodiment, the disclosure provides a process for the preparation of ivacaftor (compound 1):

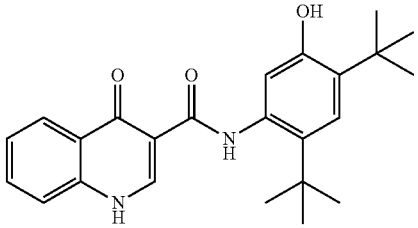

1 comprising:
(a) reacting compound 3:

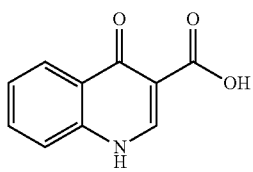

3 with compound 4:

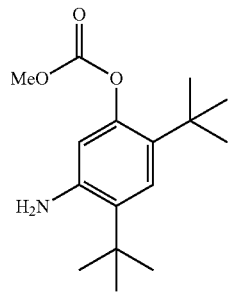

4 in the presence of T3P® and pyridine using 2-methyl tetrahydrofuran as the solvent to form compound 5

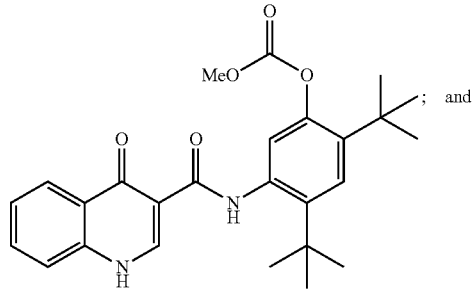

5

; and (b) reacting compound 5 with NaOMe/MeOH in 2-methyl tetrahydrofuran to form ivacaftor (compound 1).

In one embodiment, the disclosure provides a process for the preparation of a deuterated form of ivacaftor (compound 2):

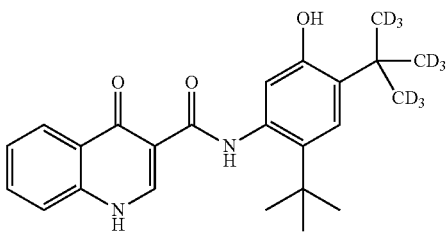

2 comprising:
(a) coupling compound 3:

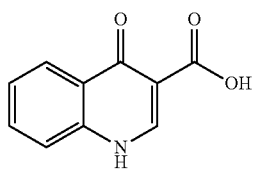

3 with compound 7:

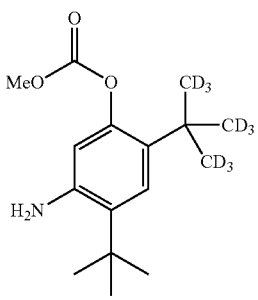

7 in the presence of T3P® and pyridine using 2-methyl tetrahydrofuran as the solvent to form compound 8

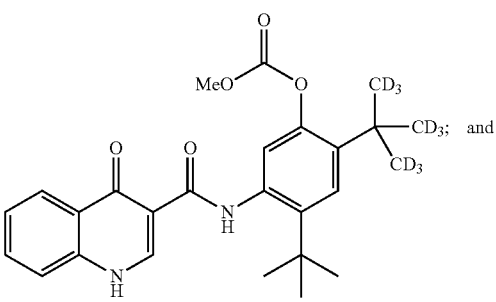

8

; and (b) reacting compound 8 with NaOMe/MeOH in 2-methyl tetrahydrofuran to form a deuterated form of ivacaftor (compound 2).

I. Definitions

The term "CFTR" as used herein means cystic fibrosis transmembrane conductance regulator or a mutation thereof capable of regulator activity.

The term "CFTR potentiator" as used herein refers to a compound that increases the channel activity of CFTR protein located at the cell surface, resulting in enhanced ion transport.

Compounds described herein may be optionally substituted with one or more substituents, as illustrated generally above, or as exemplified by particular classes, subclasses, and species of the disclosure. It will be appreciated that the phrase "optionally substituted" is used interchangeably with the phrase "substituted or unsubstituted." In general, the term "substituted," whether preceded by the term "optionally" or not, refers to the replacement of hydrogen radicals in a given structure with the radical of a specified substituent.

Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds.

The term "compound," when referring to a compound of this disclosure, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms will also contain lesser amounts of isotopologues having hydrogen atoms at one or more of the designated deuterium positions in that structure. The relative amount of such isotopologues in a compound of this disclosure will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The term "isotopologue" refers to a species in which the chemical structure differs from a specific compound of this disclosure only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$, are within the scope of this disclosure.

The term "stable," as used herein, refers to compounds that are not substantially altered when subjected to conditions to allow for their production, detection, and preferably their recovery, purification, and use for one or more of the purposes disclosed herein.

The term "stable compounds," as used herein, refers to compounds which possess stability sufficient to allow for their manufacture and which maintain the integrity of the compounds for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

Throughout the disclosure, wherever "methyl" (Me) is referenced in a structure containing a carbomethoxy carbonate (i.e., —OCO$_2$Me), it may be replaced with groups selected from "aliphatic," "heteroaliphatic," "heterocyclic," "haloaliphatic," "aryl," and "heteroaryl."

The term "aliphatic" or "aliphatic group", as used herein, means a straight-chain (i.e., unbranched) or branched, substituted, or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle", "cycloaliphatic", or "cycloalkyl"), that has a single point of attachment to the rest of the molecule. Unless otherwise specified, aliphatic groups contain one to twenty aliphatic carbon atoms. In some embodiments, aliphatic groups contain one to ten aliphatic carbon atoms. In other embodiments, aliphatic groups contain one to eight aliphatic carbon atoms. In still other embodiments, aliphatic groups contain one to six aliphatic carbon atoms, and in yet other embodiments aliphatic groups contain one to four aliphatic carbon atoms. In some embodiments, "cycloaliphatic" (or "carbocycle" or "cycloalkyl") refers to a monocyclic $C_{3-8}$ hydrocarbon or bicyclic or tricyclic $C_{8-14}$ hydrocarbon that is completely saturated or that contains one or more units of unsaturation, but which is not aromatic, that has a single point of attachment to the rest of the molecule wherein any individual ring in said bicyclic ring system has three to seven members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The term "heteroaliphatic," as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle," "heterocyclyl," "heterocycloaliphatic," or "heterocyclic" groups.

The term "heterocycle," "heterocyclyl," "heterocycloaliphatic," or "heterocyclic" as used herein means non-aromatic, monocyclic, bicyclic, or tricyclic ring systems in which one or more ring members is an independently selected heteroatom. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains three to seven ring members.

The term "heteroatom" means one or more of oxygen, sulfur, nitrogen, phosphorus, or silicon (including any oxidized form of nitrogen, sulfur, phosphorus, or silicon; the quaternized form of any basic nitrogen, or a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloaliphatic" and "haloalkoxy" means aliphatic or alkoxy, as the case may be, substituted with one or more halo atoms. The term "halogen" or "halo" means F, Cl, Br, or I. Examples of haloaliphatic include —CHF$_2$, —CH$_2$F, —CF$_3$, —CF$_2$—, or perhaloalkyl, such as —CF$_2$CF$_3$.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" also refers to heteroaryl ring systems as defined herein below.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members.

An aryl (including aralkyl, aralkoxy, aryloxyalkyl and the like) or heteroaryl (including heteroaralkyl and heteroarylalkoxy and the like) group may contain one or more substituents.

An aliphatic or heteroaliphatic group or a non-aromatic heterocyclic ring may contain one or more substituents.

The term "alcoholic solvent" as used herein represents a solvent that is an alcohol (e.g., methanol, ethanol).

The term "aprotic solvent" as used herein describes a solvent that lacks the ability to donate or exchange a proton.

The term "coupling reaction" as used herein describes the reaction of a carboxylic acid and an amine to form an amide bond.

The term "reducing agent" as used herein describes a compound that donates an electron to another species.

The term "alkoxyformylating" as used herein describes the protection of an alcohol with a —C(O)OR group to form a carbonate.

The term "halogenating agent" as used herein describes a reagent that replaces one or more C—H bonds with a corresponding number of C-X bonds, wherein X is a halogen.

Examples of useful protecting groups for carboxylic acids are substituted alkyl esters such as 9-fluorenylmethyl, methoxymethyl, methylthiomethyl, tetrahydropyranyl, tetrahydrofuranyl, methoxyethoxymethyl, 2-(trimethylsilyl) ethoxymethyl, benzyloxymethyl, pivaloyloxymethyl, phenylacetoxymethyl, triisopropropylsysilylmethyl, cyanomethyl, acetol, phenacyl, substituted phenacyl esters, 2,2,2-trichloroethyl, 2-haloethyl, ω-chloroalkyl, 2-(trimethylsilyl) ethyl, 2-methylthioethyl, t-butyl, 3-methyl-3-pentyl, dicyclopropylmethyl, cyclopentyl, cyclohexyl, allyl, methallyl, cinnamyl, phenyl, silyl esters, benzyl and substituted benzyl esters, and 2,6-dialkylphenyl esters such as pentafluorophenyl and 2,6-dialkylpyhenyl. Other useful protecting groups for carboxylic acids are methyl or ethyl esters.

Methods of adding (a process generally referred to as "protection") and removing (a process generally referred to as "deprotection") such amine and carboxylic acid protecting groups are well-known in the art and available, for example in P. J. Kocienski, Protecting Groups, Thieme, 1994, which is hereby incorporated by reference in its entirety and in Greene and Wuts, *Protective Groups in Organic Synthesis*, 3rd Edition (John Wiley & Sons, New York, 1999).

Examples of suitable solvents that may be used in this disclosure are, but not limited to, water, methanol (MeOH), methylene chloride (CH$_2$Cl$_2$), acetonitrile, N,N-dimethylformamide (DMF), methyl acetate (MeOAc), ethyl acetate (EtOAc), isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether (Et$_2$O), methyl tert-butyl ether (MTBE), 1,4-dioxane, and N-methyl pyrrolidone (NMP).

Examples of suitable coupling agents that may be used in this disclosure are, but not limited to, 1-(3-(dimethylamino)propyl)-3-ethyl-carbodiimide hydrochloride (EDCI), 2-(1H-benzotriazole-1-yl)-1,1,3,3-tetramethyluronium hexafluorophosphate (HBTU), 1-hydroxybenzotriazole (HOBT), 2-(1H-7-azabenzotriazol-1-yl)-1,1,3,3-tetramethyl uronium hexafluorophosphate (HATU), 2-chloro-1,3-dimethyl-2-imidazolium tetrafluoroborate, 1-H-benzotriazolium-1-[bis(dimethylamino)methylene]-5-chlorohexafluorophosphate (HCTU), 2-chloro-4,6-dimethoxy-1,3,5-triazine, and 2-propane phosphonic anhydride (T3P®).

Examples of suitable bases that may be used in this disclosure are, but not limited to, potassium carbonate (K$_2$CO$_3$), N-methylmorpholine (NMM), triethylamine (Et$_3$N; TEA), diisopropylethyl amine (i-Pr$_2$EtN; DIPEA), pyridine, potassium hydroxide (KOH), sodium hydroxide (NaOH), and sodium methoxide (NaOMe; NaOCH$_3$).

Unless otherwise stated, structures depicted herein are also meant to include all isomeric forms of the structure, e.g., geometric (or conformational), such as (Z) and (E) double bond isomers and (Z) and (E) conformational isomers. Therefore, geometric or conformational mixtures of the present compounds are within the scope of the disclosure. Unless otherwise stated, all tautomeric forms of the compounds of the disclosure are within the scope of the disclosure. A compound of Formula 9 may exist as a tautomer:

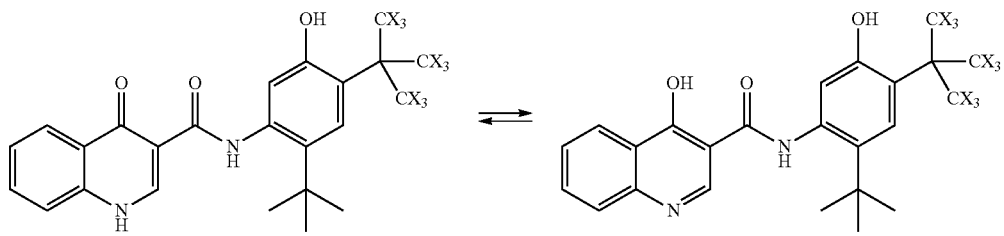

Tautomers of Formula 9

"D" and "d" both refer to deuterium. "Stereoisomer" refers to both enantiomers and diastereomers. "Tert" and "t-" each refer to tertiary.

"Substituted with deuterium" or "deuteration" refers to the replacement of one or more hydrogen atoms with a corresponding number of deuterium atoms. "Deuterated" refers to a compound that has undergone substitution with deuterium.

The disclosure also provides processes for preparing salts of the compounds of the disclosure.

A salt of a compound of this disclosure is formed between an acid and a basic group of the compound, such as an amino functional group, or a base and an acidic group of the compound, such as a carboxylic acid or phenolic functional group. According to another embodiment, the compound is a pharmaceutically acceptable salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate, and other salts. In one embodiment, pharmaceutically acceptable acid addition salts include those formed with mineral acids such as hydrochloric acid and hydrobromic acid, and preferably those formed with organic acids such as maleic acid.

It will be recognized that some variation of natural isotopic abundance occurs in a synthesized compound depending upon the origin of chemical materials used in the synthesis. Thus, a preparation of ivacaftor will inherently contain small amounts of deuterated isotopologues. The concentration of naturally abundant stable hydrogen and carbon isotopes, notwithstanding this variation, is small and immaterial as compared to the degree of stable isotopic substitution of compounds of this disclosure. See, for instance, Wada, E et al., Seikagaku, 1994, 66:15; Gannes, L Z et al., Comp Biochem Physiol Mol Integr Physiol, 1998, 119:725.

In the compounds of this disclosure, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium," the position is understood to have deuterium at an abundance that is at least 3000 times greater than the natural abundance of deuterium, which is 0.015% (i.e., at least 45% incorporation of deuterium).

The percentage of isotopic enrichment for each designated deuterium is at least 90%.

The term "isotopic enrichment factor" as used herein means the ratio between the isotopic abundance and the natural abundance of a specified isotope. In other embodiments, a compound of this disclosure has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiments, the percentage of isotopic enrichment for each designated deuterium is at least 90%.

In general, the disclosure provides processes for the synthesis of ivacaftor or pharmaceutically acceptable salts of ivacaftor and processes for the synthesis of deuterated derivatives of ivacaftor or pharmaceutically acceptable salts of deuterated derivatives of ivacaftor for use as potentiators of CFTR.

In particular, the disclosure provides a process for preparing ivacaftor (compound 1):

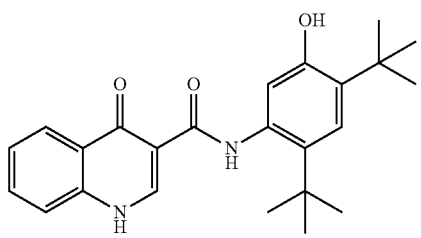

comprising converting compound 5:

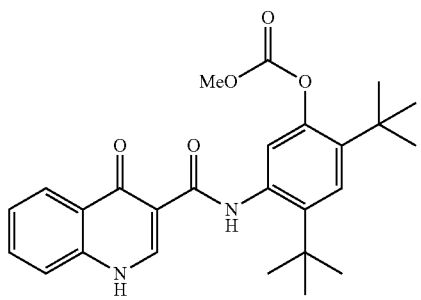

into ivacaftor (compound 1).

In some embodiments, the conversion of compound 5 into compound 1 is performed in the presence of a base and an alcoholic solvent.

In some embodiments, the base is selected from NaOH, KOH, and NaOMe.

In some embodiments, the base is NaOMe.

In some embodiments, the alcoholic solvent is methanol.

In some embodiments, the conversion is performed in the presence of an aprotic solvent.

In some embodiments, the aprotic solvent is 2-methyl tetrahydrofuran.

The disclosure further provides a process for the preparation of compound 5:

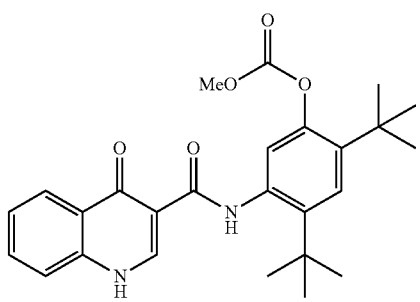

comprising reacting compound 3:

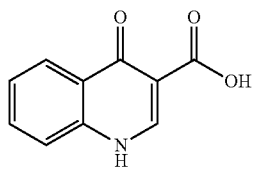

with compound 4:

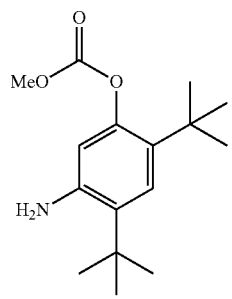

to form compound 5.

In some embodiments, the reaction of compound 3 with compound 4 is performed in the presence of a coupling agent.

In some embodiments, the coupling agent is selected from 2-chloro-1,3-dimethyl-2-imidazolium tetrafluoroborate, HBTU, HCTU, 2-chloro-4,6-dimethoxy-1,3,5-triazine, HATU, HOBT/EDC, and T3P®.

In some embodiments, the coupling agent is T3P®.

In some embodiments, the coupling reaction is performed in the presence of a base.

In some embodiments, the base is selected from $K_2CO_3$, $Et_3N$, NMM, pyridine, and DIPEA.

In some embodiments, the base is pyridine.

In some embodiments, the coupling reaction is performed in the presence of a solvent.

In some embodiments, the solvent is 2-methyl tetrahydrofuran.

The disclosure further provides a process for the preparation of compound 3:

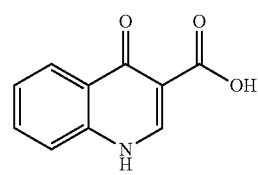

comprising converting compound 10:

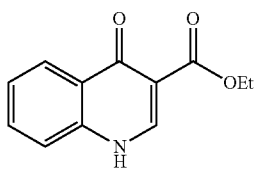

into compound 3.

In some embodiment, the conversion of compound 10 into compound 3 is performed in the presence of a base.

In some embodiments, the base is selected from NaOH, KOH, and NaOMe.

In some embodiments, the base is NaOMe.

In some embodiments, the conversion is performed in the presence of an acid.

In some embodiments, the acid is HCl.

The disclosure further provides a process for the preparation of compound 4:

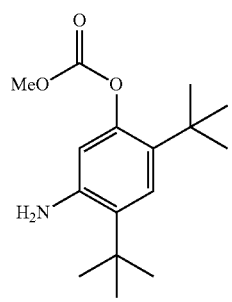

comprising converting compound 11A:

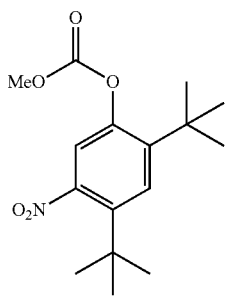

11A into compound 4.

In some embodiments, the conversion of compound 11A into compound 4 is performed in the presence of a reducing agent.

In some embodiments, the reducing agent is $H_2$.

In some embodiments, the reaction is performed in the presence of a transition-metal catalyst.

In some embodiments, the transition-metal catalyst is a platinum catalyst.

In some embodiments, the transition-metal catalyst is a palladium catalyst.

In some embodiments, the palladium catalyst is palladium on carbon.

In some embodiments, the reaction is performed in the presence of a solvent.

In some embodiments, the solvent is an alcohol.

In some embodiments, the alcohol is methanol.

The disclosure further provides a process for the preparation of compound 11A:

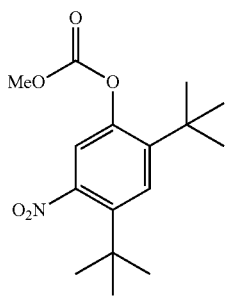

11A comprising converting compound 12:

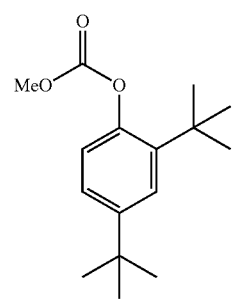

12 into compound 11A.

In some embodiments, the conversion of compound 12 into compound 11A is performed in the presence of one or more acids or salts.

In some embodiments, the one or more acids or salts is selected from $HNO_3$, $KNO_3$, $H_2SO_4$, $AlCl_3$, trimethylsilyl chloride, and $TiCl_4$.

In some embodiments, the one or more acids or salts is $HNO_3$ and $H_2SO_4$.

In some embodiments, the one or more acids or salts is $KNO_3$ and $H_2SO_4$.

In some embodiments, the one or more acids or salts is $KNO_3$, $AlCl_3$, and trimethylsilyl chloride.

In some embodiments, the one or more acids or salts is $KNO_3$, $TiCl_4$, and trimethylsilyl chloride.

In some embodiments, the one or more acids or salts is $NaNO_3$ and $AlCl_3$.

In some embodiments, the conversion is performed in the presence of a solvent.

In some embodiments, the solvent is $CH_2Cl_2$.

The disclosure further provides a process for the preparation of compound 12:

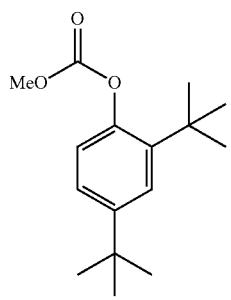

12 comprising converting compound 13:

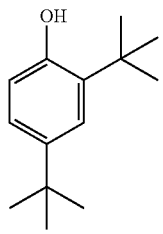

13 into compound 12.

In some embodiments, the conversion of compound 13 into compound 12 is performed with an alkoxyformylating agent.

In some embodiments, the alkoxyformylating agent is methyl chloroformate.

In some embodiments, the conversion is performed in the presence of a base.

In some embodiments, the base is an organic base.

In some embodiments, the organic base is $Et_3N$.

In some embodiments, the conversion is performed in the presence of a solvent.

In some embodiments, the solvent is $CH_2Cl_2$.

The disclosure further provides a process for the preparation of compound 2:

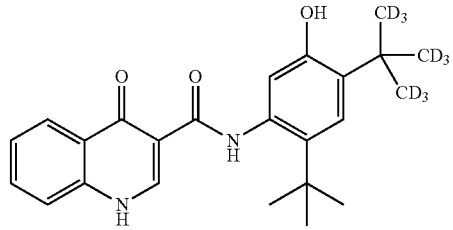
2 comprising converting compound 8:

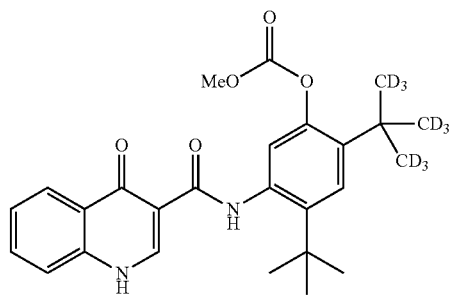
8 into compound 2.

In some embodiments, the conversion of compound 8 into compound 2 is performed in the presence of a base and alcoholic solvent.

In some embodiments, the base is selected from NaOH, KOH, and NaOMe.

In some embodiments, the base is NaOMe.

In some embodiments, the alcoholic solvent is methanol.

In some embodiments, the conversion is performed in the presence of an aprotic co-solvent.

In some embodiments, the aprotic solvent is 2-methyl tetrahydrofuran.

The disclosure further provides a process for the preparation of compound 8:

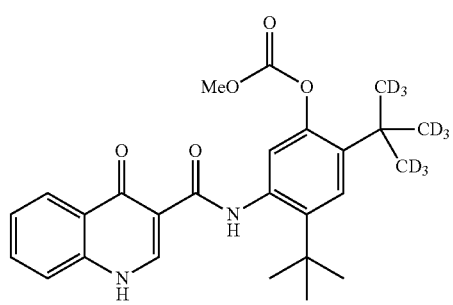
8 comprising reacting compound 3:

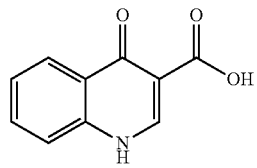
3 with compound 7:

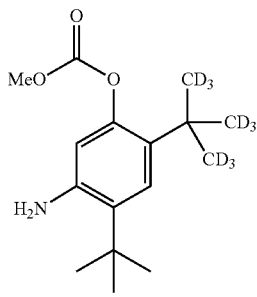
7 to form compound 8.

In some embodiments, the reaction of compound 3 with compound 7 is performed in the presence of a coupling agent.

In some embodiments, the coupling agent is selected from selected from 2-chloro-1,3-dimethyl-2-imidazolium tetrafluoroborate, HBTU, HCTU, 2-chloro-4,6-dimethoxy-1,3,5-triazine, HATU, HOBT/EDC, and T3P®.

In some embodiments, the coupling agent is T3P®.

In some embodiments, the coupling reaction is performed in the presence of a base.

In some embodiments, the base is selected from $K_2CO_3$, $Et_3N$, NMM, pyridine, and DIPEA.

In some embodiments, the base is pyridine.

In some embodiments, the coupling reaction is performed in the presence of a solvent.

In some embodiments, the solvent is 2-methyl tetrahydrofuran.

The disclosure further provides a process for the preparation of compound 7:

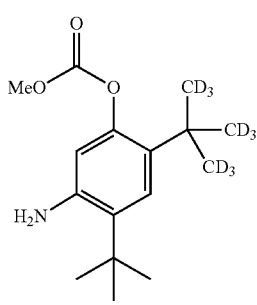
7 comprising converting compound 15:

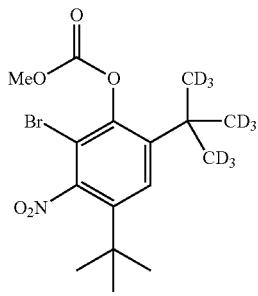

into compound 7.

In some embodiments, the conversion of compound 15 into compound 7 is performed in the presence of a reducing agent.

In some embodiments, the reducing agent is $H_2$.

In some embodiments, the conversion is performed in the presence of a transition-metal catalyst.

In some embodiments, the transition-metal catalyst is a platinum catalyst.

In some embodiments, the transition-metal catalyst is a palladium catalyst.

In some embodiments, the palladium catalyst is palladium on carbon.

In some embodiments, the conversion is performed in the presence of $Na_2HPO_4$.

In some embodiments, the conversion is performed in the presence of a solvent.

In some embodiments, the solvent is an alcohol.

In some embodiments, the alcohol is methanol.

The disclosure further provides a process for the preparation of compound 15:

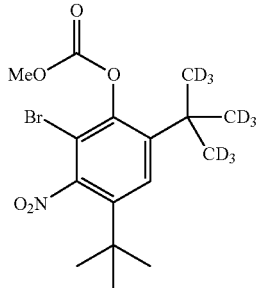

comprising converting compound 16:

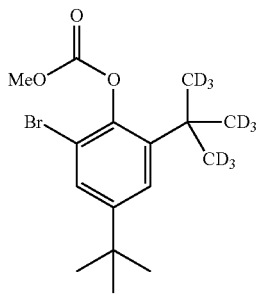

into compound 15.

In some embodiments, the conversion of compound 16 into compound 15 is performed in the presence of one or more acids or salts.

In some embodiments, the one or more acids or salts is selected from $HNO_3$, $KNO_3$, $H_2SO_4$, $AlCl_3$, trimethylsilyl chloride, and $TiCl_4$.

In some embodiments, the one or more acids or salts is $HNO_3$ and $H_2SO_4$.

In some embodiments, the one or more acids or salts is $KNO_3$ and $H_2SO_4$.

In some embodiments, the one or more acids or salts is $KNO_3$, $AlCl_3$, and trimethylsilyl chloride.

In some embodiments, the one or more acids or salts is $KNO_3$, $TiCl_4$, and trimethylsilyl chloride.

In some embodiments, the one or more acids or salts is $NaNO_3$ and $AlCl_3$.

In some embodiments, the conversion is performed in the presence of a solvent.

In some embodiments, the solvent is $CH_2Cl_2$.

The disclosure further provides a process for the preparation of compound 16:

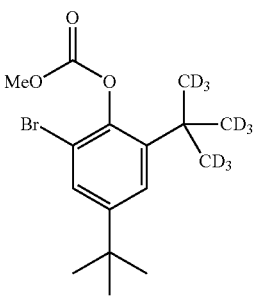

comprising converting compound 17:

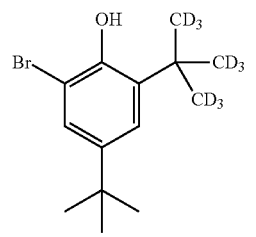

into compound 16.

In some embodiments, the conversion of compound 17 into compound 16 is performed with an alkoxyformylating agent.

In some embodiments, the alkoxyformylating agent is methyl chloroformate.

In some embodiments, the conversion is performed in the presence of a base.

In some embodiments, the base is an organic base.

In some embodiments, the organic base is $Et_3N$.

In some embodiments, the conversion is performed in the presence of a solvent.

In some embodiments, the solvent is $CH_2Cl_2$.

The disclosure further provides a process for the preparation of compound 17:

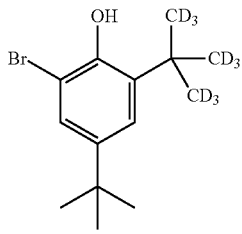

17 comprising converting compound 18:

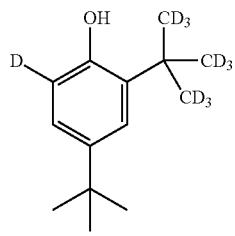

18 into compound 17.

In some embodiments, the conversion of compound 18 into compound 17 is performed in the presence of a halogenating agent.

In some embodiments, the halogenating agent is N-bromosuccinimide.

In some embodiments, the halogenating agent is $Br_2$.

In some embodiments, the conversion is performed in the presence of a solvent.

In some embodiments, the solvent is $CH_2Cl_2$.

The disclosure further provides a process for the preparation of compound 18:

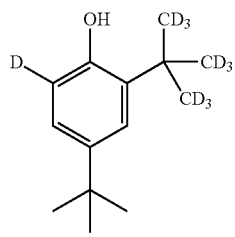

18 comprising converting compound 19:

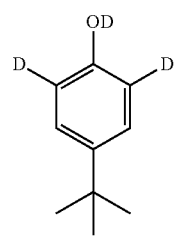

19 into compound 18.

In some embodiments, the conversion of compound 19 into compound 18 is performed in the presence of a source of —$C(CD_3)_3$.

In some embodiments, the source of —$C(CD_3)_3$ is tert-butanol-$d_{10}$.

In some embodiments, the source of —$C(CD_3)_3$ is tert-butyl acetate-$d_9$.

In some embodiments, the conversion is performed in the presence of an acid.

In some embodiments, the acid is $D_2SO_4$.

In some embodiments, the conversion is performed in the presence of a solvent.

In some embodiments, the solvent is $CH_2Cl_2$.

The disclosure further provides a process for the preparation of compound 19:

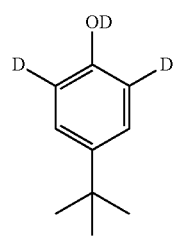

19 comprising converting compound 14:

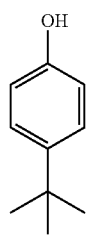

14 into compound 19.

In some embodiments, the conversion of compound 14 into compound 19 is performed in the presence of a source of deuterium.

In some embodiments, the source of deuterium is $D_2O$ and DCl.

In some embodiments, the conversion is performed in the presence of a base.

In some embodiments, the base is $K_2CO_3$.

In some embodiments, the conversion is performed in the presence of a solvent.

In some embodiments, the solvent is methanol-$d_1$.

In some embodiments, the solvent is $CH_2Cl_2$ and heptane.

The disclosure further provides a process for the preparation of compound 7:

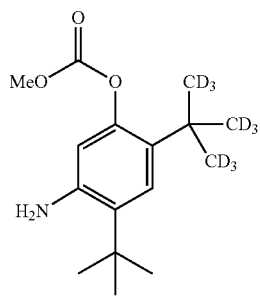

7 comprising converting compound 20:

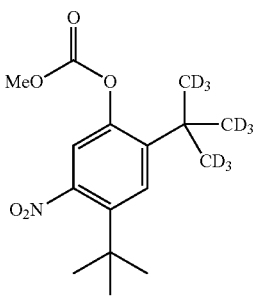

20 into compound 7.

In some embodiments, the conversion of compound 20 into compound 7 may be performed in the presence of a reducing agent.

In some embodiments, the reducing agent is $H_2$.

In some embodiments, the conversion may be performed in the presence of a transition-metal catalyst.

In some embodiments, the transition-metal catalyst is a platinum catalyst.

In some embodiments, the transition-metal catalyst is a palladium catalyst.

In some embodiments, the palladium catalyst is palladium on carbon.

In some embodiments, the conversion may be performed in the presence of $Na_2HPO_4$.

In some embodiments, the conversion may be performed in the presence of a solvent.

In some embodiments, the solvent is an alcohol.

In some embodiments, the alcohol is methanol.

The disclosure further provides a process for the preparation of compound 20:

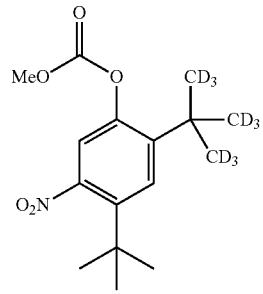

20 comprising converting compound 21:

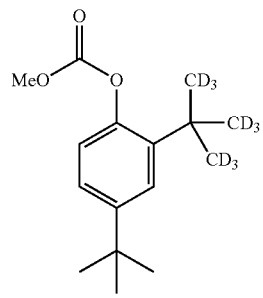

21 into compound 20.

In some embodiments, the conversion of compound 21 into compound 20 is performed in the presence of one or more acids or salts.

In some embodiments, the one or more acids or salts is selected from $HNO_3$, $KNO_3$, $H_2SO_4$, $AlCl_3$, trimethylsilyl chloride, and $TiCl_4$.

In some embodiments, the one or more acids or salts is $HNO_3$ and $H_2SO_4$.

In some embodiments, the one or more acids or salts is $KNO_3$ and $H_2SO_4$.

In some embodiments, the one or more acids or salts is $KNO_3$, $AlCl_3$, and trimethylsilyl chloride.

In some embodiments, the one or more acids or salts is $KNO_3$, $TiCl_4$, and trimethylsilyl chloride.

In some embodiments, the one or more acids or salts is $NaNO_3$ and $AlCl_3$.

In some embodiments, the conversion is performed in the presence of a solvent.

In some embodiments, the solvent is $CH_2Cl_2$.

The disclosure further provides a process for the preparation of compound 21:

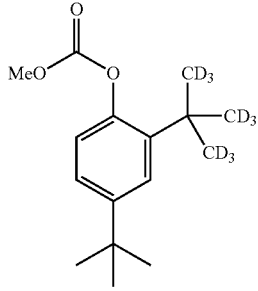

21 comprising converting compound 22:

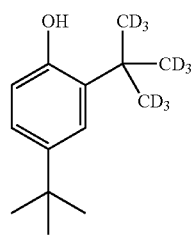

22 into compound 21.

In some embodiments, the conversion of compound 22 into compound 21 is performed with an alkoxyformylating agent.

In some embodiments, the alkoxyformylating agent is methyl chloroformate.

In some embodiments, the conversion is performed in the presence of a base.

In some embodiments, the base is an organic base.

In some embodiments, the base is Et₃N.

In some embodiments, the conversion is performed in the presence of a catalyst.

In some embodiments, the catalyst is 4-dimethylaminopyridine.

In some embodiments, the conversion is performed in the presence of a solvent.

In some embodiments, the solvent is CH₂Cl₂.

The disclosure further provides a process for the preparation of compound 22:

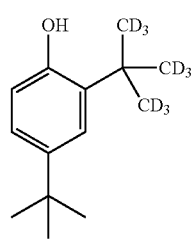

22 comprising converting compound 23:

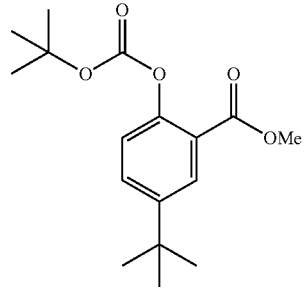

23 into compound 22.

In some embodiments, the conversion of compound 23 into compound 22 is performed in the presence of a source of —CD₃.

In some embodiments, the source of —CD₃ is CD₃MgI.

In some embodiments, the conversion is performed in the presence of a solvent.

In some embodiments, the solvent is a dialkyl ether solvent and THF.

In some embodiments, the dialkyl ether solvent is diethyl ether.

In some embodiments, the dialkyl ether solvent is dibutyl ether.

The disclosure further provides a process for the preparation of compound 23:

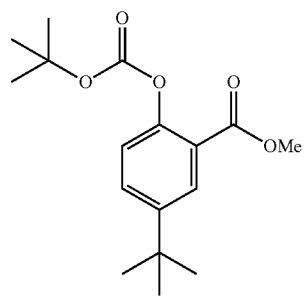

23 comprising converting compound 24:

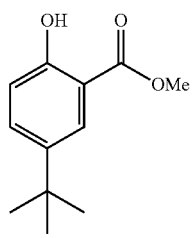

24 into compound 23.

In some embodiments, the conversion of compound 24 into 23 is performed in the presence of an alkoxyformylating agent.

In some embodiments, the alkoxyformylating agent is di-tert-butyl carbonate.

In some embodiments, the conversion is performed in the presence of a base.

In some embodiments, the base is sodium hydride.

In some embodiments, the base is DIPEA.

In some embodiments, the conversion is performed in the presence of a catalyst.

In some embodiments, the catalyst is 4-dimethylamino-pyridine.

In some embodiments, the conversion is performed in the absence of base or catalyst.

In some embodiments, the conversion is performed in the presence of a solvent.

In some embodiments, the solvent is $CH_2Cl_2$.

The disclosure further provides a process for the preparation of compound 24:

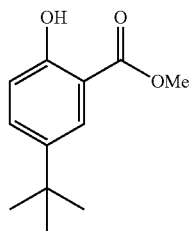

24 comprising converting compound 25:

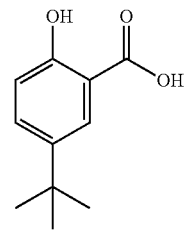

25 into compound 24.

In some embodiments, the conversion of compound 25 into compound 24 is performed in the presence of an acid and methanol.

In some embodiments, the acid is $H_2SO_4$.

The disclosure further provides a process for the preparation of compound 25:

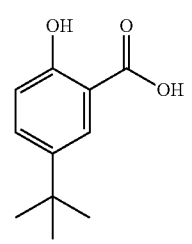

25 comprising converting compound 26:

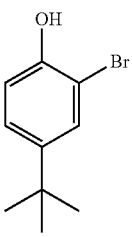

26 into compound 25.

In some embodiments, the conversion of compound 26 into compound 25 is performed in the presence of an organometallic reagent.

In some embodiments, the organometallic reagent is an organolithium reagent.

In some embodiments, the organolithium reagent is n-butyllithium.

In some embodiments, the conversion is performed in the presence of carbon dioxide.

In some embodiments, the conversion is performed in the presence of a solvent.

In some embodiments, the solvent is MTBE.

A listing of exemplary embodiments includes:

1. A process for the preparation of compound 1:

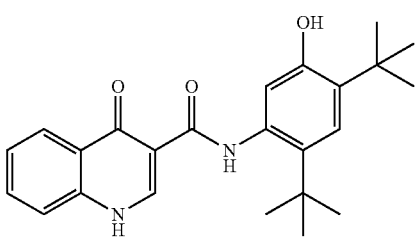

1 comprising converting compound 5:

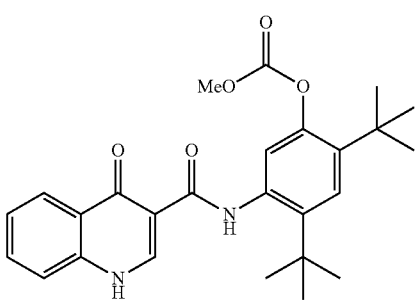

5 into compound 1, wherein the methyl (Me) of the —OCO₂Me of compound 5 is optionally replaced by a group selected from aliphatic, heteroaliphatic, heterocyclic, haloaliphatic, aryl, and heteroaryl.

2. The process of embodiment 1, wherein the conversion of compound 5 into compound 1 is performed in the presence of base and an alcoholic solvent.

3. The process of embodiment 2, wherein the base is selected from NaOH, KOH, and NaOMe.

4. The process of embodiment 3, wherein the base is NaOMe.
5. The process of embodiment 2, wherein the alcoholic solvent is methanol.
6. The process of embodiment 1, wherein the conversion is performed in the presence of an aprotic solvent.
7. The process of embodiment 6, wherein the aprotic solvent is 2-methyl tetrahydrofuran.
8. The process of embodiment 1, wherein compound 5 is produced by reacting compound 3:

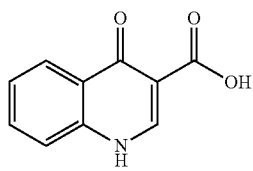

with compound 4:

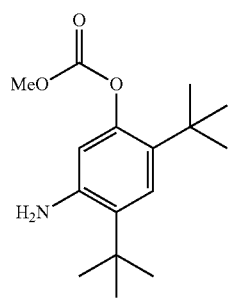

to form compound 5, wherein the methyl (Me) of the —OCO$_2$Me of compound 4 is optionally replaced by a group selected from aliphatic, heteroaliphatic, heterocyclic, haloaliphatic, aryl, and heteroaryl.
9. The process of embodiment 8, wherein the reaction of compound 3 with compound 4 is performed in the presence of a coupling agent.
10. The process of embodiment 9, wherein the coupling agent is selected from 2-chloro-1,3-dimethyl-2-imidazolium tetrafluoroborate, HBTU, HCTU, 2-chloro-4,6-dimethoxy-1,3,5-triazine, HATU, HOBT/EDC, and T3P®.
11. The process of embodiment 10, wherein the coupling agent is T3P®.
12. The process of embodiment 8, wherein the reaction is performed in the presence of a base.
13. The process of embodiment 12, wherein the base is selected from K$_2$CO$_3$, Et$_3$N, NMM, pyridine, and DIPEA.
14. The process of embodiment 13, wherein the base is pyridine.
15. The process of embodiment 8, wherein the reaction is performed in the presence of a solvent.
16. The process of embodiment 15, wherein the solvent is 2-methyl tetrahydrofuran.
17. The process of embodiment 8, wherein compound 4 is produced by converting compound 11A:

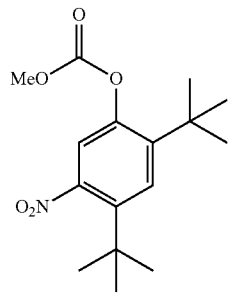

into compound 4, wherein the methyl (Me) of the —OCO$_2$Me of compound 11A is optionally replaced by a group selected from aliphatic, heteroaliphatic, heterocyclic, haloaliphatic, aryl, and heteroaryl.
18. The process of embodiment 17, wherein the conversion of compound 11A into compound 4 is performed in the presence of a reducing agent.
19. The process of embodiment 18, wherein the reducing agent is H$_2$.
20. The process of embodiment 17, wherein the conversion is performed in the presence of a transition-metal catalyst.
21. The process of embodiment 20, wherein the transition-metal catalyst is a platinum catalyst.
22. The process of embodiment 20, wherein the transition-metal catalyst is a palladium catalyst.
23. The process of embodiment 22, wherein the palladium catalyst is palladium on carbon.
24. The process of embodiment 17, wherein the conversion is performed in the presence of a solvent.
25. The process of embodiment 24, wherein the solvent is an alcohol.
26. The process of embodiment 25, wherein the alcohol is methanol.
27. The process of embodiment 17, wherein compound 11A is produced by converting compound 12

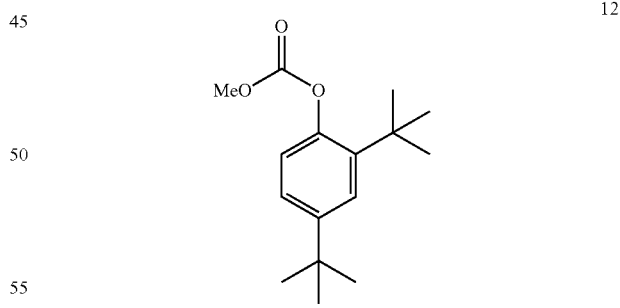

into compound 11A, wherein the methyl (Me) of the —OCO$_2$Me of compound 12 is optionally replaced by a group selected from aliphatic, heteroaliphatic, heterocyclic, haloaliphatic, aryl, and heteroaryl.
28. The process of embodiment 27, wherein the conversion of compound 12 into compound 11A is performed in the presence of one or more acids or salts.
29. The process of embodiment 28, wherein the one or more acids or salts is selected from HNO$_3$, KNO$_3$, H$_2$SO$_4$, AlCl$_3$, trimethylsilyl chloride, and TiCl$_4$.

30. The process of embodiment 29, wherein the one or more acids or salts is:
  i. HNO₃ and H₂SO₄;
  ii. KNO₃ and H₂SO₄;
  iii. KNO₃ and AlCl₃ and trimethylsilyl chloride;
  iv. KNO₃ and TiCl₄ and trimethylsilyl chloride; or
  v. NaNO₃ and AlCl₃.
31. The process of embodiment 27, wherein the conversion is performed in the presence of a solvent.
32. The process of embodiment 31, wherein the solvent is CH₂Cl₂.
33. The process of embodiment 27, wherein compound 12 is produced by converting compound 13:

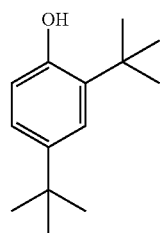

into compound 12.

34. The process of embodiment 33, wherein the conversion of compound 13 into compound 12 is performed with an alkoxyformylating agent.
35. The process of embodiment 34, wherein the alkoxyformylating agent is methyl chloroformate.
36. The process of embodiment 33, wherein the conversion is performed in the presence of a base.
37. The process of embodiment 36, wherein the base is an organic base.
38. The process of embodiment 37, wherein the organic base is DIPEA.
39. The process of embodiment 33, wherein the conversion is performed in the presence of a catalyst.
40. The process of embodiment 39, wherein the catalyst is 4-dimethylaminopyridine.
41. The process of embodiment 33, wherein the conversion is performed in the presence of a solvent.
42. The process of embodiment 41, wherein the solvent is CH₂Cl₂.
43. A process for the preparation of compound 2:

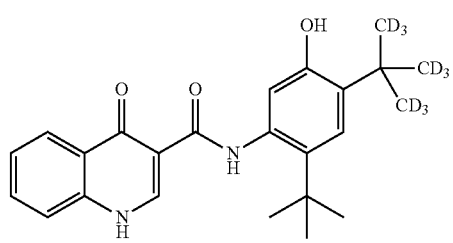

comprising converting compound 8:

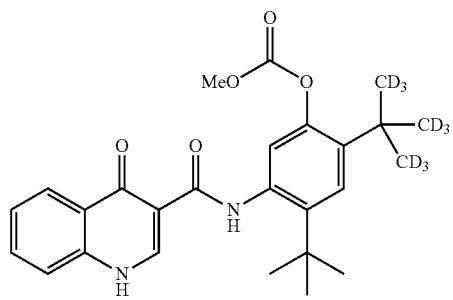

into compound 2, wherein the methyl (Me) of the —OCO₂Me of compound 8 is optionally replaced by a group selected from aliphatic, heteroaliphatic, heterocyclic, haloaliphatic, aryl, and heteroaryl.

44. The process of embodiment 43, wherein the conversion of compound 8 into compound 2 is performed by reacting compound 8 with a base in the presence of an alcoholic solvent.
45. The process of embodiment 44, wherein the base is selected from NaOH, KOH, and NaOMe.
46. The process of embodiment 45, wherein the base is NaOMe.
47. The process of embodiment 44, wherein the alcoholic solvent is methanol.
48. The process of embodiment 43, wherein the conversion is performed in the presence of an aprotic solvent.
49. The process of embodiment 48, wherein the solvent is 2-methyl tetrahydrofuran.
50. The process of embodiment 43, wherein compound 8 is produced by reacting compound 3:

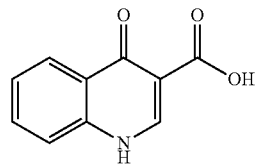

with compound 7:

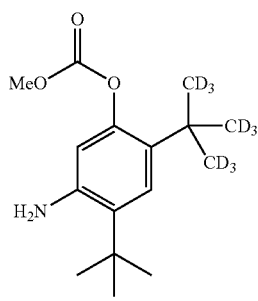

to form compound 8, wherein the methyl (Me) of the —OCO₂Me of compound 7 is optionally replaced by a group selected from aliphatic, heteroaliphatic, heterocyclic, haloaliphatic, aryl, and heteroaryl.

51. The process of embodiment 50, wherein the reaction of compound 3 with compound 7 is performed in the presence of a coupling agent.
52. The process of embodiment 51, wherein the coupling agent is selected from 2-chloro-1,3-dimethyl-2-imidazolium tetrafluoroborate, HBTU, HCTU, 2-chloro-4,6-dimethoxy-1,3,5-triazine, HATU, HOBT/EDC, and T3P®.
53. The process of embodiment 52, wherein the coupling agent is T3P®.
54. The process of embodiment 50, wherein the reaction is performed in the presence of a base.
55. The process of embodiment 54, wherein the base is selected from $K_2CO_3$, $Et_3N$, NMM, pyridine, and DIPEA.
56. The process of embodiment 55, wherein the base is pyridine.
57. The process of embodiment 50, wherein the reaction is performed in the presence of a solvent.
58. The process of embodiment 57, wherein the solvent is 2-methyl tetrahydrofuran.
59. The process of embodiment 50, wherein compound 7 is produced by converting compound 15:

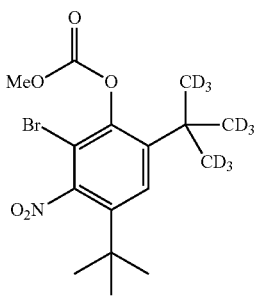

15 into compound 7, wherein the methyl (Me) of the —OCO$_2$Me of compound 15 is optionally replaced by a group selected from aliphatic, heteroaliphatic, heterocyclic, haloaliphatic, aryl, and heteroaryl.
60. The process of embodiment 59, wherein the conversion of compound 15 into compound 7 is performed in the presence of a reducing agent.
61. The process of embodiment 60, wherein the reducing agent is $H_2$.
62. The process of embodiment 59, wherein the conversion is performed in the presence of a transition-metal catalyst.
63. The process of embodiment 62, wherein the transition-metal catalyst is a platinum catalyst.
64. The process of embodiment 62, wherein the transition-metal catalyst is a palladium catalyst.
65. The process of embodiment 64, wherein the palladium catalyst is palladium on carbon.
66. The process of embodiment 59, wherein the conversion is performed in the presence of $Na_2HPO_4$.
67. The process of embodiment 59, wherein the conversion is performed in the presence of a solvent.
68. The process of embodiment 67, wherein the solvent is an alcohol.
69. The process of embodiment 68, wherein the alcohol is MeOH.
70. The process of embodiment 59, wherein compound 15 is produced by converting compound 16:

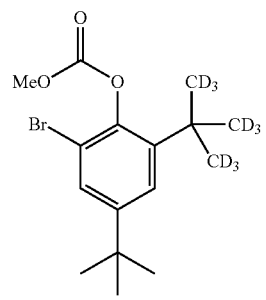

16 into compound 15, wherein the methyl (Me) of the —OCO$_2$Me of compound 16 is optionally replaced by a group selected from aliphatic, heteroaliphatic, heterocyclic, haloaliphatic, aryl, and heteroaryl.
71. The process of embodiment 70, wherein the conversion of compound 16 into compound 15 is performed in the presence of one or more acids or salts.
72. The process of embodiment 71, wherein the one or more acids or salts is selected from $HNO_3$, $KNO_3$, $H_2SO_4$, $AlCl_3$, trimethylsilyl chloride, and $TiCl_4$
73. The process of embodiment 72, wherein the one or more acids or salts is:
    i. $HNO_3$ and $H_2SO_4$;
    ii. $KNO_3$ and $H_2SO_4$;
    iii. $KNO_3$ and $AlCl_3$ and trimethylsilyl chloride;
    iv. $KNO_3$ and $TiCl_4$ and trimethylsilyl chloride; or
    v. $NaNO_3$ and $AlCl_3$.
74. The process of embodiment 70, wherein the conversion is performed in the presence of a solvent.
75. The process of embodiment 74, wherein the solvent is $CH_2Cl_2$.
76. The process of embodiment 70, wherein compound 16 is produced by converting compound 17:

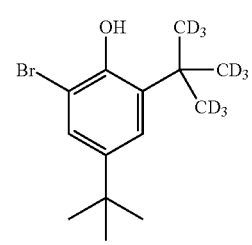

17 into compound 16.
77. The process of embodiment 76, wherein the conversion of compound 17 into compound 16 is performed with an alkoxyformylating agent.
78. The process of embodiment 77, wherein the alkoxyformylating agent is methyl chloroformate.
79. The process of embodiment 76, wherein the conversion is performed in the presence of a base.
80. The process of embodiment 79, wherein the base is an organic base.
81. The process of embodiment 80, wherein the organic base is DIPEA.
82. The process of embodiment 76, wherein the conversion is performed in the presence of a catalyst.
83. The process of embodiment 82, wherein the catalyst is 4-dimethylaminopyridine.

84. The process of embodiment 76, wherein the conversion is performed in the presence of a solvent.
85. The process of embodiment 84, wherein the solvent is CH₂Cl₂.
86. The process of embodiment 76, wherein compound 17 is produced by converting compound 18:

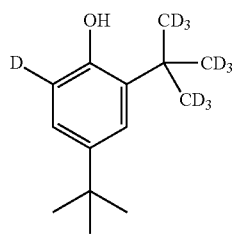

into compound 17.
87. The process of embodiment 86, wherein the conversion of compound 18 into compound 17 is performed in the presence of a halogenating agent.
88. The process of embodiment 87, wherein the halogenating agent is N-bromosuccinimide.
89. The process of embodiment 87, wherein the halogenating agent is Br₂.
90. The process of embodiment 86, wherein the conversion is performed in the presence of a solvent.
91. The process of embodiment 90, wherein the solvent is CH₂Cl₂.
92. The process of embodiment 86, wherein compound 18 is produced by converting compound 19:

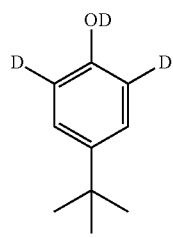

into compound 18.
93. The process of embodiment 92, wherein the conversion of compound 19 into compound 18 is performed in the presence of a source of —C(CD₃)₃.
94. The process of embodiment 93, wherein the source of —C(CD₃)₃ is tert-butanol-d₁₀.
95. The process of embodiment 93, wherein the source of —C(CD₃)₃ is tert-butyl acetate-d₉.
96. The process of embodiment 92, wherein the conversion is performed in the presence of an acid.
97. The process of embodiment 96, wherein the acid is D₂SO₄.
98. The process of embodiment 92, wherein the conversion is performed in the presence of a solvent.
99. The process of embodiment 98, wherein the solvent is CH₂Cl₂.
100. The process of embodiment 92, wherein compound 19 is produced by converting tert-butyl phenol (compound 14):

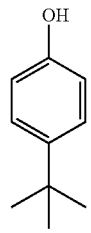

into compound 19.
101. The process of embodiment 100, wherein the conversion of compound 14 into compound 19 is performed in the presence of a source of deuterium.
102. The process of embodiment 101, wherein the source of deuterium is DCl and D₂O.
103. The process of embodiment 100, wherein the conversion is performed in the presence of a solvent.
104. The process of embodiment 103, wherein the solvent is methanol-d₁.
105. The process of embodiment 103, wherein the solvent is a mixture of methylene chloride and heptane.
106. The process of embodiment 100, wherein the conversion is performed in the presence of a base.
107. The process of embodiment 106, wherein the base is K₂CO₃.
108. The process of embodiment 50, wherein compound 7 is produced by converting compound 20:

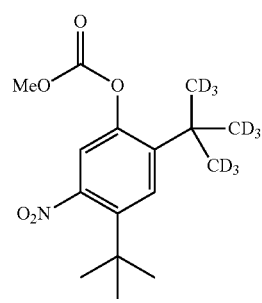

into compound 7, wherein the methyl (Me) of the —OCO₂Me of compound 20 is optionally replaced by a group selected from aliphatic, heteroaliphatic, heterocyclic, haloaliphatic, aryl, and heteroaryl.
109. The process of embodiment 108, wherein the conversion of compound 20 into compound 7 is performed with a reducing agent.
110. The process of embodiment 109, wherein the reducing agent is H₂.
111. The process of embodiment 108, wherein the conversion is performed in the presence of a transition-metal catalyst.
112. The process of embodiment 111, wherein the transition-metal catalyst is a platinum catalyst.
113. The process of embodiment 111, wherein the transition-metal catalyst is a palladium catalyst.
114. The process of embodiment 113, wherein the palladium catalyst is palladium on carbon.
115. The process of embodiment 108, wherein the conversion is performed in the presence of a solvent.
116. The process of embodiment 115, wherein the solvent is an alcohol.

117. The process of embodiment 116, wherein the alcohol is methanol.

118. The process of embodiment 108, wherein compound 20 is produced by converting compound 21:

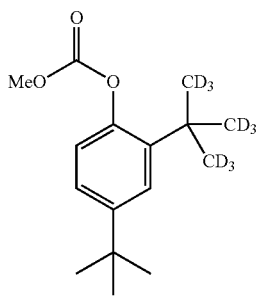

21 into compound 20, wherein the methyl (Me) of the —OCO$_2$Me of compound 21 is optionally replaced by a group selected from aliphatic, heteroaliphatic, heterocyclic, haloaliphatic, aryl, and heteroaryl.

119. The process of embodiment 118, wherein the conversion of compound 21 into compound 20 is performed in the presence of one or more acids or salts.

120. The process of embodiment 119, wherein the one or more acids or salts is selected from HNO$_3$, KNO$_3$, H$_2$SO$_4$, AlCl$_3$, trimethylsilyl chloride, and TiCl$_4$ 121. The process of embodiment 120, wherein the one or more acids or salts is:
  i. HNO$_3$ and H$_2$SO$_4$;
  ii. KNO$_3$ and H$_2$SO$_4$;
  iii. KNO$_3$ and AlCl$_3$ and trimethylsilyl chloride;
  iv. KNO$_3$ and TiCl$_4$ and trimethylsilyl chloride; or
  v. NaNO$_3$ and AlCl$_3$.

122. The process of embodiment 118, wherein the conversion is performed in the presence of a solvent.

123. The process of embodiment 122, wherein the solvent is CH$_2$Cl$_2$.

124. The process of embodiment 118, wherein compound 21 is produced by converting compound 22:

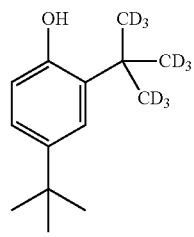

22 into compound 21.

125. The process of embodiment 124, wherein the conversion of compound 22 into compound 21 is performed in the presence of an alkoxyformylating agent.

126. The process of embodiment 125, wherein the alkoxyformylating agent is methyl chloroformate.

127. The process of embodiment 124, wherein the conversion is performed in the presence of a base.

128. The process of embodiment 127, wherein the base is DIPEA.

129. The process of embodiment 124, wherein the conversion is performed in the presence of a catalyst.

130. The process of embodiment 129, wherein the catalyst is 4-dimethylaminopyridine.

131. The process of embodiment 124, wherein the conversion is performed in the presence of a solvent.

132. The process of embodiment 131, wherein the solvent is CH$_2$Cl$_2$.

133. The process of embodiment 124, wherein compound 22 is produced by converting compound 23:

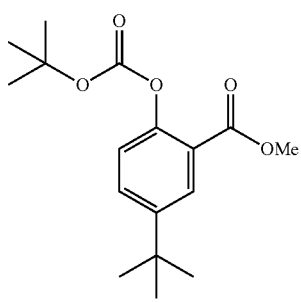

23 into compound 22.

134. The process of embodiment 133, wherein the conversion of compound 23 into compound 22 is performed in the presence of a source of —CD$_3$.

135. The process of embodiment 134, wherein the source of —CD$_3$ is CD$_3$MgI.

136. The process of embodiment 133, wherein the conversion is performed in the presence of a solvent.

137. The process of embodiment 136, wherein the solvent is a dialkyl ether solvent and tetrahydrofuran.

138. The process of embodiment 137, wherein the dialkyl solvent is diethyl ether.

139. The process of embodiment 137, wherein the dialkyl solvent is dibutyl ether.

140. The process of embodiment 133, wherein compound 23 is produced by converting compound 24:

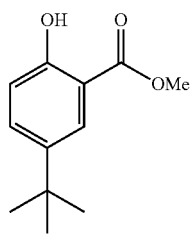

24 into compound 23.

141. The process of embodiment 140, wherein the conversion of compound 24 into compound 23 is performed with an alkoxyformylating agent.

142. The process of embodiment 141, wherein the alkoxyformylating agent is di-tert-butyl carbonate.

143. The process of embodiment 140, wherein the conversion is performed in the presence of a base.

144. The process of embodiment 143, wherein the base is sodium hydride.

145. The process of embodiment 143, wherein the base is DIPEA.

146. The process of embodiment 140, wherein the conversion is performed in the presence of a catalyst.

147. The process of embodiment 146, wherein the catalyst is 4-dimethylaminopyridine.

148. The process of embodiment 140, wherein the conversion is performed in the absence of base.

149. The process of embodiment 140, wherein the conversion is performed in the presence of a solvent.

150. The process of embodiment 149, wherein the solvent is $CH_2Cl_2$.

151. The process of embodiment 140, further wherein compound 24 is produced by converting compound 25:

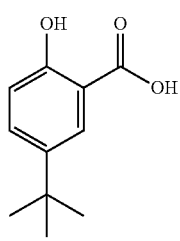

25 into compound 24.

152. The process of embodiment 151, wherein the conversion of compound 25 into compound 24 is performed in the presence of an acid.

153. The process of embodiment 152, wherein the acid is $H_2SO_4$.

154. The process of embodiment 151, wherein the conversion is performed in the presence of methanol.

155. The process of embodiment 151, wherein compound 25 is produced by converting compound 26:

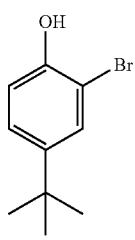

26 into compound 25.

156. The process of embodiment 155, wherein the conversion of compound 26 into compound 25 is performed in the presence of an organometallic reagent.

157. The process of embodiment 156, wherein the organometallic reagent is an organolithium reagent.

158. The process of embodiment 157, wherein the organolithium reagent is n-butyllithium.

159. The process of embodiment 155, wherein the conversion is performed in the presence of solid carbon dioxide.

160. The process of embodiment 155, wherein the conversion is performed in the presence of a solvent.

161. The process of embodiment 160, wherein the solvent is MTBE.

162. A process for the synthesis of compound 11A:

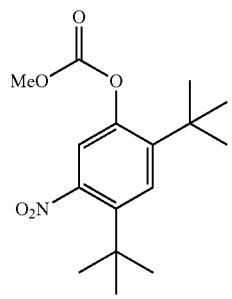

11A comprising reacting compound 12:

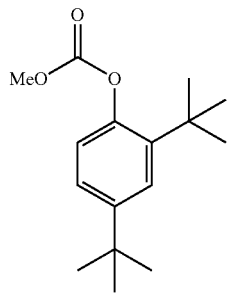

12 in the presence of $NaNO_3$ and $AlCl_3$ to form compound 11A, wherein the methyl (Me) of the —$OCO_2Me$ of compound 12 is optionally replaced by a group selected from aliphatic, heteroaliphatic, heterocyclic, haloaliphatic, aryl, and heteroaryl.

163. A process for the synthesis of compound 15:

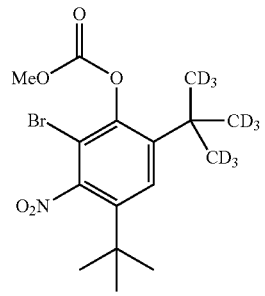

15 comprising reacting compound 16:

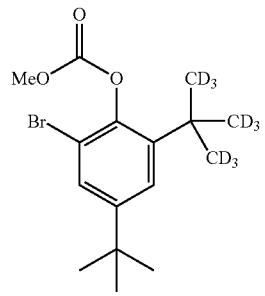

16 in the presence of NaNO₃ and AlCl₃ to form compound 15, wherein the methyl (Me) of the —OCO₂Me of compound 16 is optionally replaced by a group selected from aliphatic, heteroaliphatic, heterocyclic, haloaliphatic, aryl, and heteroaryl.

164. A process for the synthesis of compound 22:

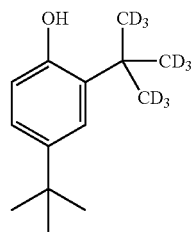

22 comprising reacting compound 23:

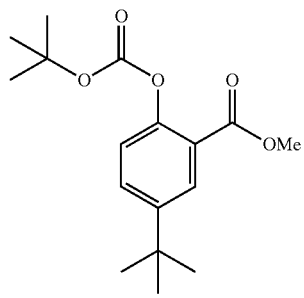

23 in the presence of CD₃MgI to form compound 22.

165. A process for the synthesis of compound 20:

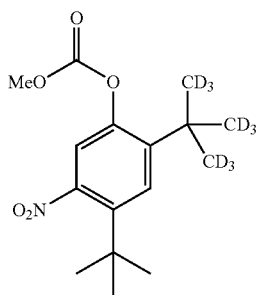

20 comprising reacting compound 21:

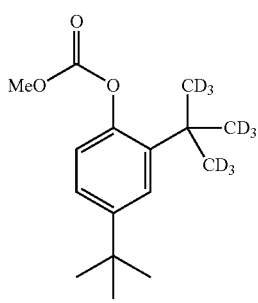

21 in the presence of NaNO₃ and AlCl₃ to form compound 20, wherein the methyl (Me) of the —OCO₂Me of compound 21 is optionally replaced by a group selected from aliphatic, heteroaliphatic, heterocyclic, haloaliphatic, aryl, and heteroaryl.

166. Compound 7:

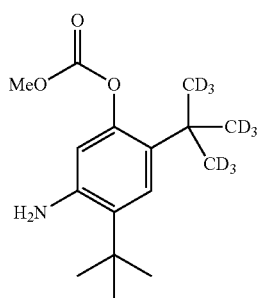

7 or a salt thereof.

167. Compound 8:

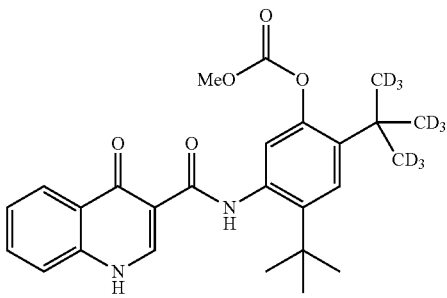

8 or a salt thereof.

168. Compound 15:

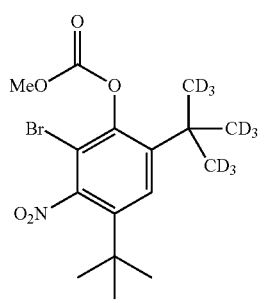

15 or a salt thereof.

169. Compound 16:
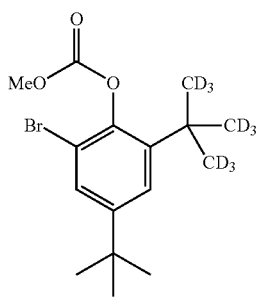
or a salt thereof.
170. Compound 17:
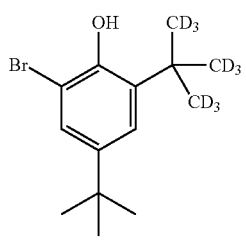
or a salt thereof.
171. Compound 20:
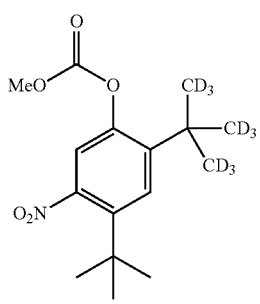
or a salt thereof
172. Compound 21:
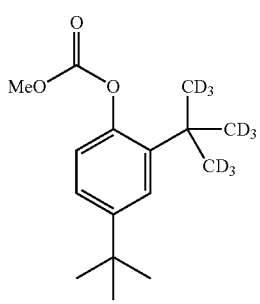
or a salt thereof
173. Compound 22:
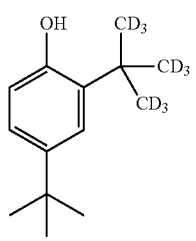
or a salt thereof
174. Compound 23:
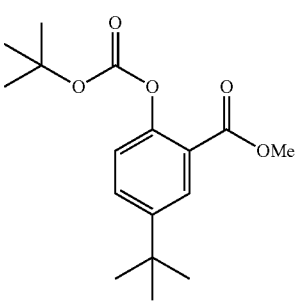
or a salt thereof.
II. General Synthesis
Compound 1 can be synthesized according to Scheme 1.
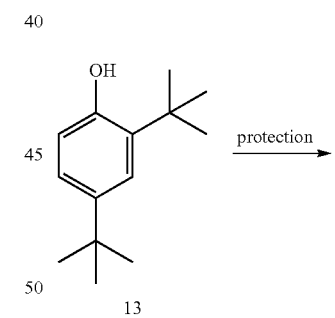
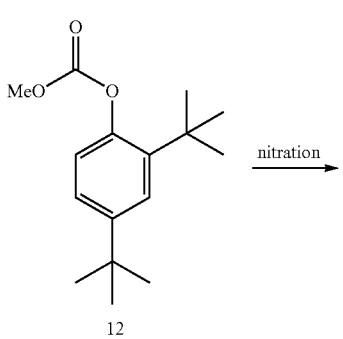

-continued

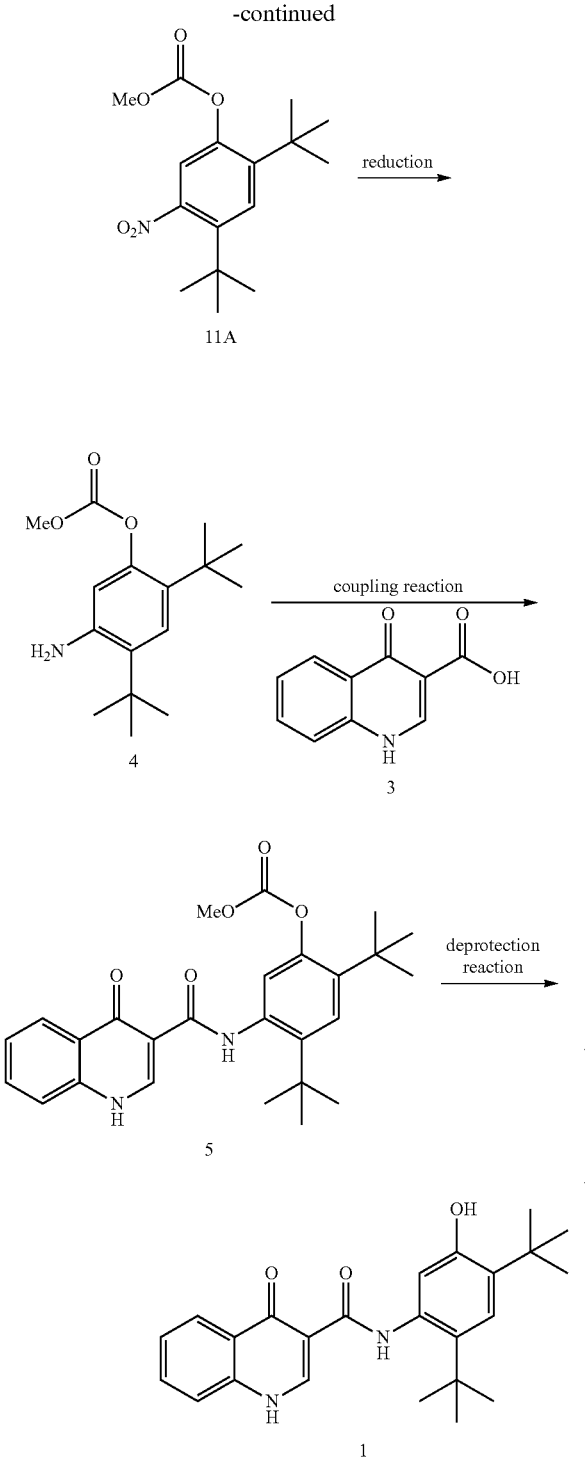

In some embodiments, the disclosure is directed to a process comprising one or more of the following steps:

a. Reacting compound 13 with an alkoxyformylating agent;
b. Reacting compound 12 with a nitrating agent;
c. Reacting compound 11A with a reducing agent;
d. Reacting compound 4 with compound 3;
e. Reacting compound 5 with a base.

Compound 3 can be prepared as disclosed in PCT Publication No. WO 2010/108162.

Compound 2 can be synthesized according to Scheme 2.

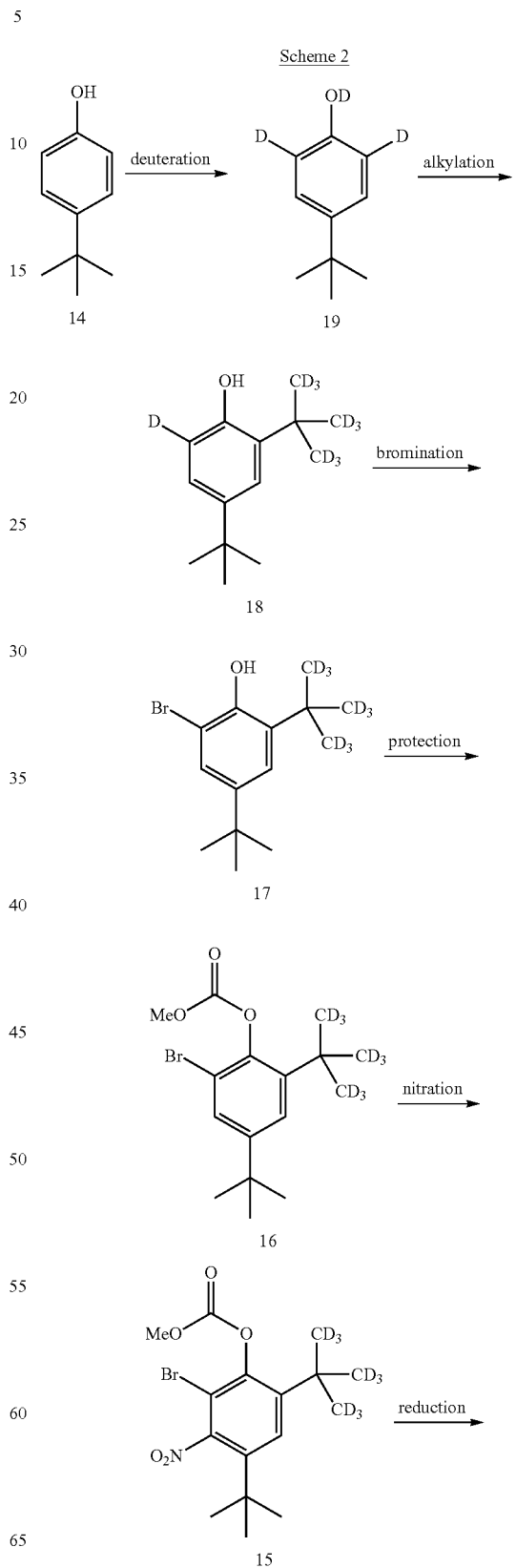

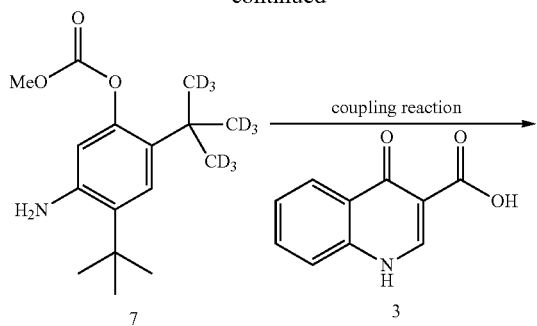

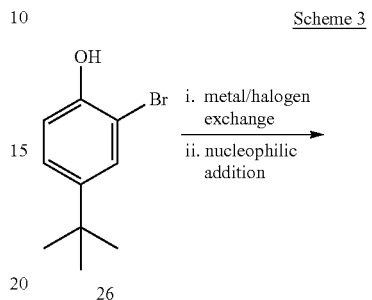

In one embodiment, the disclosure is directed to a process comprising one or more of the following steps:

a. Reacting compound 14 with a source of deuterium;
b. Reacting compound 19 with a source of —C(CD$_3$)$_3$;
c. Reacting compound 18 with a brominating agent;
d. Reacting compound 17 with an alkoxyformylating agent;
e. Reacting compound 16 with a nitrating agent;
f. Reacting compound 15 with a reducing agent;
g. Reacting compound 7 with compound 3; and
h. Reacting compound 8 with a base.

Compound 3 can be prepared as disclosed in PCT Publication No. WO 2010/108162.

Compound 2 can be prepared wherein each D in the CD$_3$ group has an isotopic enrichment of at least 90%.

Compound 2 may also be prepared as outlined in Scheme 3.

Scheme 3

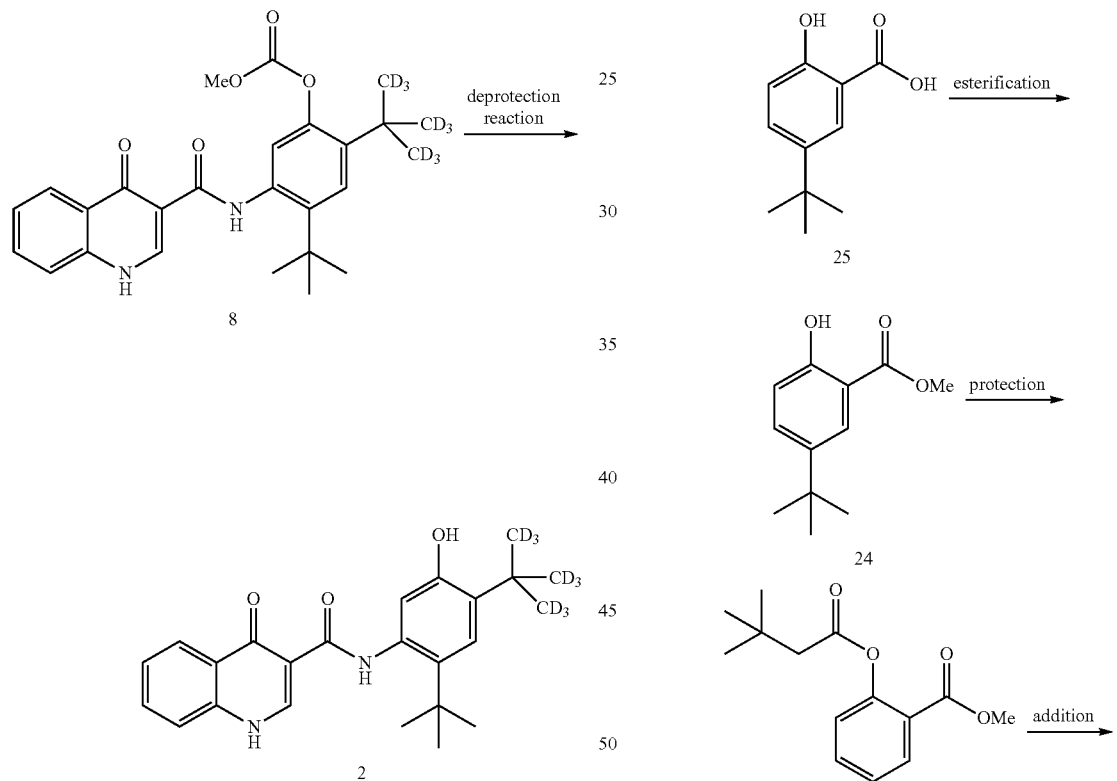

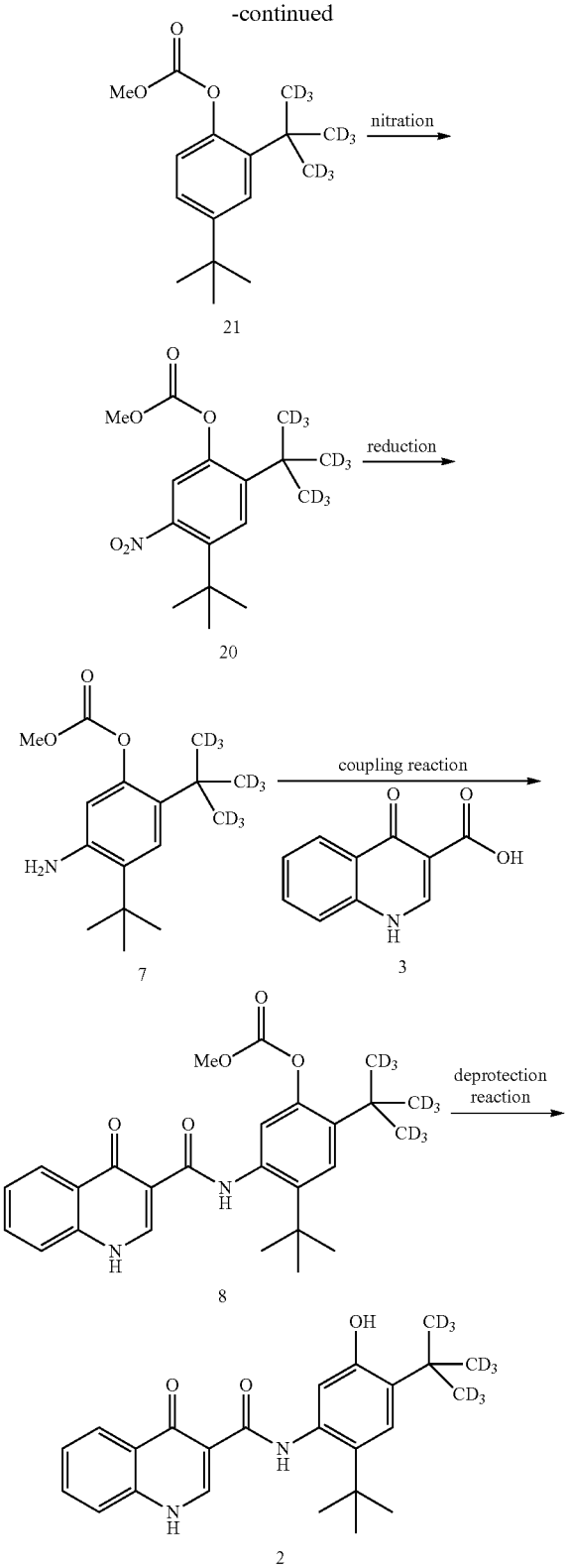

b. Subjecting compound 25 to esterification reaction conditions;
c. Reacting compound 24 with a protecting agent;
d. Reacting compound 23 with a source of —$C(CD_3)_3$;
e. Reacting compound 22 with an alkoxyformylating agent;
f. Reacting compound 21 with a nitrating agent;
g. Reacting compound 20 with a reducing agent.
h. Reacting compound 7 with compound 3; and
i. Reacting compound 8 with a base.

Compound 3 can be prepared as disclosed in PCT Publication No. WO 2010/108162.

Compound 2 can be prepared wherein each D in the $CD_3$ group has an isotopic enrichment of at least 90%.

The synthesis of compounds 1 and 2 may be readily achieved by synthetic chemists of ordinary skill by reference to the General Synthesis and Examples disclosed herein.

In order that the disclosure described herein may be more fully understood, the following examples are set forth. It should be understood that these examples are for illustrative purposes only and are not to be construed as limiting this disclosure in any manner.

III. EXAMPLES

Example 1: Synthesis of N-(2,4-di-tert-butyl-5-hydroxyphenyl)-4-oxo-1,4-dihydroquinoline-3-carboxamide (1)

The overall scheme of the synthesis of compound 1 is shown below.

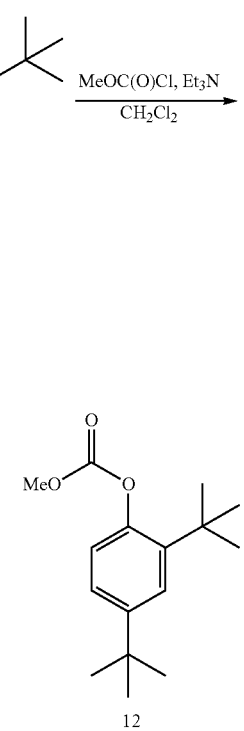

In one embodiment, the disclosure is directed to a process comprising one or more of the following steps:
a. Reacting compound 26 with a metal to effect metal/halogen exchange, then reacting the product with an appropriate electrophile;

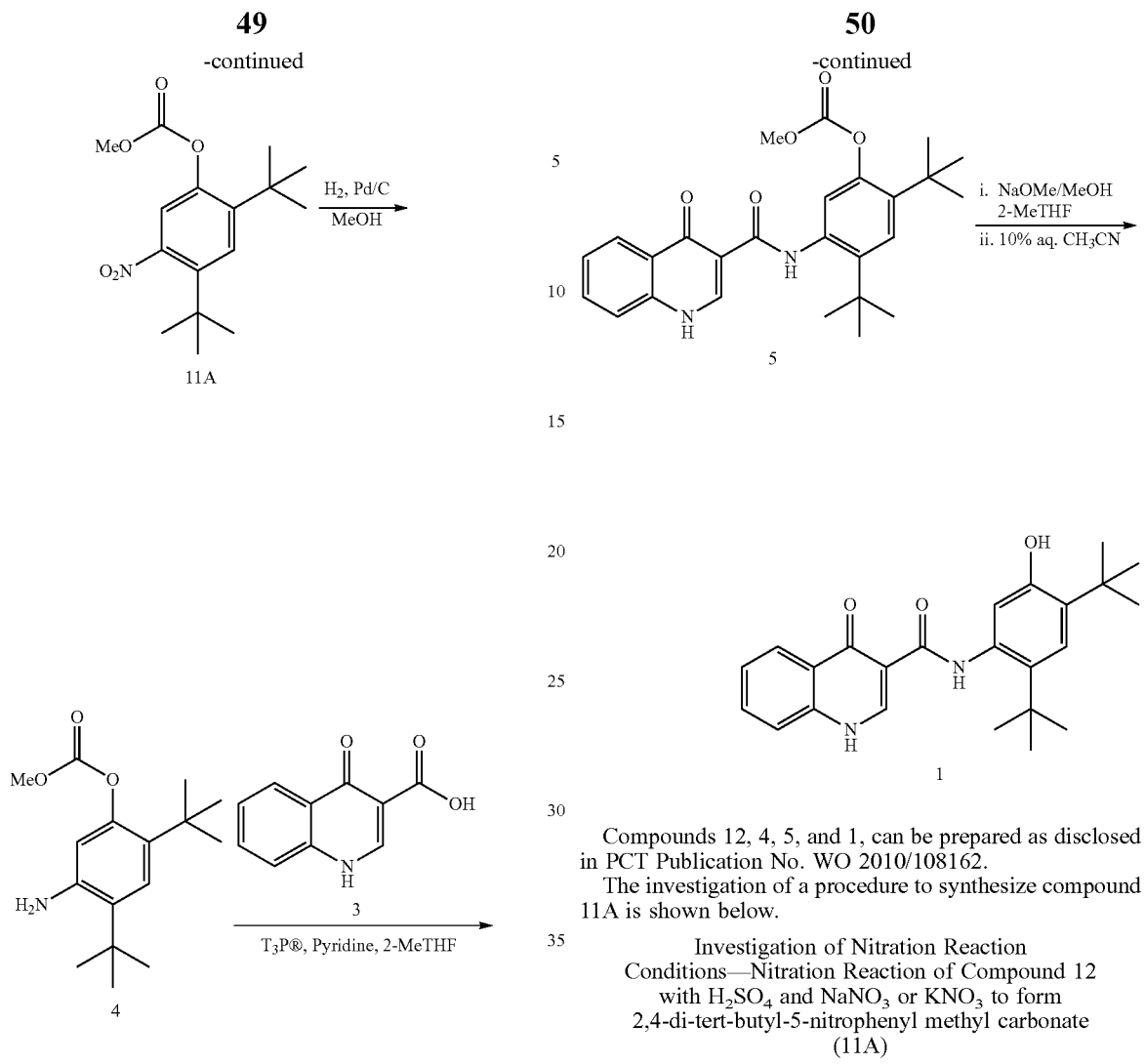

Compounds 12, 4, 5, and 1, can be prepared as disclosed in PCT Publication No. WO 2010/108162.

The investigation of a procedure to synthesize compound 11A is shown below.

Investigation of Nitration Reaction Conditions—Nitration Reaction of Compound 12 with $H_2SO_4$ and $NaNO_3$ or $KNO_3$ to form 2,4-di-tert-butyl-5-nitrophenyl methyl carbonate (11A)

TABLE 1

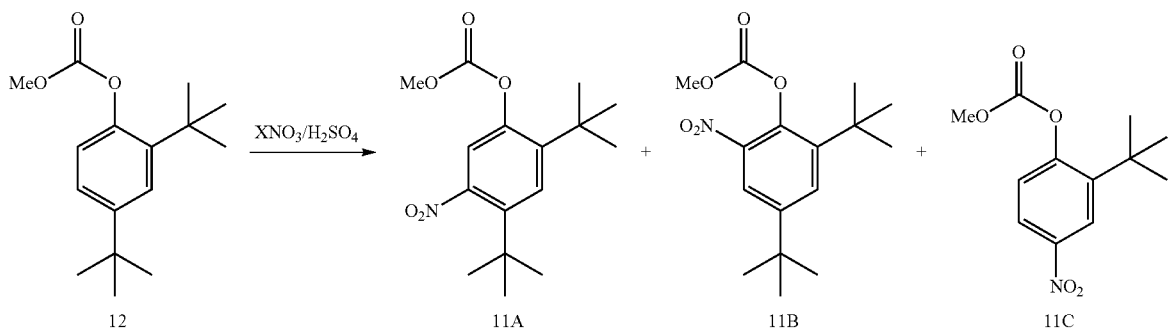 [SMILES: COC(=O)Oc1ccc(C(C)(C)C)cc1C(C)(C)C ; COC(=O)Oc1cc([N+](=O)[O-])c(C(C)(C)C)cc1C(C)(C)C ; COC(=O)Oc1c([N+](=O)[O-])cc(C(C)(C)C)cc1C(C)(C)C ; COC(=O)Oc1ccc([N+](=O)[O-])cc1C(C)(C)C]

| entry | —NO$_2$ source | acid | purity at end of reaction[1] (% 11A) | nitration ratio of 11A:11B:11C (unpurified) | isolated yield (%) | isolated purity (%) |
|---|---|---|---|---|---|---|
| 1 | HNO$_3$ | H$_2$SO$_4$ | 21 | 47:39:14 | 37 | 73 |
| 2 | HNO$_3$ | H$_2$SO$_4$ | 17 | 41:41:17 | — | — |
| 3 | KNO$_3$ | H$_2$SO$_4$ | 18 | 43:40:17 | — | — |
| 4 | KNO$_3$ | H$_2$SO$_4$ | 17 | 41:43:16 | — | — |

[1]HPLC purity of 11A in the reaction mixture once the reaction is completed, prior to any workup or isolation step.

Procedure for Nitration Reaction (Table 1, entry 1)

100 ml of 96% sulfuric acid were charged in reactor 1 and cooled to 0° C. 50 g of 2,4-di-tert-butylphenyl methyl carbonate (12) were added over the sulfuric acid maintaining the temperature below 10° C. Then the reactor was cooled to −5° C. To another reactor (reactor 2) 50 ml of 96% sulfuric acid and 14.4 ml of 65% nitric acid were charged, and the resulting mixture was cooled to −5° C. The contents of reactor 2 were added into reactor 1 maintaining the temperature below 0° C. The mixture was stirred at 0/−5° C. for 4 hours. The crude of reaction was quenched by adding it slowly over a mixture formed by 200 ml of DCM and 353 ml of water at 0° C. Then the mixture was heated to 20° C. and stirred for 1 hour. The phases were separated and the aqueous phase was washed with 100 ml of DCM. The combined organic phases were washed with 123 ml of water first and then with 160 ml of a 13% sodium chloride solution in water. The resulting organic solution was then concentrated under vacuum to 55 ml to obtain an oil that precipitated. The solid was dissolved with 155 ml of methanol at 65° C. The solution was distilled at atmospheric pressure until 155 ml. 20 ml of methanol were added and the solution was cooled to 25/30° C. in 2 hours and stirred at this temperature for 1 hour. The solids were filtered and washed with 11.5 ml of methanol to yield 24.06 g of 2,4-di-tert-butyl-5-nitrophenyl methyl carbonate (11A) as wet solid with a 10.6% of methanol. Yield: 37% HPLC purity: 73%.

Investigation of Nitration Reaction Conditions—Nitration Reaction of Compound 12 with Trimethylsilylchloride, AlC$_3$, and KNO$_3$ to form 2,4-di-tert-butyl-5-nitrophenyl methyl carbonate (11A)

TABLE 2

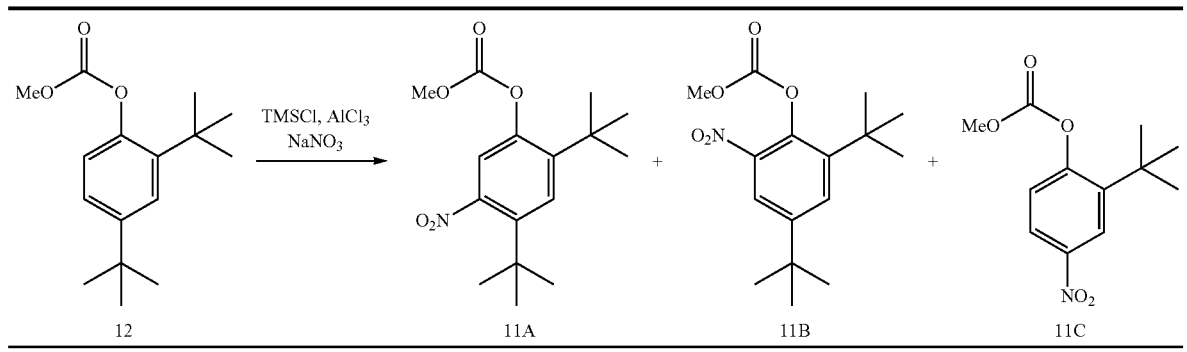

| entry | KNO$_3$ (equiv) | TMSCl (equiv) | AlCl$_3$ (equiv) | T (° C.) | purity at end of reaction[1] (% 11A) | nitration ratio of 11A:11B:11C (unpurified) |
|---|---|---|---|---|---|---|
| 1 | 1.5 | 2.0 | 3.0 | 0 | 55 | 85:5:10 |
| 2 | 1.5 | 2.0 | 3.0 | 0 | 43 | 82:4:14 |
| 3 | 1.5 | 2.0 | 3.0 | 0 | 57 | 89:6:4 |
| 4 | 1.1 | 2.5 | 3.3 | 0 | 47 | 87:9:4 |
| 5 | 1.1 | 2.5 | 3.3 | 20 | 42 | 64:30:6 |
| 6 | 1.1 | 2.5 | 4.5 | 20 | 36 | 88:0:12 |
| 7 | 1.2 | 2.0 | 3.0 | 0 | 46 | 66:34:0 |
| 8 | 1.5 | 2.0 | 3.0 | −15 | 53 | 91:6:3 |
| 9 | 1.5 | 2.0 | 3.0[2] | −15 | 21 | 48:46:6 |

[1]HPLC purity of 11A in the reaction mixture once the reaction is completed, prior to any workup or isolation step.

Procedure for Nitration Reaction (Table 2, entry 1)

1.15 g of potassium nitrate and 14.6 ml of dichloromethane were charged into a reactor. The suspension was cooled to 0° C. 1.95 ml of chloromethylsilane were added at 0° C. and then 2.0 g of 2,4-di-tert-butylphenyl methyl carbonate (12) and 2 ml of dichloromethane. 3.03 g of aluminum trichloride were added slowly at 0° C. and the mixture was stirred then at this temperature for 20 hours. The reaction was then quenched by adding 20 ml of water maintaining the temperature below 30° C. 15 ml of dichloromethane were charged and the mixture was heated to 25° C. The two phases were separated and the aqueous phase was washed with 20 ml of dichloromethane. The combined organic phases were washed with 20 ml of water two times and the resulting organic phase was concentrated to dryness to yield 2.044 g (87.4%) of 2,4-di-tert-butyl-5-nitrophenyl methyl carbonate (11A). HPLC purity: 55%.

Investigation of Nitration Reaction
Conditions—Nitration Reaction of Compound 12
with AlCl₃/NaNO₃ to form
2,4-di-tert-butyl-5-nitrophenyl methyl carbonate
(11A)

TABLE 3

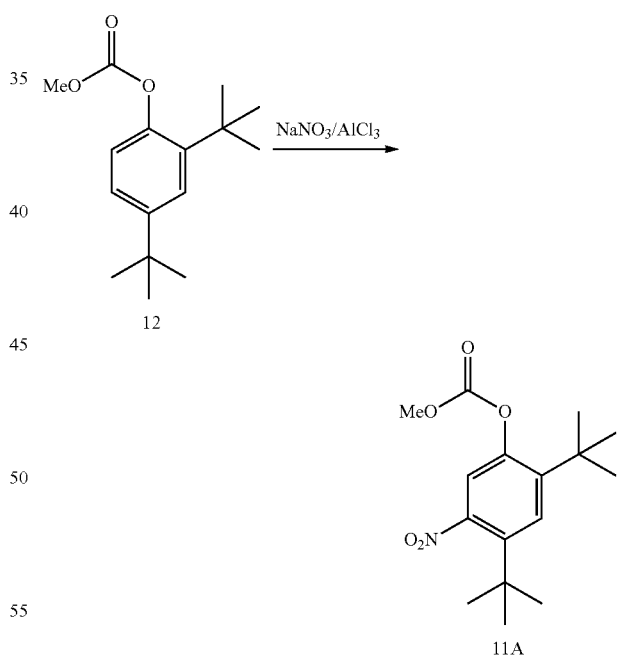

| entry | NaNO₃ (equiv) | AlCl₃ (equiv) | T (° C.) | purity at end of reaction1 (% 11A) | nitration ratio of 11A:11B:11C (unpurified) | isolated yield (%) | isolated purity (%) |
|---|---|---|---|---|---|---|---|
| 1 | 1.2 | 3.0 | −15 | 88 | 96:3:1 | 87 | 99.3 |
| 2 | 1.2 | 3.0 | −15 | 89 | 96:3:1 | 87 | 99.6 |

¹HPLC purity of 11A in the reaction mixture once the reaction is completed, prior to any workup or isolation step.

Procedure for Nitration Reaction (Table 3, entry 2)

143.75 g of aluminum trichloride and 789 ml of methylene chloride were charged to a 1 liter reactor. The mixture was cooled to 0° C. and 36.65 g of sodium nitrate were added. The crude of reaction was stirred at 0° C. for 3 hours. Then the reactor was cooled to −20° C. and 95 g of 2,4-di-tert-butylphenyl methyl carbonate (12) dissolved in 76 ml of methylene chloride were added while maintaining the temperature at −15° C. The mixture was then stirred for twenty hours at −15° C. In another reactor 665 ml of 2M hydrochloric acid were charged and cooled to 3° C., then the crude of reaction was quenched slowly over the hydrochloric solution at 10° C. The mixture was heated to 20° C. and stirred for 1 hour at this temperature before separating both layers. The aqueous phase was washed with 190 ml of methylene chloride that were combined with the initial organic phase. The two combined organic phases were washed three times with 510 ml of sodium chloride solution containing 475 ml of water and 95 g of sodium chloride each. The resulting organic phase was concentrated under vacuum to 190 ml and then 618 ml of methanol were added. The mixture was concentrated again to a final volume of 570 ml and heated to 64° C. 190 ml of methanol are added to the mixture while maintaining 64° C. to obtain complete dissolution of the solids. Then the mixture was cooled to 55° C. and maintained at this temperature for 1 hour. Later it was cooled to 2° C. in 2 hours and stirred at this temperature for 2 additional hours before filtering the solid. The wet cake was washed twice with 47.5 ml of cold methanol and the wet solids were dried at 45° C. under vacuum to yield 96.15 g (86.5%) of 2,4-di-tert-butyl-5-nitrophenyl methyl carbonate (11A). HPLC purity: 99.6%

Synthesis of 2,4-di-tert-butyl-5-nitrophenyl Methyl Carbonate (11A)

Methylene chloride (3091 L) was charged into a reactor and cooled to −5-5° C., then aluminum trichloride (564 kg) and sodium nitrate (144 kg) were added. The mixture was stirred at −1-5° C. for not less than 3 hours and then further cooled to −20--12° C. A solution of 2,4-di-tert-butylphenyl methyl carbonate (373 kg) in methylene chloride (300 L) was added while maintaining the temperature at −20--12° C. After the addition, the mixture was maintained at −21--15° C. The completeness of the reaction was measured by HPLC with in-process control sample taken after 2 hours. The reaction was considered complete when the peak area of 2,4-di-tert-butylphenyl methyl carbonate was less than 4.5%.

In another reactor 2N hydrochloric acid solution was prepared (526 kg of concentrated HCl in 1864 L of water) and cooled to 0±5° C. The reaction mixture was then added slowly to the hydrochloric solution at not more than 20° C. to quench the reaction. The mixture temperature was heated to 15-21° C. and stirred for 1 hour before separating both layers. The aqueous phase was washed with methylene chloride (745 L, 2.0 vol) at 15 to 21° C. The combined organic phase was washed three times with 16.7% sodium chloride aqueous solution (prepared by the dissolution of NaCl (298 kg) in water (1491 L) at 15 to 21° C.). The resulting organic phase was then concentrated to 746 L at not more than 45° C., and methanol (3169 L) was added. The resulting mixture was concentrated to 2237 L at not more than 65° C. and then additional methanol (373 L) was added. The mixture was concentrated again to 2237 L at not more than 65° C. and then heated to reflux (~65° C.) to dissolve any solids present. If any solids were still present, methanol (373 L) was added while maintaining the temperature at reflux. This procedure was repeated until all solids were dissolved. At this point the solution was cooled to 45-55° C. until crystallization was observed and maintained at this temperature for 1 hour. The resulting slurry was cooled at −5-5° C. in 2-5 hours and stirred at this temperature for one additional hour before filtration. The filter cake was washed twice with cold methanol (298 L).

The crude product (402 kg), methylene chloride (804 L) and methanol (804 L) were charged into a reactor. The mixture was heated to 40-45° C. until all solids completely dissolved. The solution was treated with activated carbon for not less than 1 hour at 40-45° C. After the filtration, methanol (804 L) was added. The solution was concentrated to 804 L under vacuum at not more than 45° C. Methanol (804 L) was added and the resulting slurry was concentrated to 804 L under vacuum at not more than 45° C. Methanol (804 L) was added again. The slurry was cooled at −10-0° C. in 2-5 hours and then stirred at this temperature for minimum 3 hours before filtration. The filter cake was washed twice with cold methanol (402 L).

The wet cake was dried at not more than 50° C. under vacuum until residual methanol and methylene chloride contents were less than 5000 ppm. A light yellow solid, 2,4-di-tert-butyl-5-nitrophenyl methyl carbonate (11A), was obtained (364.9 kg, 99.9% purity measured by HPLC analysis) with 83.6% yield.

Example 2: N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (2)

The overall scheme of the synthesis of compound 2 is shown below, followed by the procedure for the synthesis of each intermediate.

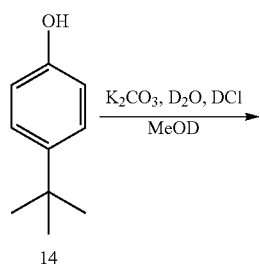

14

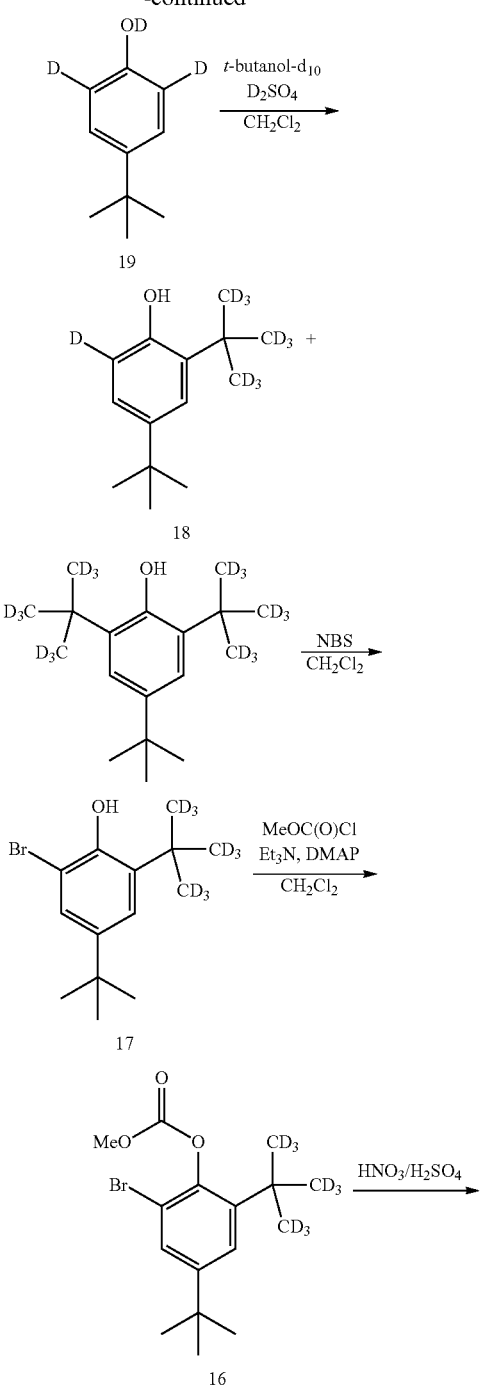

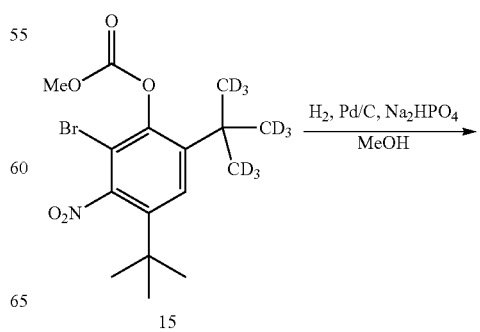

15

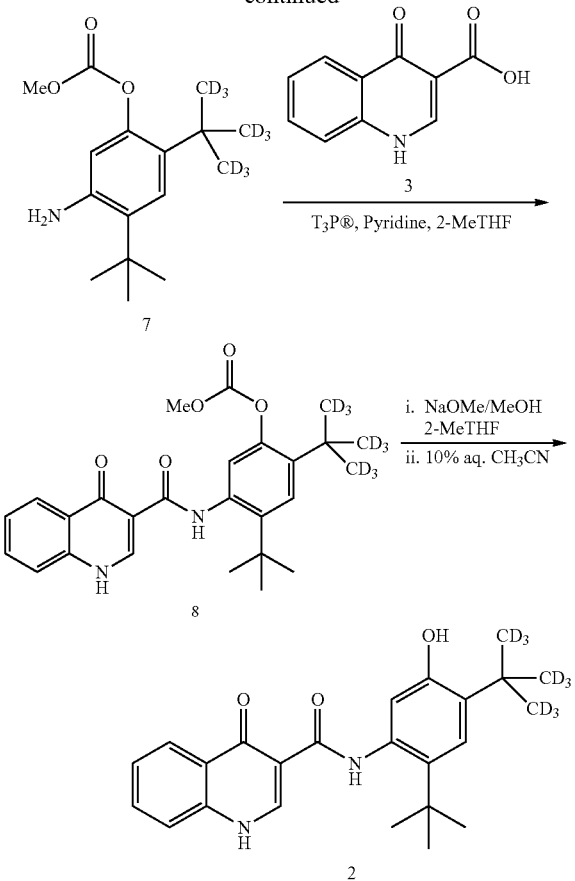

Procedure for the Synthesis of 4-(tert-butyl)phen-2,6-d2-ol-d (19)

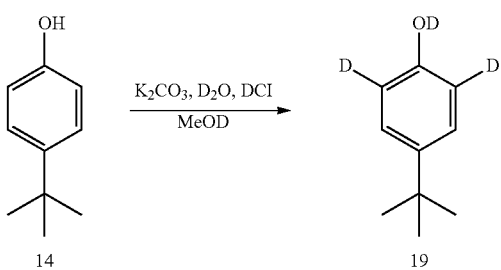

To a 5 L round bottom flask equipped with overhead stirrer was charged 4-tert-butylphenol (14, 503.2 g), K$_2$CO$_3$ (46.3 g), D$_2$O (1949 g, 1761 mL, 3.5 vol), and MeOD (409 g, 503 mL, 1.0 vol). The mixture was heated to reflux under a nitrogen atmosphere. The reaction mixture was aged at reflux for 16 hours. The reaction mixture was cooled to room temperature and sampled for conversion (% D incorporation). The reaction was cooled to 5° C. and 35% DCl solution (90 g, 71.2 mL) was added. The reaction mixture was aged at 5° C. for 2 hours. The resultant slurry was filtered and the cake washed with D$_2$O (836 g, 755 mL, 1.5 vol). This process was repeated until the target % D incorporation is met (normally two exchanges required). The wet cake is dried in a vacuum oven with a nitrogen bleed at 40° C. until a constant weight is obtained. Yield of 4-(tert-butyl)phen-2,6-d2-ol-d (19) is 506 g of a white solid (98%) with a purity of 99.6% and % D incorporation of 99.3%.

Procedure for the Synthesis of 4-(tert-butyl)-2-(2-(methyl-d3)propan-2-yl-1,1,1,3,3,3-d6)phen-6-d-ol-d and 4-(tert-butyl)-2,6-bis(2-(methyl-d3)propan-2-yl-1,1,1,3,3,3-d6)phenol-d (18)

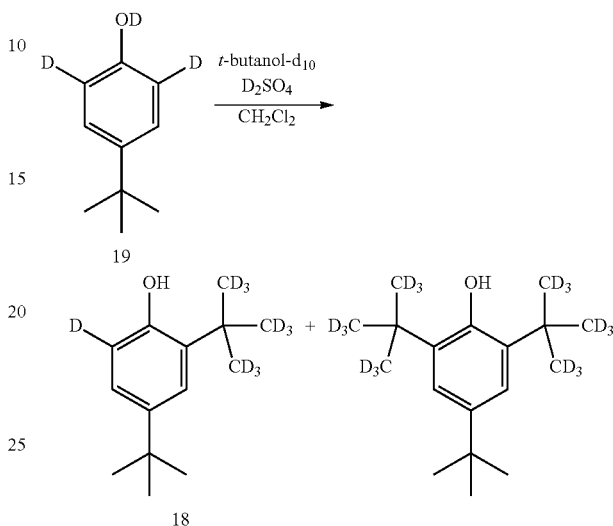

4-(tert-butyl)phen-2,6-d2-ol-d (19) (101.8 g, 0.66 mol, 1.0 equiv.) was dissolved in CH$_2$Cl$_2$ (400 mL) in a 2 L reactor. tert-Butanol-d$_{10}$ (43.0 g, 0.51 mol, 0.77 equiv.) was dissolved in CH$_2$Cl$_2$ (100 mL) in a 250 mL flask. The solution of tert-butanol-d$_{10}$ was charged to the 2 L reactor at room temperature. The reaction mixture was cooled to −5° C. D$_2$SO$_4$ (51.1 g, 0.51 mol, 0.77 equiv.) was charged dropwise via an addition funnel while maintaining a temperature range of −4 to −2° C. The reaction mixture was stirred at −2° C. for 3-4 hours. Upon complete conversion the reaction was quenched by adding water (28 mL) and warmed to 18-20° C. The bottom aqueous layer was drained and discarded. The CH$_2$Cl$_2$ layer was treated with sat. aq. NaHCO$_3$ solution (approximately 200 mL), adjusting the pH to 6-8. NaCl (sat.) solution (400 mL) was charged to the mixture. The resulting solution was stirred for 5 min, and settled for 5 min. The lower CH$_2$Cl$_2$ layer was drained into a 1 L flask. The aqueous layer was discarded. The CH$_2$Cl$_2$ solution was concentrated to minimal volume and n-heptane (200 mL) was charged. The solution was concentrated to minimal volume and n-heptane charged to a final volume of 800 mL. 0.5 N NaOH solution 600 mL (6 vol) was charged to the reactor and the resulting mixture was stirred for 5 min, and settled for at least 5 min. The aqueous layer was drained and discarded. 1.0 N NaOH solution 300 mL (3 vol) was charged to the reactor and the resulting mixture was stirred for 5 min, and settled for at least 5 min. The aqueous layer was drained and discarded. 1.0 N NaOH solution 300 mL (3 vol) was charged to the reactor and the resulting mixture was stirred for 5 min, and settled for at least 5 min. The aqueous layer was drained and discarded. The remaining n-heptane solution was concentrated to dryness to afford the desired product, 4-(tert-butyl)-2-(2-(methyl-d3)propan-2-yl-1,1,1,3,3-d6)phen-6-d-ol-d (18) as a clear oil, 104.5 g, which was carried forward into the next step without further purification.

Procedure for the Synthesis of 2-bromo-4-(tert-butyl)-6-(2-(methyl-d3)propan-2-yl-1,1,1,3,3,3-d6)phenol (17)

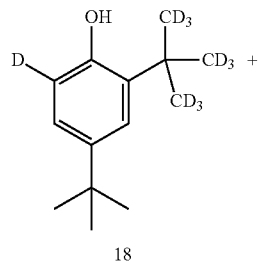

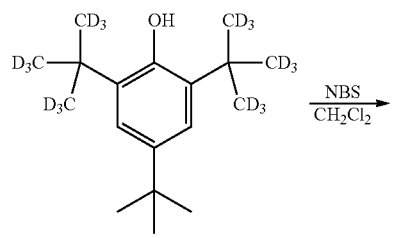

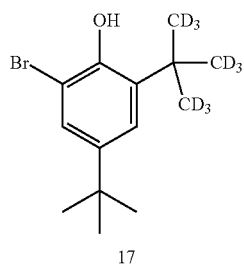

4-(tert-butyl)-2-(2-(methyl-d3)propan-2-yl-1,1,1,3,3,3-d6)phen-6-d-ol-d (18) (100 g, 0.462 mol, 1.0 equiv.) was dissolved in CH$_2$Cl$_2$ (800 mL, 7 vol) in a 2 L reactor and the solution was stirred. The batch was cooled down to 0±3° C. To the batch was charged portion-wise N-bromosuccinimide (84.4 g, 0.462 mol, 1.0 equiv) over 30 min. The batch was stirred at 0±2° C. for at least 30 minutes. The batch was then heated to 20±2° C. over a period of 2 hours, and stirred at 20±2° C. for at least 12 hours. Upon complete conversion, sat. aq. NaHCO$_3$ solution (500 mL, 5 vol) was charged and the batch stirred for at least 10 minutes. The agitation was stopped to allow the phases to separate for at least 5 minutes and the CH$_2$Cl$_2$ layer was drained, followed by removal of the aqueous layer. The CH$_2$Cl$_2$ layer was charged back to the vessel. To the batch was charged sat. aq. NaHCO$_3$ bicarbonate solution (500 mL, 5 vol), and the batch was stirred for at least 10 minutes. The agitation was stopped to allow the phases to separate for at least 5 minutes and the CH$_2$Cl$_2$ layer was drained, followed by removal of the aqueous layer. The CH$_2$Cl$_2$ layer was charged back to the vessel and diluted with an additional CH$_2$Cl$_2$ (300 mL, 3 vol). The batch was distilled (removal of 300 ml) and checked by KF to achieve dryness. The resulting clear yellow solution of 17 was carried forward into the next step without further purification.

Procedure for the Synthesis of 2-bromo-4-(tert-butyl)-6-(2-(methyl-d3)propan-2-yl-1,1,1,3,3,3-d6)phenyl methyl carbonate (16)

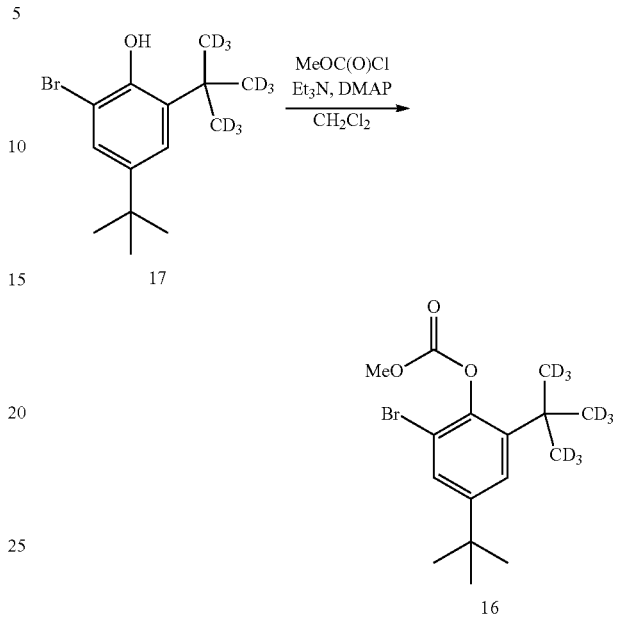

To a clean reactor was charged the CH$_2$Cl$_2$ solution of 4-(tert-butyl)-2-(2-(methyl-d3)propan-2-yl-1,1,1,3,3,3-d6)phen-6-d-ol-d (17) (136 g, 0.462 mol, 1.0 equiv.) followed by additional CH$_2$Cl$_2$ (130 mL, 1 vol), and this solution was stirred. To the batch was charged 4-(dimethylamino)pyridine (2.8 g, 0.023 mol, 0.05 equiv) and triethylamine (70.1 g, 0.693 mol, 1.5 equiv). The batch was cooled to 0±3° C. To the batch was charged drop-wise methyl chloroformate (48.0 g, 0.508 mol, 1.1 equiv) over 40 minutes while maintaining a batch temperature ≤5° C. The batch was stirred at 3±2° C. for at least 30 minutes, and then warmed to 20±2° C. over a period of 1 hour. Upon complete conversion, 1 N HCl (400 mL, 3 vol) was charged. The batch was stirred for at least 10 minutes, and then the layers were allowed to separate for at least 5 minutes. The lower organic layer was drained followed by the aqueous layer (1$^{st}$ aqueous layer). The organic layer was charged back to the reactor, along with 1 N HCl solution (400 mL, 3 vol). The batch was stirred for at least 10 minutes, and then the layers were allowed to separate for at least 5 minutes. The lower organic layer was drained. The 1$^{st}$ aqueous layer was charged to the reactor, along with CH$_2$Cl$_2$ (300 mL, 2.2 vol). The batch was stirred for at least 10 minutes, and then the layers were allowed to separate for at least 5 minutes. The lower organic layer was drained and combined with the 1$^{st}$ organic layer, followed by removal of the aqueous layer. Charge the vessel with the contents of both organic layers. The reactor was charged with water (500 mL, 3.7 vol). The batch was stirred for at least 10 minutes, and then the layers were allowed to separate for at least 5 minutes. The lower organic layer was drained, followed by the aqueous layer. The organic layer was charged back to the reactor, along CH$_2$Cl$_2$ (400 mL, 3 vol). The batch was distilled to remove 800 ml and checked by KF to ensure dryness. The resulting clear yellow solution of 16 was telescoped into the next step without further purification.

Procedure for the Synthesis of 2-bromo-4-(tert-butyl)-6-(2-(methyl-d3)propan-2-yl-1,1,1,3,3,3-d6)-3-nitr0phenyl methyl carbonate (15)

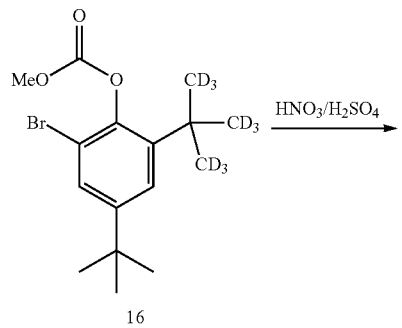

16

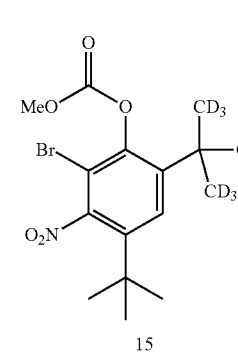

15

To a reactor was charged 2-bromo-4-(tert-butyl)-6-(2-(methyl-d3)propan-2-yl-1,1,1,3,3,3-d6)phenyl methyl carbonate (16) and then the solution was cooled to 0° C. Sulfuric acid (4.9 equiv) and nitric acid (100%, 2.0 equiv) was charged while maintaining a temperature of not more than 5° C. The reaction was stirred at 0° C. for 2 hours until complete conversion. The reaction was then quenched with water (8.8 vol) and diluted with $CH_2Cl_2$ (1.7 vol). The layers were separated and the upper aqueous layer was extracted with $CH_2Cl_2$ (2.8 vol). After separating the layers, the organic layers were combined, returned to the reactor, and washed with sodium bicarbonate (7.4% w/w, 6.8 vol). After separating the layers, the organic layer was returned to the reactor and washed with sodium chloride (23% w/w, 3.8 vol). After separating the layers, the organic layer was returned to the reactor and concentrated to minimal volume. Methanol (1.2 vol) was charged, followed by concentration to minimal volume. Methanol (1.2 vol) was charged, followed by concentration to minimal volume. Methanol (1.7 vol) was charged, and the slurry was heated to reflux for 30 min and then cooled slowly over 4 hours to 5° C. The solid product (15) was filtered and the cake washed with cold methanol (1.0 vol). The solid 2-bromo-4-(tert-butyl)-6-(2-(methyl-d3)propan-2-yl-1,1,1,3,3,3-d6)-3-nitrophenyl methyl carbonate (15) was dried under vacuum at 40-50° C. to yield an off-white solid, 99.9% purity and 99% D incorporation.

Procedure for the Synthesis of 5-amino-4-(tert-butyl)-2-(2-(methyl-d3)propan-2-yl-1,1,1,3,3,3-d6)phenyl methyl carbonate (7)

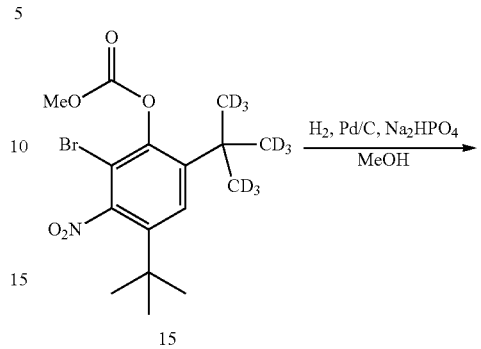

15

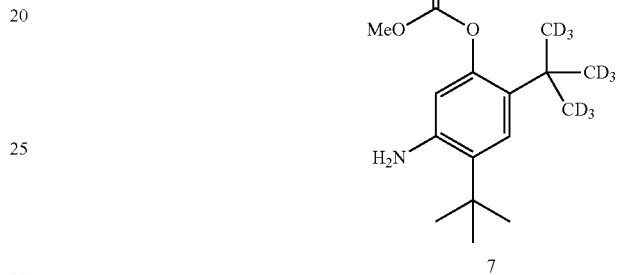

7

Charge 5 wt % (50-65 wt % wet, JM Type 37) of 5% Pd/C to a reactor. Charge (4.0 vol) Methanol. Close the system. Purge with $N_{2\ (g)}$ at 2.0 Bar. Activate with $H_{2\ (g)}$ at 2.0 Bar. Charge the vessel to 2.0 Bar with $H_{2\ (g)}$ at 25° C.+/−5° C. Stir for not less than 2 hours while maintaining a temperature of 25° C.+/−5° C. Vent and purge with $N_{2\ (g)}$ at 2.0 Bar. Charge compound 15 (1.0 eq) to a reactor, together with $Na_2HPO_4$ (2.3 eq). Charge (11.0 vol) Methanol. Close the system. Purge with $N_{2\ (g)}$ at 2.0 Bar. Activate with $H_{2\ (g)}$ at 2.0 Bar. Charge the vessel to 2.0 Bar with $H_{2\ (g)}$ at 25° C.+/−5° C. Stir for about 24 hours while maintaining a reaction temperature of 25° C.+/−5° C. Upon complete conversion, dilute reaction mixture by adding 7.7 vol of MeOH. Heat reaction mixture to 35.0° C.+/−5° C. Filter off catalyst and $Na_2HPO_4$. Wash the reactor and filter cake with Methanol (4.0 vol), and filter, combining with the initial filtrate. Check Pd content and if needed perform resin treatment (resin treatment is: Charge SPM-32 resin (5 wt %). Stir the resin treated solution for not less than 3 hours at 35.0° C.+/−5° C. Filter off resin. Wash the reactor and filter cake with Methanol (2.0 vol), and filter, combining with the initial filtrate). Charge Norit CASP active carbon (3 wt %). Stir for not less than 3 hours at 35.0° C.+/−5° C. Filter off active carbon. Wash the reactor and filter cake with Methanol (2.0 vol), and filter, combining with the initial filtrate. Distill under vacuum at not more than 50° C. to 8.0 vol. Charge water (2.0 vol) while maintaining a temperature of 45° C.+/−5° C. Cool the resultant slurry to 0° C.+/−5° C. over 2 hours. Hold and stir the slurry at 0° C.+/−5° C. for not less than 1 hour. Filter and wash the cake with 2.0 volumes Methanol/Water (8:2) at 0° C.+/−5° C. Dry 5-amino-4-(tert-butyl)-2-(2-(methyl-d3)propan-2-yl-1,1,1,3,3,3-d6)phenyl methyl carbonate (7) under vacuum at not more than 40° C. to give a yield of a white solid, >99.5% purity.

Procedure for the Synthesis of 4-(tert-butyl)-2-(2-(methyl-d3)propan-2-yl-1,1,1,3,3,3-d6) -5-(4-oxo-1,4-dihydroquinoline-3-carboxamido)phenyl methyl carbonate (8)

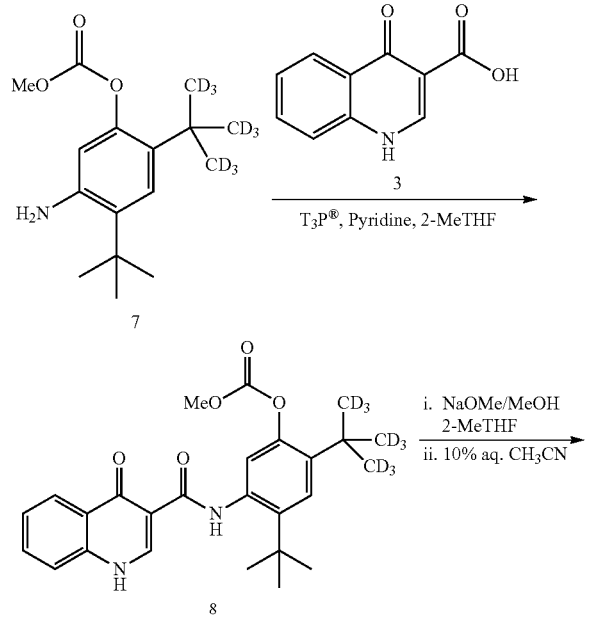

The procedure for the conversion of compound 7 into compound 8 may be performed according to the analogous procedure for compound 5.

Procedure for the Synthesis of N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (2)

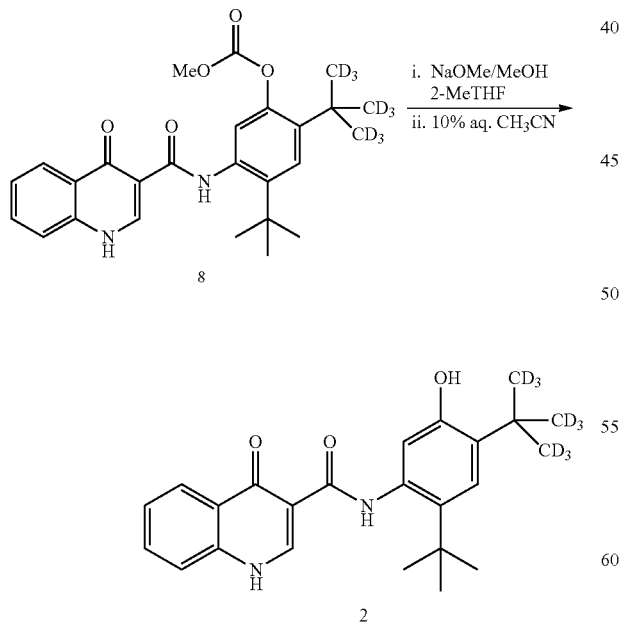

The procedure for the conversion of compound 8 into compound 2 may be performed according to the analogous procedure for the synthesis of compound 1.

Example 3: Synthesis of 5-amino-4-(tert-butyl)-2-(2-(methyl-d3)propan-2-yl-1,1,1,3,3,3-d6)phenyl methyl carbonate (7)

An alternative overall scheme of the synthesis of compound 7 is shown below, followed by the procedure for the synthesis of each synthetic intermediate.

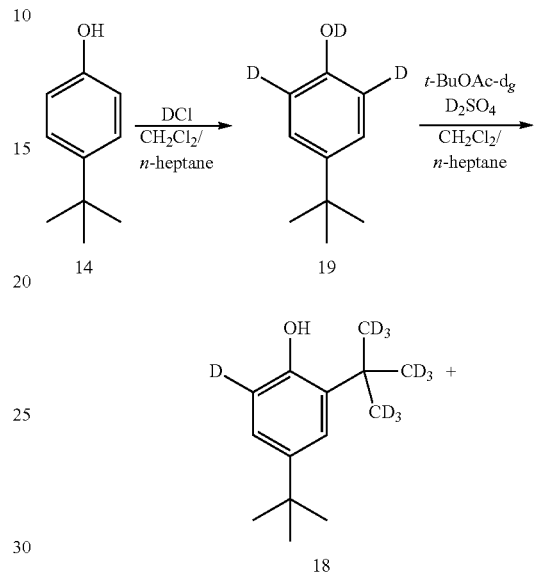

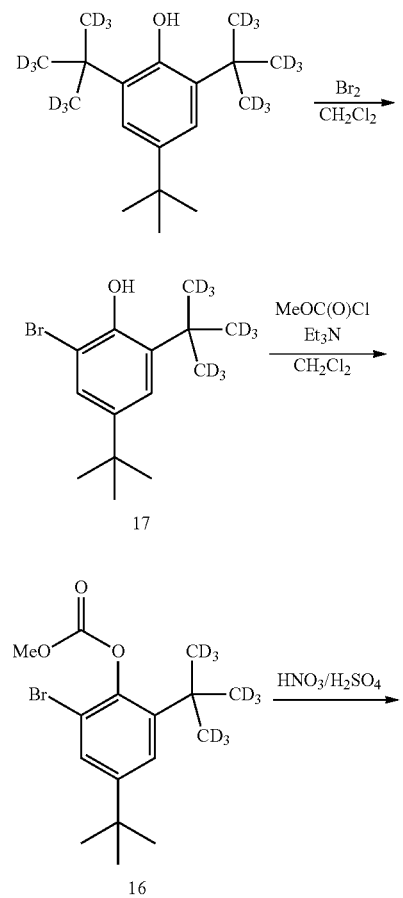

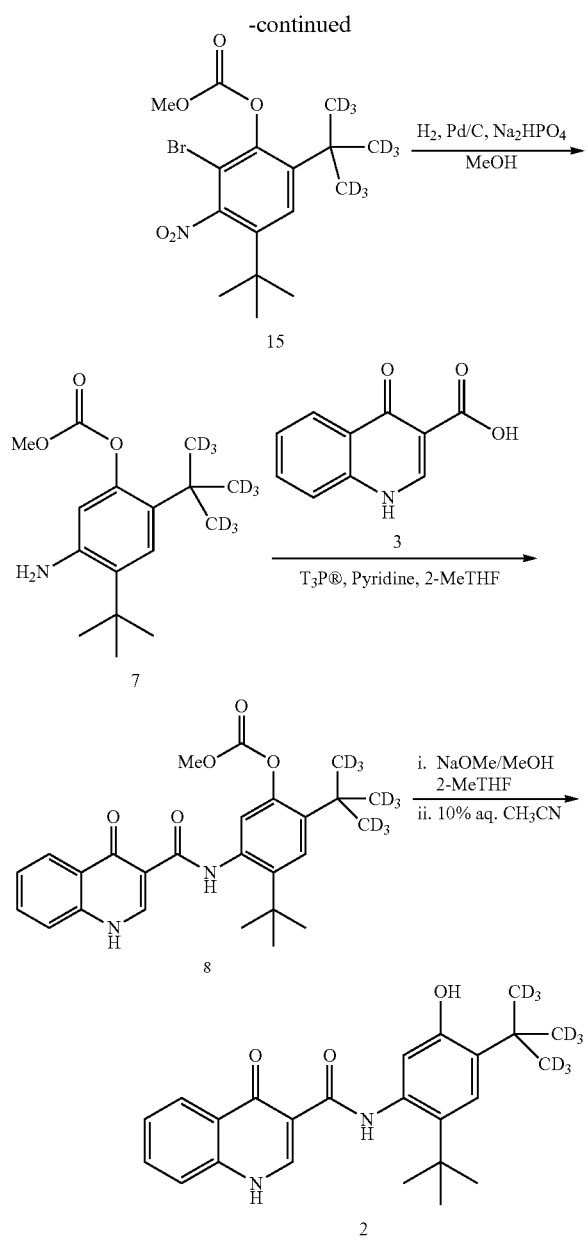

Procedure for the Synthesis of 4-(tert-butyl)phen-2,6-d2-ol-d (19)

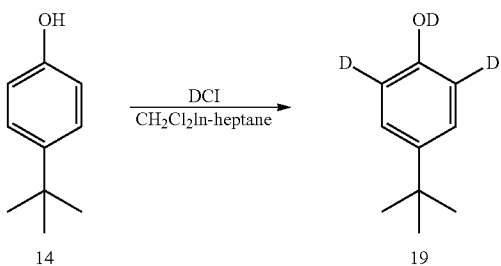

To a clean and dry 500-mL reactor was charged 4-tert-butylphenol (14) (24.6 g, 0.162 mmol, 1.00 equiv), CH$_2$Cl$_2$ (64 mL, 2.6 vol), and heptane (64 mL, 2.6 vol), and this mixture was warmed to 25° C. and stirred until all solids dissolved. To this solution was charged deuterium chloride (35% w/w in deuterium oxide, 25 mL, 1.0 vol), and this mixture was agitated for at least 3.5 hours. The agitation was stopped and the phases were allowed to separate, and then the aqueous layer (bottom) was drained from the reactor. To the reactor was charged deuterium chloride (35% w/w in deuterium oxide, 25 mL, 1.0 vol), and this mixture was agitated for at least 3.5 hours. The agitation was stopped and the phases were allowed to separate, and then the aqueous layer (bottom) was drained from the reactor. To the reactor was charged deuterium chloride (35% w/w in deuterium oxide, 25 mL, 1.0 vol), and this mixture was agitated for at least 3.5 hours. The agitation was stopped and the phases were allowed to separate, and then the aqueous layer (bottom) was drained from the reactor. The resulting solution was sampled and confirmed to be at least 99% of the desired deuterium incorporation product 4-(tert-butyl)phen-2,6-d2-ol-d (19) relative to starting material 4-tert-butylphenol. The solution in the reactor was carried on to the next step described below.

Procedure for the Synthesis of 4-(tert-butyl)-2-(2-(methyl-d3)propan-2-yl-1,1,1,3,3,3-d6)phen-6-d-ol (18)

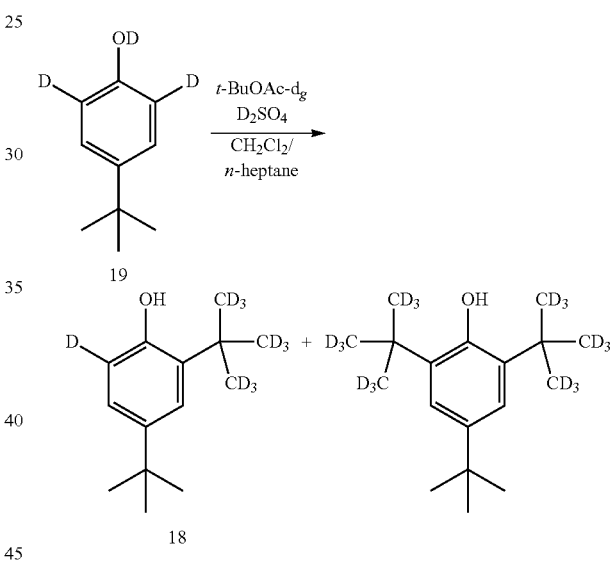

To the methylene chloride solution containing the reaction mixture of 4-(tert-butyl)phen-2,6-d2-ol-d (19) was charged CH$_2$Cl$_2$ (125 mL, 5 vol). Approximately 125 mL of the reaction solution was distilled from the reactor using a distillation head and heating the reactor to 60° C. To the reactor was charged CH$_2$Cl$_2$ (125 mL, 5 vol). Approximately 100 mL of the reaction solution was then distilled from the reactor, and at this time the solution was sampled to confirm water content (KF) was less than 300 ppm and determine the CH$_2$Cl$_2$ and heptane content. After measuring the batch volume, CH$_2$Cl$_2$ (8 mL, 0.24 vol) was charged to adjust the total CH$_2$Cl$_2$ content to 3 vol and heptane (68 mL, 2.8 vol) was charged to adjust the heptane content to 4.5 vol. To the solution was charged tert-butyl acetate-d9 (30.2 g, 1.46 equiv), and the resulting solution was cooled to 0° C. To the solution was charged sulfuric acid-d$_2$ (8.12 g, 0.49 equiv) over at least 15 min, and the solution was agitated for 2 hours while maintaining the temperature at 0-5° C. After this time, the temperature was set to ramp up to 20° C. over two hours and the solution was agitated for another 14 hours. The solution was sampled to confirm 4-tert-butylphenol (14) or 4-(tert-butyl)phen-2,6-d2-ol-d (19) were present at less than 3%. To the reactor was charged $CH_2Cl_2$ (58 mL, 2.4 vol) and heptane (90 mL, 3.7 vol), and the solution was cooled to 0-5° C. before charging water (125 mL, 5 vol). The mixture was agitated for 15 min before agitation was stopped and the phases were allowed to separate. After the aqueous phase (bottom) was drained from the reactor, 0.5 N aqueous NaOH (125 mL, 5 vol) was charged and the temperature was adjusted to 20° C. The mixture was agitated for 20 min before agitation was stopped and the phases were allowed to separate. The organic phase (top) was sampled to confirm 4-tert-butylphenol (14) or 4-(tert-butyl)phen-2,6-d2-ol-d (18) were present at less than 0.5%. The aqueous phase (bottom) was drained from the reactor. The solution in the reactor was carried on to the next step described below.

Procedure for the Synthesis of 2-bromo-4-(tert-butyl)-6-(2-(methyl-d3)propan-2-yl-1,1,1,3,3,3-d6)phenol (17)

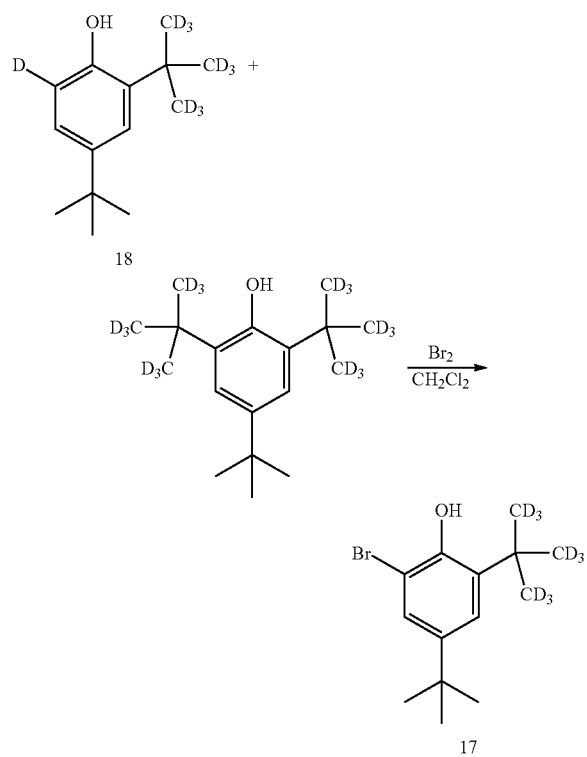

After the agitated solution of the alkylation reaction to produce 4-(tert-butyl)-2-(2-(methyl-d3)propan-2-yl-1,1,1,3,3,3-d6)phen-6-d-ol-d (18) was brought to 0-5° C., bromine (38.4 g, 1.45 equiv) was charged over at least 1 hour, maintaining the temperature below 5° C. The solution was sampled to confirm 4-(tert-butyl)-2-(2-(methyl-d3)propan-2-yl-1,1,1,3,3,3-d6)phen-6-d-ol was present at less than 1%. To the solution was charged sodium metabisulfite (20% w/w aqueous solution, 147 g, 0.95 equiv) over at least 1 hour, maintaining the temperature below 10° C. After adjusting the temperature to 20° C., the mixture was agitated for another 1 hour. Agitation was stopped and the phases were allowed to separate. The aqueous phase (bottom) was drained from the reactor, and water (125 mL, 5 vol) was charged to the reactor. The mixture was agitated for 15 min before stopping agitation and allowing the phases to separate. The aqueous phase (bottom) was drained from the reactor. The solution of 17 in the reactor was carried on to the next step described below.

Surprisingly, this bromination reaction significantly improved the selectivity of the nitration reaction. Another unexpected advantage to this process was that bromination converted the mixture of compound 18 and 4-(tert-butyl)-2,6-bis(2-(methyl-d3)propan-2-yl-1,1,1,3,3,3-d6)phenol to the same desired product (17). This significantly improved the overall yield.

Procedure for the Synthesis of 2-bromo-4-(tert-butyl)-6-(2-(methyl-d3)propan-2-yl-1,1,1,3,3,3-d6)phenyl methyl carbonate (16)

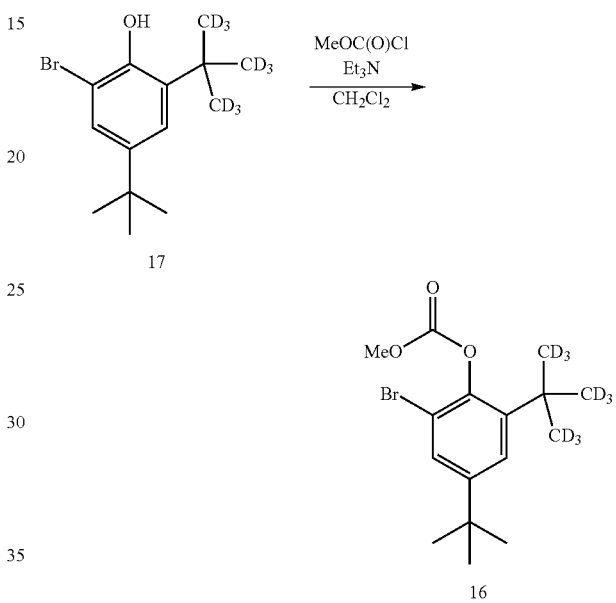

To the solution of the bromination reaction to produce 2-bromo-4-(tert-butyl)-6-(2-(methyl-d3)propan-2-yl-1,1,1,3,3,3-d6)phenol (17) was charged $CH_2Cl_2$ (125 mL, 5 vol). Approximately 125 mL of the reaction solution was distilled from the reactor using a distillation head and heating the reactor to 60° C. To the reactor was charge $CH_2Cl_2$ (125 mL, 5 vol). Approximately 125 mL of the reaction solution was distilled from the reactor. To the reactor was charged $CH_2Cl_2$ (125 mL, 5 vol). Approximately 125 mL of the reaction solution was then distilled from the reactor, and at this time the solution was sampled to confirm water content (KF) was less than 300 ppm and determine the $CH_2Cl_2$ and heptane content. After measuring the batch volume, $CH_2Cl_2$ was charged to adjust the total $CH_2Cl_2$ content to 5.3 vol and heptane was charged to adjust the heptane content to 8 vol. To the solution was charged triethylamine (31.7 g, 1.91 equiv), and the solution was cooled to 0-5° C. To the solution was charged methyl chloroformate (24.1 g, 1.56 equiv) over at least 1 hour, maintaining the temperature below 10° C. The solution was agitated for 1 hour, and a sample of the solution was taken to confirm 2-bromo-4-(tert-butyl)-6-(2-(methyl-d3)propan-2-yl-1,1,3,3,3-d6)phenol (17) was present at less than 1%. To the solution was charged 1 N aqueous hydrochloric acid (125 mL, 0.76 equiv) over at least 30 min, maintaining the temperature below 10° C. The temperature was then adjusted to 20° C., and agitation was stopped and the phases were allowed to separate. After the aqueous phase (bottom) was drained from the reactor, water (125 mL, 5 vol) was charged to the reactor. The mixture was agitated for 15 min before agitation was stopped and the phases were allowed to separate. After the aqueous phase (bottom) was drained from the reactor, water (125 mL, 5 vol) was charged to the reactor. The mixture was agitated for 15 min before agitation was stopped and the phases were allowed to separate. The aqueous phase (bottom) was drained from the reactor. The solution of 16 in the reactor was carried on to the next step described below.

Procedure for the Synthesis of 2-bromo-4-(tert-butyl)-6-(2-(methyl-d3)propan-2-yl-1,1,1,3,3,3-d6)-3-nitrophenyl methyl carbonate (15)

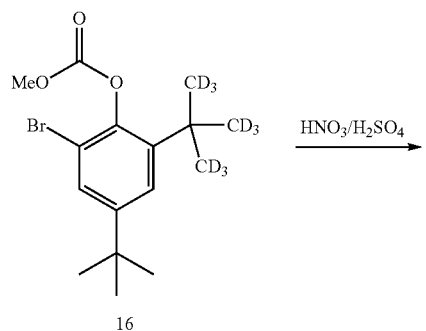

16

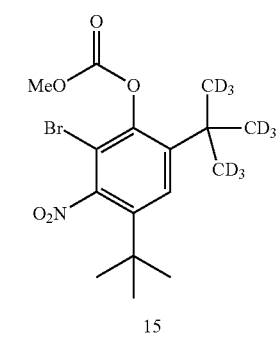

15

To the solution of the protection reaction to produce 2-bromo-4-(tert-butyl)-6-(2-(methyl-d3)propan-2-yl-1,1,1,3,3,3-d6)phenyl methyl carbonate (16) was charged $CH_2Cl_2$ (125 mL, 5 vol). Approximately 125 mL of the reaction solution was distilled from the reactor using a distillation head and heating the reactor to 60° C. To the reactor was charged $CH_2Cl_2$ chloride (125 mL, 5 vol). Approximately 125 mL of the reaction solution was distilled from the reactor. To the reactor was charged $CH_2Cl_2$ (125 mL, 5 vol). To the reactor was charged $CH_2Cl_2$ (125 mL, 5 vol). Approximately 125 mL of the reaction solution was distilled from the reactor. Approximately 125 mL of the reaction solution was then distilled from the reactor, and at this time the solution was sampled to confirm water content (KF) was less than 300 ppm and determine the $CH_2Cl_2$ and heptane content. After measuring the batch volume, $CH_2Cl_2$ was charged to adjust the total $CH_2Cl_2$ content to 6 vol and heptane was charged to adjust the heptane content to 9 vol. After cooling the solution to 0-5° C., sulfuric acid (172 g, 10.3 equiv) was charged over at least 30 min, maintaining the temperature below 5° C. To the mixture was charged nitric acid (70% w/w, 19.1 g, 1.31 equiv) over at least 30 min, maintaining the temperature below 10° C. After agitating the mixture for 1 hour, a sample was taken and analyzed to confirm 2-bromo-4-(tert-butyl)-6-(2-(methyl-d3)propan-2-yl-1,1,1,3,3,3-d6)phenyl methyl carbonate (16) was present at less than 1%. To the mixture was charged water (100 mL, 4 vol) over at least 1 hour, maintaining the temperature below 10° C. Agitation was stopped and the phases were allowed to separate, and the aqueous phase (bottom) was drained from the reactor. After resuming agitation, sodium bicarbonate (8% w/w aqueous solution, 100 mL, 4 vol, 0.62 equiv) was charged over at least 10 min, maintaining the temperature below 10° C. The temperature was adjusted to 20° C., agitation was stopped, and the phases were allowed to separate. After draining the aqueous phase (bottom) from the reactor, water (100 mL, 4 vol) was charged to the reactor and the mixture was agitated for 15 min. Agitation was stopped, the phases were allowed to separate, and the aqueous phase (bottom) was drained from the reactor. To the mixture was charged water (100 mL, 4 vol), and this mixture was agitated for 15 min. Agitation was stopped, the phases were allowed to separate, and the aqueous phase (bottom) was drained from the reactor. After marking the solvent level on the reactor, a distillation head was attached and the temperature was set to 80° C. To the solution was charged methanol (570 mL, 23 vol) while distilling at the same time, matching the addition rate to the distillation rate by keeping the solvent level at the mark. Distillation was continued until the batch volume was approximately 264 mL (11 vol) and approximately 1.10 kg of distillate had been removed. The mixture was sampled and analyzed to confirm heptane was present at less than 1% v/v. The temperature was adjusted to 0° C. over 4 hours. The mother liquor was sampled and analyzed to determine the concentration of 2-bromo-4-(tert-butyl)-6-(2-(methyl-d3)propan-2-yl-1,1,1,3,3,3-d6)-3-nitrophenyl methyl carbonate (15), and the mixture was filtered. To the reactor was charged methanol (51.1 mL, 2 vol), and this was agitated until the temperature reached 0-5° C. This solution was used to wash the filter cake, and the filter cake was then dried by suction for at least 1 hour. The solid was then submitted to vacuum drying to produce 2-bromo-4-(tert-butyl)-6-(2-(methyl-d3)propan-2-yl-1,1,1,3,3,3-d6)-3-nitrophenyl methyl carbonate (15) as 41.5 g of an off-white solid (98.4% pure w/w, 63% yield after purity correction).

Procedure for the Synthesis of 5-amino-4-(tert-butyl)-2-(2-(methyl-d3)propan-2-yl-1,1,1,3,3,3-d6)phenyl methyl carbonate (7)

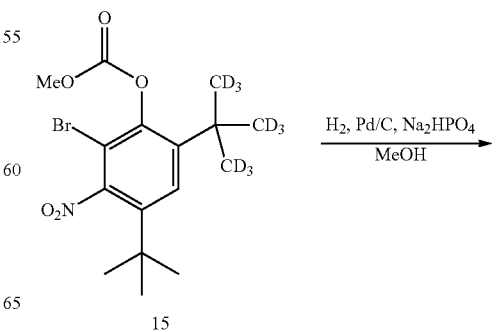

15

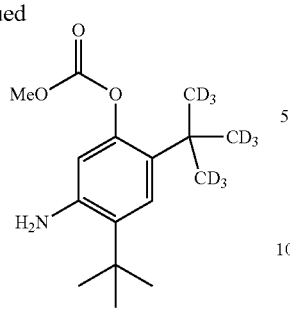

7

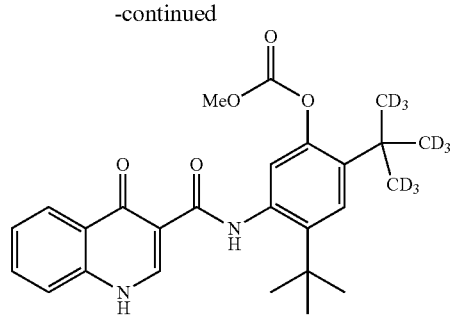

8

Charge 5 wt % (50-65 wt % wet, JM Type 37) of 5% Pd/C to a reactor. Charge (4.0 vol) Methanol. Close the system. Purge with N$_2$ (g) at 2.0 Bar. Activate with H$_{2\ (g)}$ at 2.0 Bar. Charge the vessel to 2.0 Bar with H$_{2\ (g)}$ at 25° C.+/−5° C. Stir for not less than 2 hours while maintaining a temperature of 25° C.+/−5° C. Vent and purge with N$_{2\ (g)}$ at 2.0 Bar. Charge compound 15 (1.0 eq) to a reactor, together with Na$_2$HPO$_4$ (2.3 eq). Charge (11.0 vol) Methanol. Close the system. Purge with N$_{2\ (g)}$ at 2.0 Bar. Activate with H$_{2\ (g)}$ at 2.0 Bar. Charge the vessel to 2.0 Bar with H$_{2\ (g)}$ at 25° C.+/−5° C. Stir for about 24 hours while maintaining a reaction temperature of 25° C.+/−5° C. Upon complete conversion, dilute reaction mixture by adding 7.7 vol of MeOH. Heat reaction mixture to 35.0° C.+/−5° C. Filter off catalyst and Na$_2$HPO$_4$. Wash the reactor and filter cake with Methanol (4.0 vol), and filter, combining with the initial filtrate. Check Pd content and if needed perform resin treatment (resin treatment is: Charge SPM-32 resin (5 wt %). Stir the resin treated solution for not less than 3 hours at 35.0° C.+/−5° C. Filter off resin. Wash the reactor and filter cake with Methanol (2.0 vol), and filter, combining with the initial filtrate). Charge Norit CASP active carbon (3 wt %). Stir for not less than 3 hours at 35.0° C.+/−5° C. Filter off active carbon. Wash the reactor and filter cake with Methanol (2.0 vol), and filter, combining with the initial filtrate. Distill under vacuum at not more than 50° C. to 8.0 vol. Charge water (2.0 vol) while maintaining a temperature of 45° C.+/−5° C. Cool the resultant slurry to 0° C.+/−5° C. over 2 hours. Hold and stir the slurry at 0° C.+/−5° C. for not less than 1 hour. Filter and wash the cake with 2.0 volumes Methanol/Water (8:2) at 0° C.+/−5° C. Dry 5-amino-4-(tert-butyl)-2-(2-(methyl-d3)propan-2-yl-1,1,1,3,3,3-d6)phenyl methyl carbonate (7) under vacuum at not more than 40° C. to give a yield of a white solid, >99.5% purity.

Procedure for the Synthesis of 4-(tert-butyl)-2-(2-(methyl-d3)pr0pan-2-yl-1,1,1,3,3,3-d6)-5-(4-oxo-1,4-dihydr0quinoline-3-carboxamido)phenyl methyl carbonate (8)

The procedure for the conversion of compound 7 into compound 8 may be performed according to the analogous procedure for compound 5.

Procedure for the Synthesis of N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (2)

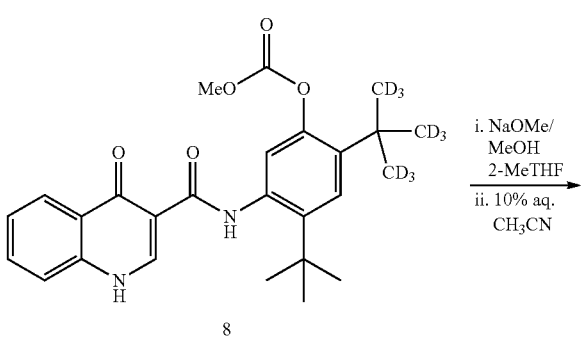

8

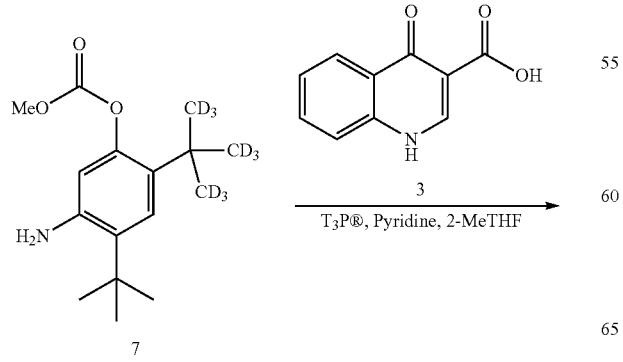

7

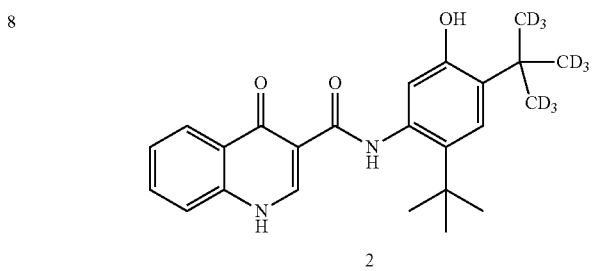

2

The procedure for the conversion of compound 8 into compound 2 may be performed according to the analogous procedure for the synthesis of compound 1.

Example 4: Synthesis of 5-amino-4-(tert-butyl)-2-(2-(methyl-d3)propan-2-yl-1,1,1,3,3,3-d6)phenyl methyl carbonate (7)
An alternative scheme of the synthesis of compound 7 is shown below, followed by the procedure for the synthesis of each synthetic intermediate.
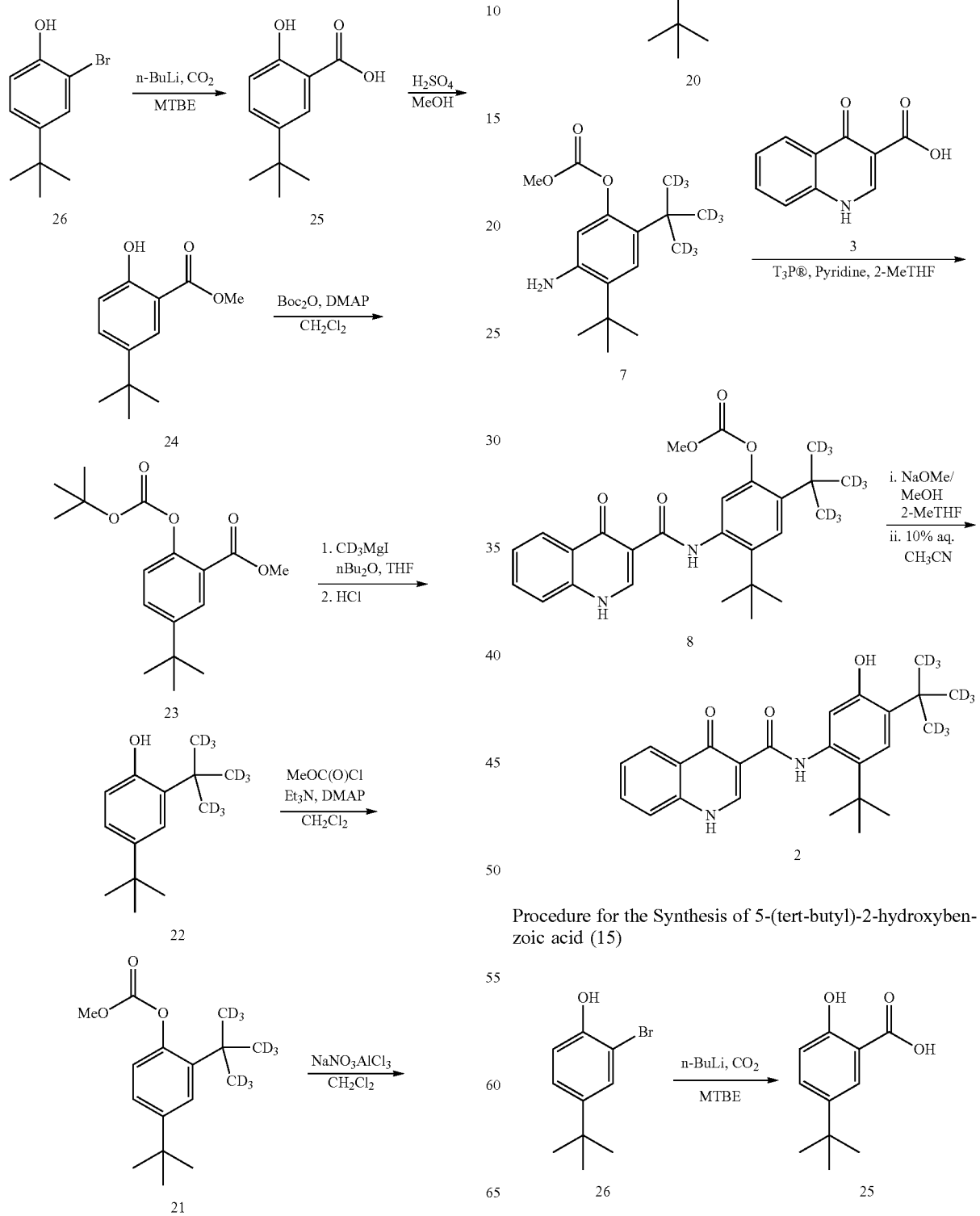
Procedure for the Synthesis of 5-(tert-butyl)-2-hydroxybenzoic acid (15)

nBuLi 1.6 M in hexanes (3.49 g) was added to a round bottom flask equipped with a magnetic stirbar, a thermocouple, and a N₂ bubbler. The round bottom flask was cooled down to −20° C. and stirring started. A solution of 2-bromo-4-tert-butylphenol (26) (5.00 g) in MTBE (12.5 mL) was prepared, cooled to −20° C., and charged to the round bottom flask drop wise while maintaining the temperature at −20° C.+/−5° C. The reaction mixture was stirred at −20° C.+/−5° C. for 15 min then allowed to warm up to 23° C. The completeness of the lithiation was measured by ¹H NMR (200 μL reaction mixture diluted into 0.75 mL d4-MeOH) after 15 min at room temperature. The reaction was considered complete when less than 1% 2-bromo-4-tert-butylphenol was observed. The reaction mixture was cooled down to 0° C., dry ice (solid CO₂) was added, and the reaction was stirred at room temperature for 45 min. Water (50.0 mL) was added to quench the reaction. The mixture was transferred into a separatory funnel, the phases were separated, and the organic phase was discarded. The aqueous phase was acidified to pH ~2 with 1 M HCl (15.0 mL), then extracted with MTBE (25.0 mL) three times. The combined organic extracts were concentrated under reduced pressure to yield 5-(tert-butyl)-2-hydroxybenzoic acid (25) as a yellow solid (2.25 g, 53.15% yield); ¹H NMR (400 MHz, d4-MeOH): 7.86 (1H, d, J=2.6 Hz), 7.54 (1H, dd, J=8.7, 2.6 Hz), 6.85 (1H, d, J=2.7 Hz), 1.30 (9H, s).

Procedure for the Synthesis of methyl 5-(tert-butyl)-2-hydroxybenzoate (24)

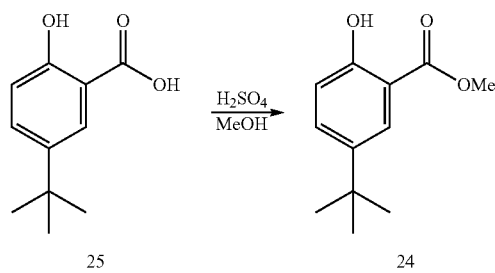

This reaction may be performed according to a procedure disclosed in Bioorganic and Medicinal Chemistry Letters, 2005, vol. 15, #21, p. 4752-4756.

Procedure for the Synthesis of methyl 2-((tert-butoxycarbonyl)oxy)-5-(tert-butyl)benzoate (23)

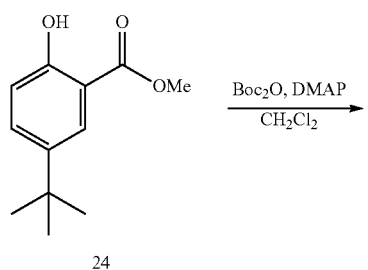

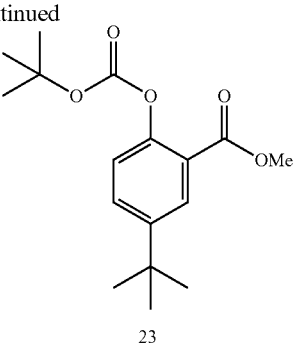

Di-tert-butyl carbonate (230.55 g) and CH₂Cl₂ (400 mL) were charged to a 1 L reactor and the mixture was stirred until the solids dissolved completely. (Dimethylamino)pyridine (0.587 g) was charged to the stirring solution along with methyl 5-(tert-butyl)-2-hydroxybenzoate (24) (200 g). The reaction mixture was stirred at 15-30° C. and the completeness measured by HPLC (method) with sample aliquots after 60 m. The reaction was considered complete when the peak area of 5-tert-butyl-2-hydroxybenzoate (24) was less than 1%. A half-saturated solution of ammonium chloride was prepared in a separate flask by diluting saturated aqueous ammonium chloride solution (200 mL) with water (200 mL). The reaction mixture was twice washed with half saturated aqueous ammonium chloride solution (200 mL each wash). During each wash, the mixture was stirred for 15 minutes and held for 15 minutes. The organic solution was subsequently washed twice with water (100 mL each wash). During each wash, the mixture was stirred for 15 minutes and held for 15 minutes. The organic solution was transferred to a 1 L round bottom flask and concentrated below 35° C. and under vacuum to yield a white solid (275.51 g and 99.46% purity as measured by HPLC analysis (method), a 93.0% yield of methyl 2-((tert-butoxycarbonyl)oxy)-5-(tert-butyl)benzoate (23)). ¹H NMR (400 MHz, CDCl₃): 8.01 (m, 1H); 7.57 (m, 1H); 7.11 (m, 1H); 3.89 (s, 3H); 1.58 (s, 9H); 1.33 (s, 9H).

Procedure for the Synthesis 4-(tert-butyl)-2-(2-(methyl-d3)propan-2-yl-1,1,1,3,3,3-d6)phenol (22)

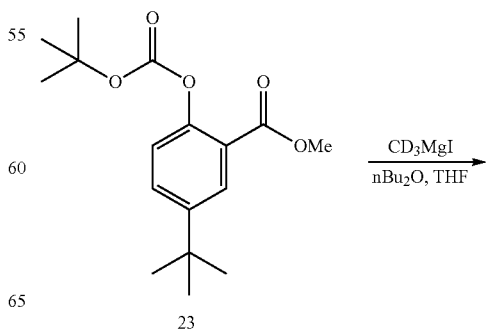

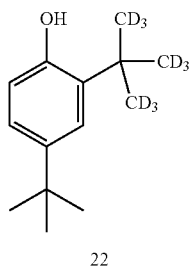

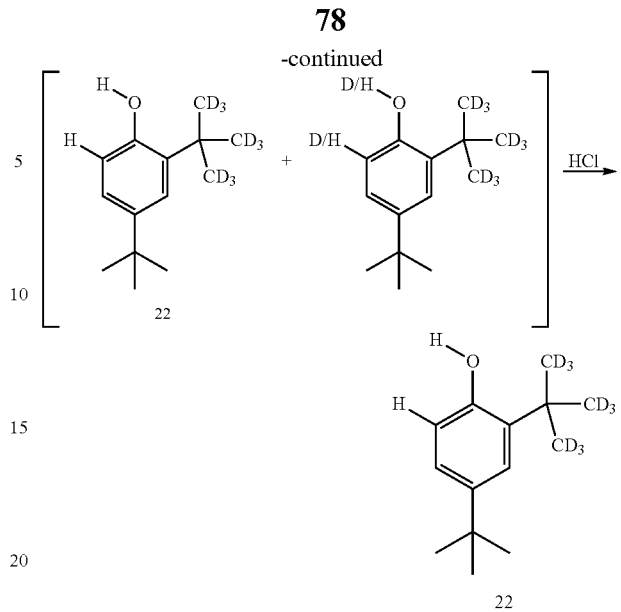

THF (176 mL) was charged to a 500 mL jacketed reactor and cooled to 5° C. To the stirring solvent and at 0-35° C. was slowly charged a solution of (methyl-d3)magnesium iodide (60.5 g) in dibutyl ether (145 mL). The resulting slurry was brought to and maintained at 20-30° C. while a solution of 2-((tert-butoxycarbonyl)oxy)-5-(tert-butyl)benzoate (23) (22 g) in THF (44 mL) was charged over 4-6 hours. The reaction mixture was stirred at 20-30° C. and the completeness measured by HPLC with sample aliquots after 60 m. The reaction was considered complete when the peak area of 2-((tert-butoxycarbonyl)oxy)-5-(tert-butyl)benzoate (23) was less than 1%. A second reactor was charged with 6N aqueous hydrochloric acid (110 mL) and the stirring solution was cooled to 0-10° C. The reaction slurry was slowly transferred to the acid solution at 0-35° C. The phases were stirred for 15 m and held for 15 m before being separated. The aqueous phase was extracted with dibutyl ether (132 mL). During the extraction the phases were stirred for 15 m and held for 15 m before being separated. The combined organic phases were washed sequentially with water (2×77 mL), 5% sodium thiosulfate aqueous solution (77 mL), and water (77 mL). During each wash, the mixture was stirred 15 minutes and held 15 minutes. The organic solution was transferred to a round bottom flask and concentrated below 80° C. and under vacuum to yield 4-(tert-butyl)-2-(2-(methyl-d3)propan-2-yl-1,1,1,3,3,3-d6) phenol (22) as a crude oil (5.94 g and 83.8% purity as measured by HPLC analysis with 99.3% D9 isotopic purity by LC/MS analysis, a 84.9% yield of methyl 4-(tert-butyl)-2-(2-(methyl-d3)propan-2-yl-1,1,1,3,3,3-d$_6$)phenol (23)). $^1$H NMR (400 MHz, CD$_3$OD): 7.22 (m, 1H); 7.00 (m, 1H); 6.65 (m, 1H); 1.26 (s, 9H).

The Grignard reaction of compound 23 led to some deuterium incorporation in compound 22. To effect H/D exchange, the mixture was subjected to a series of HCl washes:

Procedure for H/D Exchange

Charge the deuterated analogs of compound 22 (1.00 equiv) to a reactor. Charge DCM (5 vol). Set jacket to 20° C. Agitate to dissolved solids. Charge 35% hydrochloric acid (5 vol). Agitate to mix the layers for not less than 6 hours. Stop agitation and let the layers settle at least 30 min. Drain the bottom layer (organic) from the reactor. Drain the aqueous layer from the reactor. Charge the organic portion back into the reactor. Repeat HCl wash sequence twice. Charge pre-mixed water (2.5 vol) and sat. aq. NaCl (2.5 vol). Agitate to mix the layers for 30 min. Stop agitation and let the layers settle at least 30 min. Drain the bottom layer (organic) from the reactor. Drain the aqueous from the reactor. Charge the organic portion back into the reactor. Charge water (5 vol). Agitate to mix the layers for 30 min. Stop agitation and let the layers settle at least 30 min. Drain the bottom layer (organic) from the reactor. Drain the aqueous from the reactor. Charge the organic portion back into the reactor. Distill the solvent under reduced pressure to minimal volume (a rotovap with 35° C. bath temperature was used). Charge DCM (5 vol). Distill the solvent under reduced pressure to minimal volume (a rotovap with 35° C. bath temperature was used). Charge DCM (5 vol). Sample the solution and measure water content by KF. Repeat until the water content is less than 300 ppm. Note: This solution was used directly for the next reaction, so the final amount of DCM should be whatever is needed for the alkoxyformylation reaction of compound 22.

Procedure for the Synthesis of 4-(tert-butyl)-2-(2-(methyl-d3)propan-2-yl-1,1,1,3,3,3-d6)phenyl methyl carbonate (21)

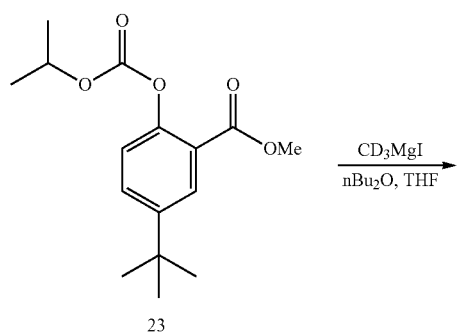

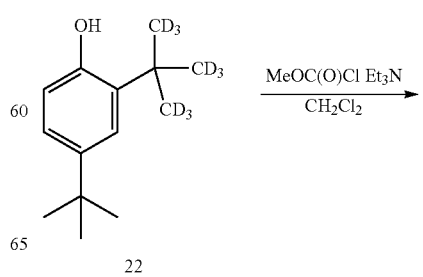

-continued

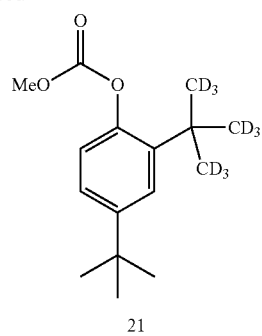

21

The procedure for the conversion of compound 22 into compound 21 may be performed according to the analogous procedure for compound 12.

Procedure for the Synthesis of 4-(tert-butyl)-2-(2-(methyl-d3)propan-2-yl-1,1,1,3,3,3-d6)-5-nitrophenyl methyl carbonate (20)

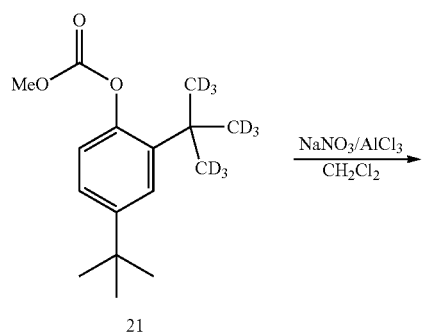

The procedure for the conversion of compound 21 into compound 20 may be performed according to the analogous procedure for compound 11A.

Procedure for the Synthesis of 5-amino-4-(tert-butyl)-2-(2-(methyl-d3)propan-2-yl -1,1,1,3,3,3-d6)phenyl methyl carbonate (7)

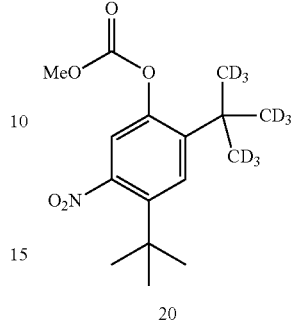

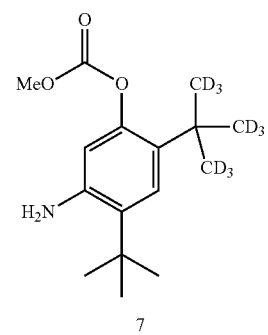

7

The procedure for the conversion of compound 20 into compound 7 may be performed according to the analogous procedure for compound 4.

Procedure for the Synthesis of 4-(tert-butyl)-2-(2-(methyl-d3)propan-2-yl-1,1,1,3,3,3-d6)-5-(4-oxo-1,4-dihydroquinoline-3-carboxamido)phenyl methyl carbonate (8)

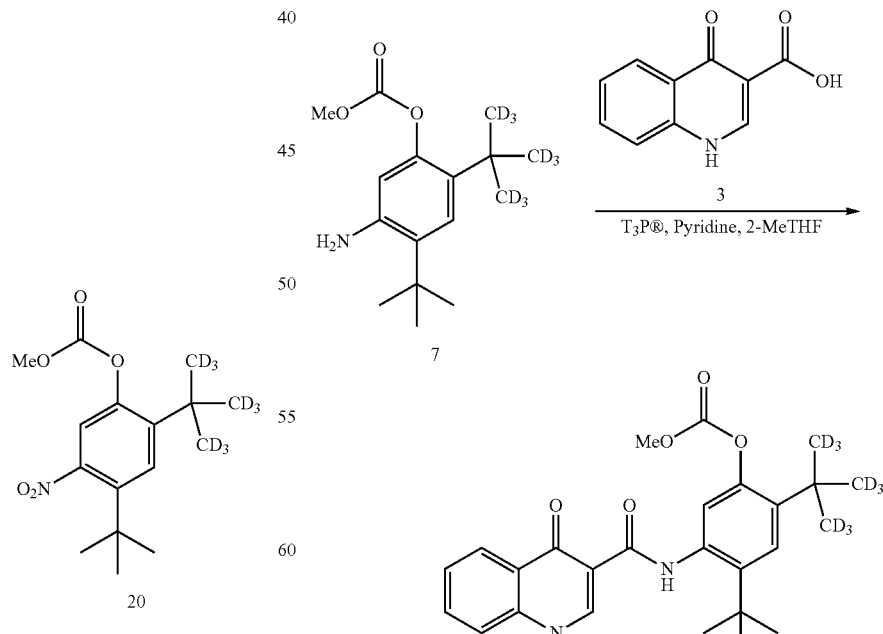

8

The procedure for the conversion of compound 7 into compound 8 may be performed according to the analogous procedure for compound 5.

Procedure for the Synthesis of N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (2)

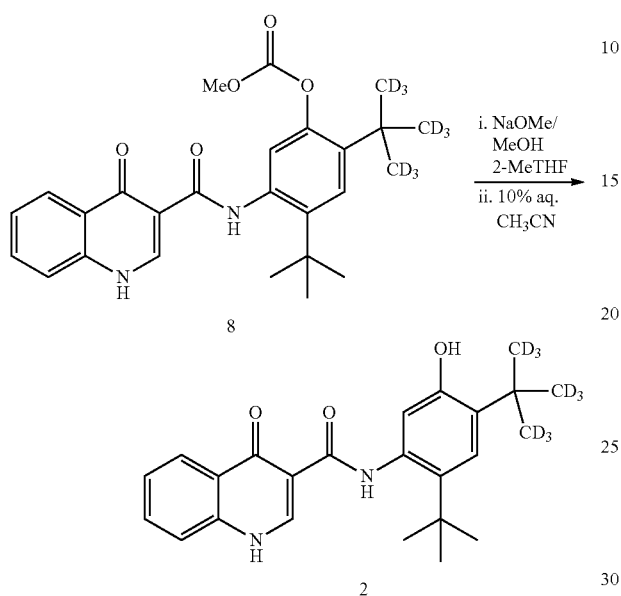

The procedure for the conversion of compound 8 into compound 2 may be performed according to the analogous procedure for the synthesis of compound 1.

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present disclosure. One skilled in the art will readily recognize from such discussion and from the accompanying drawings and claims, that various changes, modifications, and variations can be made therein without departing from the spirit and scope of the disclosure as defined in the following claims.

The invention claimed is:

1. A process for the preparation of compound 2:

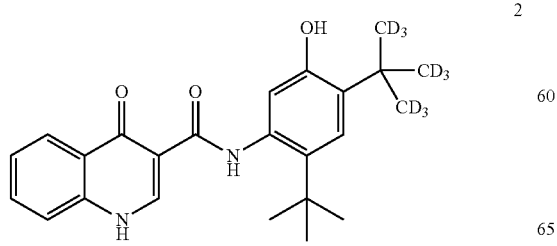

comprising:

a) converting compound 21:

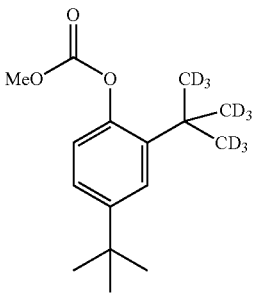

into compound 20:

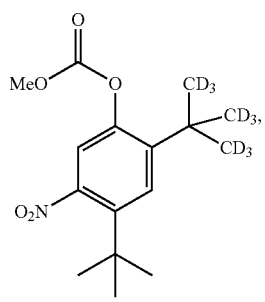

wherein the conversion of compound 21 into compound 20 is performed in the presence of $KNO_3$ and/or $NaNO_3$, $AlCl_3$, and optionally one or more of trimethylsilyl chloride and $TiCl_4$;

b) converting compound 20 into compound 7:

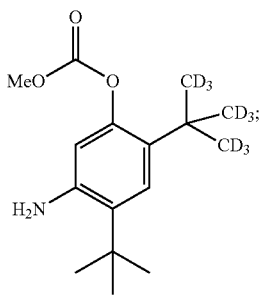

c) reacting compound 3:

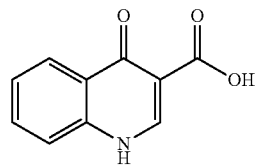

with compound 7 to produce compound 8:

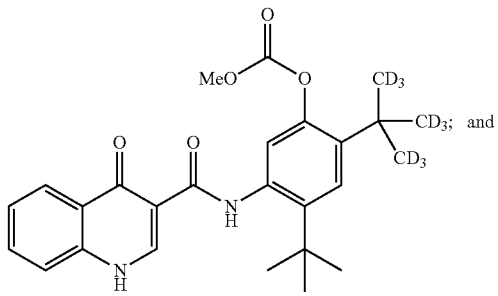

8

(d) converting compound 8 into compound 2;

wherein the methyl (Me) of the —OCO₂Me of compound 7, 8, 20, and 21 is optionally replaced by a group selected from aliphatic, heteroaliphatic, heterocyclic, haloaliphatic, aryl, and heteroaryl.

2. The process of claim 1, wherein the conversion of compound 21 into compound 20 is performed in the presence of $KNO_3$ and $AlCl_3$.

3. The process of claim 1, wherein the conversion of compound 21 into compound 20 is performed in the presence of $KNO_3$, $AlCl_3$, and trimethylsilyl chloride.

4. The process of claim 1, wherein the conversion of compound 21 into compound 20 is performed in the presence of $NaNO_3$ and $AlCl_3$.

5. The process of claim 1, wherein the conversion of compound 21 into compound 20 is performed in the presence of a solvent.

6. The process of claim 5, wherein the solvent is $CH_2Cl_2$.

7. The process of claim 1, wherein compound 21 is produced by converting compound 22:

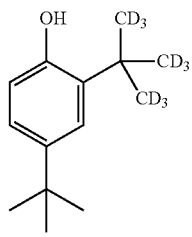

22 into compound 21.

8. The process of claim 7, wherein compound 22 is produced by converting compound 23:

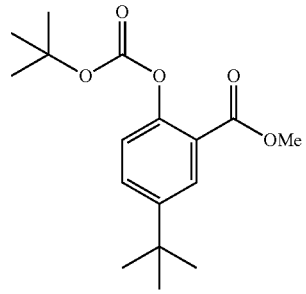

23 into compound 22 in the presence of $CD_3MgI$.

9. The process of claim 8, wherein compound 23 is produced by converting compound 24:

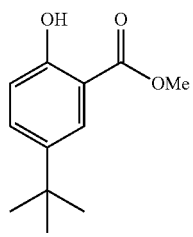

24 into compound 23.

10. The process of claim 9, further wherein compound 24 is produced by converting compound 25:

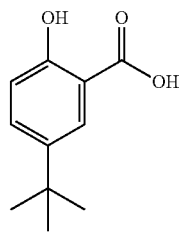

25 into compound 24.

11. The process of claim 10, wherein compound 25 is produced by converting compound 26:

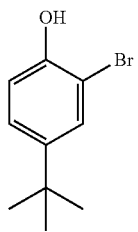

26 into compound 25.

12. A process for the preparation of compound 2:

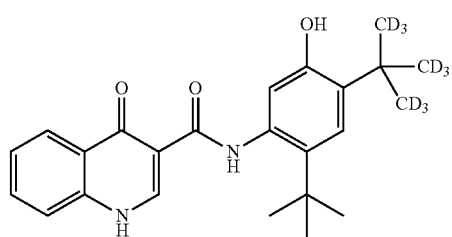

comprising:

a) converting compound 16:

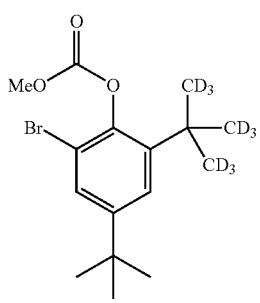

into compound 15:

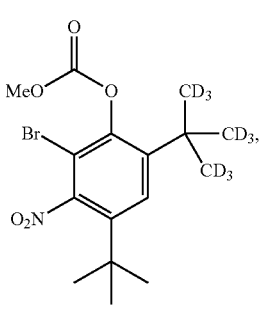

wherein the conversion of compound 16 into compound 15 is performed in the presence of KNO₃ and/or NaNO₃, AlCl₃, and optionally one or more of trimethylsilyl chloride and TiCl₄;

b) converting compound 15 into compound 7:

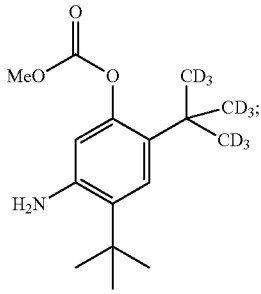

c) reacting compound 3:

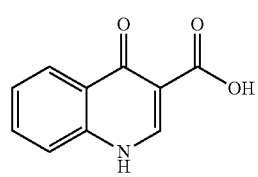

with compound 7 to produce compound 8:

(d) converting compound 8 into compound 2;
wherein the methyl (Me) of the —OCO₂Me of compounds 7, 8, 15, and 16 is optionally replaced by a group selected from aliphatic, heteroaliphatic, heterocyclic, haloaliphatic, aryl, and heteroaryl.

13. The process of claim 12, wherein the conversion of compound 16 into compound 15 is performed in the presence of KNO₃ and AlCl₃.

14. The process of claim 12, wherein the conversion of compound 16 into compound 15 is performed in the presence of KNO₃, AlCl₃, and trimethylsilyl chloride.

15. The process of claim 12, wherein the conversion of compound 16 into compound 15 is performed in the presence of NaNO₃ and AlCl₃.

16. The process of claim 12, wherein the conversion of compound 16 into compound 15 is performed in the presence of a solvent.

17. The process of claim 16, wherein the solvent is CH₂Cl₂.

18. The process of claim 12, wherein compound 16 is produced by converting compound 17:

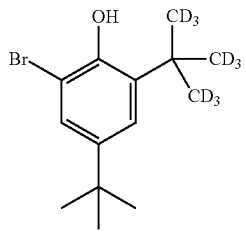

17 into compound 16.

19. The process of claim 18, wherein compound 17 is produced by converting compound 18:

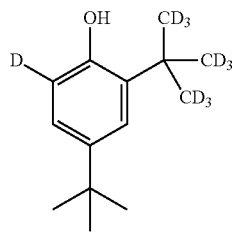

18 into compound 17.

20. The process of claim 19, wherein compound 18 is produced by converting compound 19:

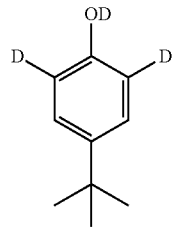

19 into compound 18.

21. The process of claim 20, wherein compound 19 is produced by converting tert-butyl phenol (compound 14):

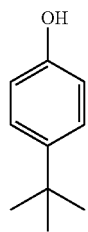

14 into compound 19.

* * * * *